US012629429B2

(12) United States Patent
Bosch Tubert et al.

(10) Patent No.: US 12,629,429 B2
(45) Date of Patent: May 19, 2026

(54) FIBROBLAST GROWTH FACTOR 21 (FGF21) GENE THERAPY

(71) Applicant: Universitat Autonoma de Barcelona, Cerdanyola del Valles (ES)

(72) Inventors: Maria Fàtima Bosch Tubert, Cerdanyola del Valles (ES); Verónica Jiménez Cenzano, Sabadell (ES); Ivet Elias Puigdomènech, Matadepera (ES); Albert Ribera Sánchez, Santa Eulàlia ed Ronçana (ES); Ignasi Grass Costa, Sabadell (ES)

(73) Assignee: Universitat Autónoma de Barcelona, Cerdanyola del Valles (ES)

( * ) Notice: Subject to any disclaimer, the term of this patent is extended or adjusted under 35 U.S.C. 154(b) by 1206 days.

(21) Appl. No.: 17/295,453

(22) PCT Filed: Nov. 26, 2019

(86) PCT No.: PCT/EP2019/082601

§ 371 (c)(1),
(2) Date: May 20, 2021

(87) PCT Pub. No.: WO2020/109314

PCT Pub. Date: Jun. 4, 2020

(65) Prior Publication Data

US 2021/0386870 A1 Dec. 16, 2021

(30) Foreign Application Priority Data

Nov. 26, 2018 (EP) .................................... 18382857

(51) Int. Cl.
| | |
|---|---|
| *A61K 48/00* | (2006.01) |
| *A61P 3/04* | (2006.01) |
| *A61P 3/10* | (2006.01) |

(52) U.S. Cl.
CPC ...... *A61K 48/0058* (2013.01); *A61K 48/0075* (2013.01); *A61P 3/04* (2018.01); *A61P 3/10* (2018.01)

(58) Field of Classification Search
None
See application file for complete search history.

(56) References Cited

U.S. PATENT DOCUMENTS

| | | | |
|---|---|---|---|
| 5,139,941 | A | 8/1992 | Muzyczka et al. |
| 5,741,683 | A | 4/1998 | Zhou et al. |
| 6,057,152 | A | 5/2000 | Samulski et al. |
| 6,165,782 | A | 12/2000 | Naldini et al. |
| 6,204,059 | B1 | 3/2001 | Samulski et al. |
| 6,207,455 | B1 | 3/2001 | Chang |
| 6,218,181 | B1 | 4/2001 | Verma et al. |
| 6,268,213 | B1 | 7/2001 | Samulski et al. |
| 6,277,633 | B1 | 8/2001 | Olsen et al. |
| 6,323,031 | B1 | 11/2001 | Cichutek |
| 6,491,907 | B1 | 12/2002 | Rabinowitz et al. |
| 6,531,456 | B1 | 3/2003 | Kurtzman et al. |
| 6,660,514 | B1 | 12/2003 | Zolotukhin et al. |
| 6,951,753 | B2 | 10/2005 | Shenk et al. |
| 7,094,604 | B2 | 8/2006 | Snyder et al. |
| 7,172,893 | B2 | 2/2007 | Rabinowitz et al. |
| 7,201,898 | B2 | 4/2007 | Monahan et al. |
| 7,229,823 | B2 | 6/2007 | Samulski et al. |
| 7,439,065 | B2 | 10/2008 | Ferrari et al. |
| 9,023,791 | B2 | 5/2015 | Boettcher et al. |
| 9,079,971 | B2 | 7/2015 | Cujec et al. |
| 9,464,126 | B2 | 10/2016 | Mohammadi et al. |
| 2014/0134352 | A1 | 5/2014 | Kim et al. |
| 2018/0186849 | A1 | 7/2018 | Mohammadi et al. |

FOREIGN PATENT DOCUMENTS

| | | | |
|---|---|---|---|
| CN | 106220724 | A | 12/2016 |
| CN | 106397607 | A | 2/2017 |
| CN | 106432509 | A | 2/2017 |
| EP | 2394667 | A1 | 12/2011 |
| EP | 2492347 | A1 | 8/2012 |
| EP | 3101125 | A1 | 12/2016 |
| EP | 3887393 | A1 | 10/2021 |
| JP | 2013-523164 | A | 6/2013 |
| JP | 2016530246 | A | 9/2016 |
| JP | 2017518271 | A | 7/2017 |
| JP | 2018-526988 | A | 9/2018 |
| WO | 02/24234 | A2 | 3/2002 |
| WO | WO2009120978 | A2 | 10/2009 |
| WO | WO2009149171 | A2 | 12/2009 |
| WO | WO2010139741 | A1 | 12/2010 |
| WO | WO2011/127337 | A2 | 10/2011 |
| WO | 2011154520 | A1 | 12/2011 |
| WO | 2012/007458 | A1 | 1/2012 |

(Continued)

OTHER PUBLICATIONS

Hinderer et al., Molecular Therapy—Methods & Clinical Development (2014) 1, 14051 (9 pages) (Year: 2014).*
Zhou et al., Scientific Reports, 7:5432, 13 pages (Year: 2017).*
Kuznik, B.I., et al. "Growth Factors of Fibroblasts FGF19, FGF21, FGF23 as Endocrine regulators of Physiological Functions and Geroprotectors. Epigenetic Regulatory Mechanisms," Uspehi Sovremennoj Biologii (Advances In Modern Biology) 137(1):84-99, Russian Academy of Sciences, Russia (2017).
Jimenez, Veronica, et al. "FGF21 gene therapy as treatment for obesity and insulin resistance." EMBO molecular medicine 10.8 (2018): e8791.
Sarruf, David A., et al. "Fibroblast growth factor 21 action in the brain increases energy expenditure and insulin sensitivity in obese rats." Diabetes 59.7 (2010): 1817-1824.

(Continued)

*Primary Examiner* — Evelyn Y Pyla
(74) *Attorney, Agent, or Firm* — Sterne, Kessler, Goldstein & Fox P.L.L.C.

(57) ABSTRACT

Described herein is a gene construct comprising a nucleotide sequence encoding a fibroblast growth factor 21 (FGF21), for use in the treatment and/or prevention of a metabolic disorder, wherein the therapy involves expression of the gene construct in the central nervous system (CNS).

18 Claims, 19 Drawing Sheets

Specification includes a Sequence Listing.

(56) References Cited

FOREIGN PATENT DOCUMENTS

| WO | 2013/006486 A2 | 1/2013 |
| WO | 2013/033452 A2 | 3/2013 |
| WO | 2014/020149 A1 | 2/2014 |
| WO | 2014/085365 A2 | 6/2014 |
| WO | WO-2015013148 A2 | 1/2015 |
| WO | 2015/044292 A1 | 4/2015 |
| WO | 2015/173308 A1 | 11/2015 |
| WO | WO-2015168666 A2 | 11/2015 |
| WO | 2016/041588 A1 | 3/2016 |
| WO | 2016/087678 A1 | 6/2016 |
| WO | 2016/110518 A1 | 7/2016 |
| WO | 2016/193431 A1 | 12/2016 |
| WO | WO2017/021893 A1 | 2/2017 |
| WO | WO-2017136202 A1 | 8/2017 |
| WO | WO2017/201527 A2 | 11/2017 |
| WO | 2018/060097 A1 | 4/2018 |
| WO | 2018/215613 A1 | 11/2018 |
| WO | WO-2019183183 A1 | 9/2019 |
| WO | WO-2020109314 A1 | 6/2020 |
| WO | WO-2021239815 A1 | 12/2021 |

OTHER PUBLICATIONS

Koichi Miyake et al., (Journal of The Medical Association of Nippon Medical School), 2012, vol. 8, pp. 216-221; Translation of abstract included.

Translation of Office Action issued by JPO on Mar. 22, 2022 wherein Koichi Miyake et al was cited.

Coskun et al., "Fibroblast Growth Factor 21 Corrects Obesity in Mice", Endocrinology, Dec. 2008, 149 (12):6018-6027, doi: 10.1210/en.2008-0816.

Fisher et al., "FGF21 regulates PGC-1a and browning of white adipose tissues in adaptive thermogenesis", Genes & Development 26:271-281, 2012 by Cold Spring Harbor Laboratory Press, ISSN 0890-9369/12; www.genesdev.org.

Kharitonenkov et al., "FGF-21 as a novel metabolic regulator", The Journal of Clinical Investigation, http://www.jci.org, vol. 115, No. 6, J. Clin. Invest. 115:1627-1635 (2005). doi:10.1172/JCI23606.

Ng et al., "miRNA-32 Drives Brown Fat Thermogenesis and Trans-activates Subcutaneous White Fat Browning in Mice", Cell Rep. May 9, 2017; 19(6): 1229-1246. doi:10.1016/j.celrep.2017.04.035.

Zhang et al., "Chronic Over-expression of Fibroblast Growth Factor 21 Increases Bile Acid Biosynthesis by Opposing FGF15/19 Action", EBioMedicine 15 (2017) 173-183.

Altschul, S.F., et al., "Basic Local Alignment Search Tool," J Mol Biol 215(3):403-10, Elsevier, Netherlands (Oct. 1990).

Altschul, S.F., et al., "Gapped BLAST and PSI-BLAST: A New Generation of Protein Database Search Programs," Nucleic Acids Res. 25(17):3389-3402, Oxford University Press, United Kingdom (Sep. 1997).

Amado, R.G., and Chen, I.S., "Lentiviral Vectors—The Promise of Gene Therapy Within Reach?," Science 285:674-76, American Association for the Advancement of Science, United States (Jul. 1999).

Anderson, W.F., "Human Gene Therapy," Nature 392:25-30, Springer, Germany (Apr. 1998).

Apparailly, F., et al., "Adeno-Associated Virus Pseudotype 5 Vector Improves Gene Transfer in Arthritic Joints," Hum. Gene Ther. 16(4):426-434, Mary Ann Liebert, Inc., United States (2005).

Ayuso, E., et al., "Production, Purification and Characterization of Adeno-Associated Vectors," Curr. Gene Ther. 10(6):423-436, Bentham Science, United Arab Emirates (2010).

Beilharz, J.E., et al., "Short-Term Exposure to a Diet High in Fat and Sugar, or Liquid Sugar, Selectively Impairs Hippocampal-Dependent Memory, with Differential Impacts on Inflammation," Behav Brain Res 306:1-7, Elsevier, Netherlands (Jun. 2016).

Bookout, A.L., et al., "FGF21 Regulates Metabolism and Circadian Behavior by Acting on the Nervous System," Nat Med 19(9):1147-52, Springer, Germany (Sep. 2013).

Buchlis, G., et al., "Factor IX Expression in Skeletal Muscle of a Severe Hemophilia B Patient 10 Years after AAV-Mediated Gene Transfer," Blood. 29:119(13):3038-41, American Society of Hematology, United States (Mar. 2012).

Chiorini, J.A., et al., "Cloning and Characterization of Adeno-Associated Virus Type 5," J. Virol. 73(2):1309-1319, American Society for Microbiology, United States (1999).

Douris, N., et al., "Central Fibroblast Growth Factor 21 Browns White Fat via Sympathetic Action in Male Mice," Endocrinology 156(7):2470-81, Oxford University Press, United Kingdom (Jul. 2015).

Federico, M., "Lentiviruses as Gene Delivery Vectors," Curr. Opin. Biotechnol. 10(5):448-453, Elsevier, Netherlands (1999).

Fisher, F.M., et al., "FGF21 Regulates PGC-1α and Browning of White Adipose Tissues in Adaptive Thermogenesis," Genes Dev 26(3):271-81, Cold Spring Harbor Laboratory Press, United States (Feb. 2012).

Gaich, G., et al., "The Effects of LY2405319, an FGF21 Analog, in Obese Human Subjects with Type 2 Diabetes," Cell Metab 18(3):333-40, Cell Press, United States (Sep. 2013).

Goncalves, M.A., "Adeno-Associated Virus: From Defective Virus to Effective Vector," Virol. J. 2(1):43, BMC, United Kingdom (2005).

Guillemot-Legris, O. & Muccioli, G.G., "Obesity-Induced Neuroinflammation: Beyond the Hypothalamus," Trends Neurosci 40(4):237-253, Elsevier, Netherlands (Apr. 2017).

Haslam, D.W. & James, W.P.T., "Obesity," Lancet 366(9492):1197-209, Elsevier, Netherlands (Oct. 2005).

Henikoff, S. & Henikoff, J.G., "Amino Acid Substitution Matrices from Protein Blocks," Proc Natl Acad Sci 89(22):10915-19, National Academy of Sciences, United States (Nov. 1992).

Hotamisligil, G.S., "Inflammation, Metaflammation, and Immunometabolic Disorders," Nature 542(7640):177-185, Springer, Germany (Feb. 2017).

Huang, J., et al., "Development of a Novel Long-Acting Antidiabetic FGF21 Mimetic by Targeted Conjugation to a Scaffold Antibody," J Pharmacol Exp Ther 346(2):270-80, American Society for Pharmacology and Experimental Therapeutics, United States (Aug. 2013).

Kay, M.A., et al., "Viral Vectors for Gene Therapy: The Art of Turning Infectious Agents into Vehicles of Therapeutics," Nat. Med. 7:33-40, Springer, Germany (Jan. 2001).

Konishi, M., et al., "Fibroblast Growth Factor-16 Is a Growth Factor for Embryonic Brown Adipocytes," J Biol Chem 275(16):12119-122, American Society for Biochemistry and Molecular Biology, United States (Apr. 2000).

Kunkel, T.A., et al., "Rapid and Efficient Site-Specific Mutagenesis without Phenotypic Selection," Proc Natl Acad Sci 82(2):488-92, National Academy of Sciences, United States (Jan. 1985).

Lock, M., et al., "Characterization of a Recombinant Adeno-Associated Virus Type 2 Reference Standard Material," Hum. Gene Ther. 21(10):1273-1285, Mary Ann Liebert, Inc., United States (Oct. 2010).

Mandel, R.J., et al., "Clinical Trials in Neurological Disorders Using AAV Vectors: Promises and Challenges," Curr Opin Mol Ther. 6(5):482-90, Thomson Reuters Corporation, Canada (Oct. 2004).

Marin, M., et al., "Towards Efficient Cell Targeting by Recombinant Retroviruses," Mol. Med. Today 3:396-403, Elsevier, Netherlands (Sep. 1997).

Martin, K.R.G. & Quigley, H.A., "Gene Therapy for Optic Nerve Disease," Eye 18(11):1049-1055, United Kingdom (Nov. 2004).

Metzger, D., et al., "The Human Oestrogen Receptor Functions in Yeast," Nature 334:31-36, Nature Publishing Group, United Kingdom (Jul. 1988).

Moller, D.E. & Flier, M.D., "Insulin Resistance—Mechanisms, Syndromes, and Implications," N Engl J Med 325(13):938-48, Massachusetts Medical Society, United States (Sep. 1991).

Muise, E.S., et al., "Adipose Fibroblast Growth Factor 21 Is Up-Regulated by Peroxisome Proliferator-Activated Receptor Gamma and Altered Metabolic States," Mol Pharmacol 74(2):403-12, American Society for Pharmacology and Experimental Therapeutics, United States (Aug. 2008).

(56)     References Cited

OTHER PUBLICATIONS

Nathwani, A.C., et al., "Adenovirus-Associated Virus Vector-Mediated Gene Transfer in Hemophilia B," N. Engl. J. Med. 365(25):2357-2365, Massachusetts Medical Society, United States (Dec. 2011).

Niemeyer, G.P., et al., "Long-Term Correction of Inhibitor-Prone Hemophilia B Dogs Treated with Liver-Directed AAV2-Mediated Factor IX Gene Therapy," Blood 113(4):797-806, American Society of Hematology, United States (Jan. 2009).

Okada, T., et al., "Scalable Purification of Adeno-Associated Virus Serotype 1 (AAV1) and AAV8 Vectors, Using Dual Ion-Exchange Adsorptive Membranes," Hum. Gene Ther. 20:1013-1021, Mary Ann Liebert, Inc., United States (Sep. 2009).

Owen, B.M., et al., "FGF21 Acts Centrally to Induce Sympathetic Nerve Activity, Energy Expenditure, and Weight Loss," Cell Metab 20(4):670-77, Cell Press, United States (Oct. 2014).

Peeters, A., et al., "Obesity in Adulthood and Its Consequences for Life Expectancy: A Life-Table Analysis," Ann Intern Med 138(1):24-32, American College of Physicians, United States (Jan. 2003).

Peng, K-W. & Russell, S.J., "Viral Vector Targeting," Curr. Opin. Biotechnol. 10:454-57, Elsevier, Netherlands (Oct. 1999).

Pfaffl, M., "A New Mathematical Model for Relative Quantification in Real-Time RT-PCR," Nucleic Acids Res. 29(9):e45, Oxford University Press, United Kingdom (May 2001).

Reiser, J., "Production and Concentration of Pseudotyped HIV-1-Based Gene Transfer Vectors," Gene Ther. 7:910-13, Springer, Germany (Jun. 2000).

Roberts, S., et al., "Generation of an Antibody with Enhanced Affinity and Specificity for Its Antigen by Protein Engineering," Nature 328:731-734, Nature Publishing Group, United Kingdom (Aug. 1987).

Roberts, D.L., et al., "Biological Mechanisms Linking Obesity and Cancer Risk: New Perspectives," Annu Rev Med 61:301-16, Annual Reviews, United States (2010).

Russell, W.C., "Update on Adenovirus and Its Vectors," J. Gene Virol. 81:2573-2604, Microbiology Society, United Kingdom (Nov. 2000).

So, W.Y. & Leung P.S., "Fibroblast Growth Factor 21 As an Emerging Therapeutic Target for Type 2 Diabetes Mellitus," Med Res Rev 36(4):672-704, Wiley, United States (Jul. 2016).

Sommerfelt, M.A., "Retrovirus Receptors," J. Gen. Virol. 80:3049-64, Microbiology Society, United Kingdom (Dec. 1999).

Tomlinson, E., et al., "Transgenic Mice Expressing Human Fibroblast Growth Factor-19 Display Increased Metabolic Rate and Decreased Adiposity," Endocrinology 143(5):1741-47, Oxford University Press, United Kingdom (May 2002).

Valdearcos, M., et al., "Hypothalamic Inflammation in the Control of Metabolic Function," Annu Rev Physiol 77:131-60, Annual Reviews, United States (Feb. 2015).

Vigna, E., et al., "Lentiviral Vectors: Excellent Tools for Experimental Gene Transfer and Promising Candidates for Gene Therapy," J. Gene Med. 2:308-316, Wiley, United States (Sep. 2000).

Virag, T., et al., "Producing Recombinant Adeno-Associated Virus in Foster Cells: Overcoming Production Limitations Using a Baculovirus-Insect Cell Expression Strategy," Hum. Gene Ther. 20:807-817, Mary Ann Liebert, Inc., United States (Aug. 2009).

Walther, W., and Stein, U., "Viral Vectors for Gene Transfer: A Review of Their Use in the Treatment of Human Diseases," Drugs 60:249-71, Springer, Germany (Aug. 2000).

Wang, C.Y., et al., "Improved Neuronal Transgene Expression from an AAV-2 Vector with a Hybrid CMV Enhancer/PDGF-Promoter," J. Gene Med. 7:945-955, Wiley, United States (Jul. 2005).

Wells, J.A., et al., "Cassette Mutagenesis: An Efficient Method for Generation of Multiple Mutations at Defined Sites," Gene 34:315-323, Elsevier, Netherlands (1985).

Xu, J., et al., "Fibroblast Growth Factor 21 Reverses Hepatic Steatosis, Increases Energy Expenditure, and Improves Insulin Sensitivity in Diet-Induced Obese Mice," Diabetes 58(1):250-59, American Diabetes Association, United States (Jan. 2009).

Zhang, H., et al., "Adenovirus-Adeno-Associated Virus Hybrid for Large-Scale Recombinant Adeno-Associated Virus Production," Hum. Gene Ther. 20:922-929, Mary Ann Liebert, Inc., United States (Sep. 2009).

Zhang, J. & Li, Y., "Fibroblast Growth Factor 21 Analogs for Treating Metabolic Disorders," Front Endocrinol (Lausanne) 6:168, Frontiers Media, Switzerland (Nov. 2015).

International Search Report and Written Opinion for International Application No. PCT/EP2019/082601, European Patent Office, Netherlands, mailed on Jan. 8, 2020, 12 pages.

Carter, P.J. & Samulski, R.J., "Adeno-Associated Viral Vectors as Gene Delivery Vehicles," Int J Mol Med. 6(1):17-27, Spandidos Publications, Greece (Jul. 2000).

Casellas, A., et al., "Expression of IGF-I in Pancreatic Islets Prevents Lymphocytic Infiltration and Protects Mice from Type 1 Diabetes," Diabetes 55(12):3246-55, American Diabetes Association, United States (Dec. 2006).

Gao, G., et al., "Clades of Adeno-Associated Viruses Are Widely Disseminated in Human Tissues," J Virol. 78(12):6381-8, American Society for Microbiology, United States (Jun. 2004).

Konishi, M., et al., "Secreted Factor, FG21, Regulates Diverse Biological Processes," Journal of Japanese Biochemical Society 88(1): 86-93, The Japanese Biochemical Society, Japan (Feb. 2016).

Carr, R.M., et al., "Absence of Perilipin 2 Prevents Hepatic Steatosis, Glucose Intolerance and Ceramide Accumulation in Alcohol-Fed Mice," PLoS One 9(5):e97118, PLOS, United States (May 2014).

Ayuso, E., and Bosch, F., "Highlights on AAV Mediated Gene Transfer: Introduction," in The Clinibook: Clinical Gene Transfer State of the Art, Cohen-Haguenauer, O., ed., pp. 31-34, Editions EDK, Paris, France (2012).

Ayuso, E., et al., "AAV Gene Therapy for Diabetes Mellitus," in The Clinibook: Clinical Gene Transfer State of the Art, Cohen-Haguenauer, O., ed., pp. 62-70, Editions EDK, Paris, France (2012).

Ayuso, E., et al., "High AAV vector purity results in serotype- and tissue-independent enhancement of transduction efficiency," Gene Ther 17(4):503-510, Nature Publishing Group, United Kingdom (Apr. 2010).

Ayuso, E., et al., "Reference Materials for the Characterization of Adeno-Associated Viral Vectos," in The Clinibook: Clinical Gene Transfer State of the Art, Cohen-Haguenauer, O., ed., pp. 83-90, Editions EDK, Paris, France (2012).

Casana, E., et al., "AAV-mediated BMP7 gene therapy counteracts insulin resistance and obesity," Mol Ther Methods Clin Dev 25:190-204, Cell Press, United States (Mar. 2022).

Casana, E., et al., "BMP7 overexpression in adipose tissue induces white adipogenesis and improves insulin sensitivity in ob/ob mice," Int J Obes (Lond) 45(2):449-460, Nature Publishing Group, United Kingdom (Feb. 2021).

Garcia, M., et al., "Phosphofructo-1-kinase deficiency leads to a severe cardiac and hematological disorder in addition to skeletal muscle glycogenosis," PLoS Genet 5(8):e1000615, Public Library of Science, United States (Aug. 2009), 12 pages.

Gros, L., et al., "Insulin production by engineered muscle cells," Hum Gene Ther 10(7):1207-1217, Mary Ann Liebert Inc., United States (May 1999).

Haurigot, V., et al., "Future Directions: Gene Therapy for Diabetes," in Textbook of Diabetes, Holt, R., ed., pp. 1029-1037, Wiley-Blackwell, United States (2017).

Haurigot, V., et al., "Increased intraocular insulin-like growth factor-I triggers blood-retinal barrier breakdown," J Biol Chem 284(34):22961-22969, American Society for Biochemistry and Molecular Biology Inc., United States (Aug. 2009).

Haurigot, V., et al., "Long-term retinal PEDF overexpression prevents neovascularization in a murine adult model of retinopathy," PLoS One 7(7):e41511, Public Library of Science, United States (2012), 12 pages.

Jimenez, V., et al., "In vivo adeno-associated viral vector-mediated genetic engineering of white and brown adipose tissue in adult mice," Diabetes 62(12):4012-4022, American Diabetes Association Inc., United States (Dec. 2013).

Mann, C.J., et al., "Molecular signature of the immune and tissue response to non-coding plasmid DNA in skeletal muscle after

(56) References Cited

OTHER PUBLICATIONS electrotransfer," Gene Ther 19(12):1177-1186, Nature Publishing Group, United Kingdom (Dec. 2012).

Mann, C.J., et al., "Skeletal muscle metabolism in the pathology and treatment of type 1 diabetes," Curr Pharm Des 16(8):1002-1020, Bentham Science Publishers B.V., United Arab Emirates (2010).

Marco, S., et al., "In Vivo Gene Therapy for Mucopolysaccharidosis Type III (Sanfilippo Syndrome): A New Treatment Horizon," Hum Gene Ther 30(10):1211-1221, Mary Ann Liebert Inc., United States (Oct. 2019).

Munoz, S., et al., "Treatment of infantile-onset Pompe disease in a rat model with muscle-directed AAV gene therapy," Mol Metab 81:101899, Elsevier GmbH, Germany (Mar. 2024), 17 pages.

Otaegui, P.J., et al., "Expression of glucokinase in skeletal muscle: a new approach to counteract diabetic hyperglycemia," Hum Gene Ther 11(11):1543-1552, Mary Ann Liebert Inc., United States (Jul. 2000).

Otaegui, P.J., et al., "Glucose-regulated glucose uptake by transplanted muscle cells expressing glucokinase counteracts diabetic hyperglycemia," Hum Gene Ther 13(18):2125-2133, Mary Ann Liebert Inc., United States (Dec. 2002).

Riu, E., et al., "Counteraction of type 1 diabetic alterations by engineering skeletal muscle to produce insulin: insights from transgenic mice," Diabetes 51(3):704-711, American Diabetes Association Inc., United States (Mar. 2002).

Roca, C., et al., "Disease correction by AAV-mediated gene therapy in a new mouse model of mucopolysaccharidosis type IIID," Hum Mol Genet 26(8):1535-1551, Oxford University Press, United Kingdom (Apr. 2017).

Ruberte, J., et al., "Increased ocular levels of IGF-1 in transgenic mice lead to diabetes-like eye disease," J Clin Invest 113(8):1149-1157, The American Society for Clinical Investigation, United States (Apr. 2004).

Vila, L., et al., "AAV8-mediated Sirt1 gene transfer to the liver prevents high carbohydrate diet- induced nonalcoholic fatty liver disease," Mol Ther Methods Clin Dev 1:14039, Cell Press, United States (Oct. 2014), 10 pages.

Villacampa, P., et al., "Insulin-like growth factor I (IGF-I)-induced chronic gliosis and retinal stress lead to neurodegeneration in a mouse model of retinopathy," J Biol Chem 288(24):17631-17642, American Society for Biochemistry and Molecular Biology Inc., United States (Jun. 2013).

Villacampa, P., et al., "Proliferative retinopathies: animal models and therapeutic opportunities," Curr Neurovasc Res 12(2):189-198, Bentham Science Publishers B.V., United Arab Emirates (2015).

Vila, L., et al., "AAV-mediated Sirt1 overexpression in skeletal muscle activates oxidative capacity but does not prevent insulin resistance," Mol Ther Methods Clin Dev 5:16072, Cell Press, United States (Nov. 2016).

Callejas, D., et al., "Treatment of diabetes and long-term survival after insulin and glucokinase gene therapy," Diabetes 62(5):1718-1729, American Diabetes Association Inc., United States (May 2013).

Jaen, M.L., et al., "Long-Term Efficacy and Safety of Insulin and Glucokinase Gene Therapy for Diabetes: 8-Year Follow-Up in Dogs," Mol Ther Methods Clin Dev 6:1-7, Cell Press, United States (Sep. 2017).

Mas, A., et al., "Reversal of type 1 diabetes by engineering a glucose sensor in skeletal muscle," Diabetes 55(6):1546-1553, American Diabetes Association Inc., United States (Jun. 2006).

Marco, S., et al., "Seven-year follow-up of durability and safety of AAV CNS gene therapy for a lysosomal storage disorder in a large animal," Mol Ther Methods Clin Dev 23:370-389, Cell Press, United States (Oct. 2021).

Motas, S., et al., "CNS-directed gene therapy for the treatment of neurologic and somatic mucopolysaccharidosis type II (Hunter syndrome)," JCI Insight 1(9):e86696, American Society for Clinical Investigation (ASCI), United States (Jun. 2016).

Haurigot, V., et al., "Whole body correction of mucopolysaccharidosis IIIA by intracerebrospinal fluid gene therapy," J Clin Invest. 123(8):3254-3271, American Society for Clinical Investigation, United States (Aug. 2013).

Haurigot, V., et al., "Toward a gene therapy for neurological and somatic MPSIIIA," Rare Dis 1:e27209, Taylor and Francis, United Kingdom (Dec. 2013).

Ribera, A., et al., "Biochemical, histological and functional correction of mucopolysaccharidosis type IIIB by intra-cerebrospinal fluid gene therapy," Hum Mol Genet 24(7):2078-95, Oxford University Press, United Kingdom (Apr. 2015).

"Abstracts of 17th Annual Meeting of the American-Society-of-Geneand-Cell-Therapy (ASGCT)," Molecular Therapy, vol. 22, No. Suppl. 1., Jun. 1, 2014 (Jun. 1, 2014), pp. S1-S306.

Inagaki, Takeshi, et al. "Endocrine regulation of the fasting response by PPARα-mediated induction of fibroblast growth factor 21." Cell metabolism 5.6 (2007): 415-425.

Huang, Xinqiang, et al. "Forced expression of hepatocyte-specific fibroblast growth factor 21 delays initiation of chemically induced hepatocarcinogenesis." Molecular Carcinogenesis: Published in cooperation with the University of Texas MD Anderson Cancer Center 45.12 (2006): 934-942.

Geisler, A., and Fechner, H., "MicroRNA-regulated viral vectors for gene therapy," World Journal of Experimental Medicine 6(2):37-54, Baishideng Publishing Group, United States (May 2016).

Lin., X. et al., "Metabolic role of fibroblast growth factor 21 in liver, adipose and nervous system tissues (Review), " Biomedical Reports 6:495-502, Spandidos Publications, United Kingdom (2017).

Gooderham, M.J., et al., "Shifting the focus—the primary role of IL-23 in psoriasis and other inflammatory disorders," Journal of the European Academy of Dermatology and Venereology 32:1111-1119, John Wiley & Sons Ltd., United States (2018).

Baylot, V., et al., "TCTP Has a Crucial Role in the Different Stages of Prostate Cancer Malignant Progression," In: Telerman, A., Amson, R. (eds) TCTP/tpt1—Signaling from Stem Cell to Disease. Results and Problems in Cell Differentiation, 64:255-261 Springer, Cham., (2017).

Muller, S., et al., "Spliceosomal peptide P140 for immunotherapy of systemic lupus erythematosus: results of an early phase II clinical trial," *Arthritis Rheum.* 58(12):3873-3883, Wiley, United States (Dec. 2008).

Pakula, A. A. and Sauer, R. T., "Genetic analysis of protein stability and function," *Anna. Rev. Genet* 23:289-310, Annual Reviews, United States (Jan. 1989).

* cited by examiner

*moFgf21* Expression

FIG. 3

□Non-treated
▨AAV1-CAG-moFGF21-dmirtT
▩AAV2-CAG-moFGF21-dmirtT
■AAV9-CAG-moFGF21-dmirtT

*moFGF21* Expression non-treated            AAV9-CAG-moFGF21-dmiRT non-treated            AAV9-CAG-moFGF21-dmiRT

MAC-2 non-treated          AAV9-CAG-moFGF21-dmiRT

□ non-treated
■ AAV9-CAG-moFGF21-dmiRT

FIBROBLAST GROWTH FACTOR 21 (FGF21) GENE THERAPY

BACKGROUND

The prevalence of diabetes is growing at an alarming rate and is a major health problem worldwide. Obesity is strongly associated with insulin resistance and type 2 diabetes (T2D) (Moller, D. E., and Flier, J. S., 1991. N. Engl. J. Med. 325:938-948). Both T2D and obesity increase the risk of mortality (Peeters, A. et al., 2003. Ann. Intern. Med. 138:24-32) and also increase the risk of highly morbid chronic diseases, including cardiovascular disease, hypertension and certain types of cancers (Haslam, D. W. et al., 2005, Lancet. 366, 1197-1209; Roberts, D. L. et al., 2010, Annu. Rev. Med. 61, 301-316). Insulin resistance and obesity-associated diseases are subsequently linked to reduced life expectancy and poor quality of life.

It is now well-accepted that during obesity there is a chronic, low-grade, inflammation in peripheral tissues, such as adipose tissue, liver, or skeletal muscle that may be responsible for metabolic dysfunction, including the development of insulin resistance (Valdearcos, M. et al., 2015, Annu. Rev. Physiol. 77, 131-160; Hotamisligil, G. S. et al., 2017, Nature. 542, 177-185). Recently, a growing body of literature has demonstrated that obesity and insulin resistance are also associated with inflammation in the brain (Guillemot-Legris, O. et al., 2017, Trends Neurosci. 40, 237-253; Beilharz, J. E. et al., 2016, Behav. Brain Res. 306, 1-7). Moreover, obesity and insulin resistance are not only linked to neuroinflammation but also with deficits in cognitive function in animal models and humans (Guillemot-Legris, O. et al., 2017, Trends Neurosci. 40, 237-253).

Fibroblast growth factor 21 (FGF21), a growth factor predominantly secreted by the liver, but also by adipose tissue and pancreas (Muise, E. S. et al., 2008. Mol. Pharmacol. 74:403-412), has been shown to increase brown adipose tissue (BAT) growth and expression of thermogenic genes in BAT and white adipose tissue (WAT), stimulating energy expenditure (Coskun, T. et al., 2008. Endocrinology 149:6018-6027; Fisher, F. M. et al., 2012. Genes Dev. 26:271-281; Kharitonenkov, A. et al., 2005. J. Clin. Invest 115:1627-1635; Konishi, M. et al., 2000. J. Biol. Chem. 275:12119-12122; Tomlinson, E. et al., 2002. Endocrinology 143:1741-1747; Xu, J. et al., 2009. Diabetes 58:250-259).

Native FGF21 protein exhibits poor pharmacokinetic characteristics. It has a short half-life, and it is susceptible to in vivo proteolytic degradation and in vitro aggregation (Huang, J. et al., 2013. *J Pharmacol Exp Ther.* 346(2):270-80; So, W. Y. and Leung, P. S. 2016. Med Res Rev. 36(4):672-704; Zhang, J. and Li, Y. 2015. *Front Endocrinol (Lausanne).* 6:168). Various engineering approaches have been developed to extend the half-life and to improve the stability and solubility of FGF21. Currently, two engineered FGF21 mimetics (LY2405319 and PF-05231023) are being tested in humans. Nevertheless, those FGF21 mimetics require multiple administrations, which poses a significant burden to the patients. Moreover, engineered FGF21 mimetics/analogs may exhibit a higher risk of immunogenicity than native FGF21, e.g. patients treated with LY2405319 developed injection site reactions, anti-drug antibodies and a serious hypersensitivity reaction (Gaich, G. et al., 2013. *Cell Metab.* 18(3):333-40). Thus, the long-term and effective expression provided by a single administration of the vectors of the invention represents a significant advantage over other therapies.

Given the importance that neuroinflammation seems to play in the cognitive decline and whole-body energy and glucose metabolism observed in diabetes and obesity, new therapeutic approaches addressing the inflammation of the central nervous system (CNS) may be of compelling importance. Recent studies have shown that FGF21 peripheral metabolic effects may indeed be mediated by FGF21 signalling in the CNS, particularly in the hypothalamus, which is the major site of the brain regulating whole-body energy metabolism (D. A. Sarruf et al., *Diabetes.* 59, 1817-1824 (2010); A. L. Bookout et al., *Nat. Med.* 19, 1147-1152 (2013); B. M. Owen et al., *Cell Metab.* 20, 670-677 (2014); N. Douris et al., *Endocrinology.* 156, 2470-2481 (2015).

FIELD

Aspects herein pertain to the medical field, comprising gene therapy compositions for use in the treatment of a metabolic disorder in mammals, particularly in human beings.

SUMMARY

In a first aspect, there is provided a gene construct comprising a nucleotide sequence encoding a fibroblast growth factor 21 (FGF21), for use in therapy, wherein the therapy involves expression of the gene construct in the central nervous system (CNS), preferably in the brain, more preferably in the hypothalamus. In some embodiments, there is provided a gene construct comprising a nucleotide sequence encoding a fibroblast growth factor 21 (FGF21), for use in the treatment of a metabolic disorder, wherein the therapy involves expression of the gene construct in the central nervous system (CNS), preferably in the brain, more preferably in the hypothalamus and/or the cortex and/or the hippocampus and/or the cerebellum and/or the olfactory bulb, most preferably in the hypothalamus.

Preferably, the nucleotide sequence encoding FGF21 is operably linked to a ubiquitous promoter. In a preferred embodiment, the ubiquitous promoter is selected from the group consisting of a CAG promoter and a CMV promoter, preferably wherein the ubiquitous promoter is a CAG promoter. Preferably, the nucleotide sequence encoding FGF21 is operably linked to a ubiquitous promoter and at least one target sequence of a microRNA expressed in a tissue where the expression of FGF21 is wanted to be prevented.

Preferably, the at least one target sequence of a microRNA is selected from those target sequences that bind to microRNAs expressed in the heart and/or the liver of a mammal.

More preferably, the nucleotide sequence encoding FGF21 is operably linked to a ubiquitous promoter and at least one target sequence of a microRNA expressed in the liver and at least one target sequence of a microRNA expressed in the heart.

Preferably, a target sequence of a microRNA expressed in the heart is selected from SEQ ID NO's: 13 and 21-25 and a target sequence of a microRNA expressed in the liver is selected from SEQ ID NO's: 12 and 14-20.

More preferably, the gene construct comprises a target sequence of microRNA-122a and a target sequence of microRNA-1.

Preferably, the ubiquitous promoter is selected from the group consisting of a CAG promoter and a CMV promoter, preferably wherein the ubiquitous promoter is the CAG promoter.

Preferably, the nucleotide sequence encoding FGF21 is selected from the group consisting of:

(a) a nucleotide sequence encoding a polypeptide comprising an amino acid sequence that has at least 60% sequence identity with the amino acid sequence of SEQ ID NO: 1, 2 or 3;

(b) a nucleotide sequence that has at least 60% sequence identity with the nucleotide sequence of SEQ ID NO: 4, 5, 6, 7, 8, 9, 10 or 11; and (c) a nucleotide sequence the sequence of which differs from the sequence of a nucleotide sequence of (b) due to the degeneracy of the genetic code.

In a second aspect, there is provided an expression vector comprising a gene construct as described in the first aspect, for use in therapy, wherein the therapy involves expression of the gene construct in the CNS, preferably in the brain, more preferably in the hypothalamus. In some embodiments, there is provided an expression vector comprising a gene construct as described in the first aspect, for use in the treatment of a metabolic disorder, wherein the therapy involves expression of the gene construct in the CNS, preferably in the brain, more preferably in the hypothalamus and/or the cortex and/or the hippocampus and/or the cerebellum and/or the olfactory bulb, most preferably in the hypothalamus Preferably, the expression vector is a viral vector.

Preferably, the expression vector is selected from the group consisting of adenoviral vectors, adeno-associated viral vectors, retroviral vectors, and lentiviral vectors, preferably wherein the expression vector is an adeno-associated viral vector.

Preferably, the expression vector is an adeno-associated viral vector of serotype 1, 2, 3, 4, 5, 6, 7, 8, 9, rh10, rh8, Cb4, rh74, DJ, 2/5, 2/1, 1/2 or Anc80, more preferably wherein the expression vector is an adeno-associated viral vector of serotype 1, 2 or 9.

In a third aspect, there is provided a pharmaceutical composition comprising a gene construct as described in the first aspect and/or an expression vector as described in the second aspect, together with one or more pharmaceutically acceptable ingredients, for use in therapy, wherein the therapy involves expression of the gene construct in the CNS and/or the brain. In some embodiments, there is provided a pharmaceutical composition comprising a gene construct as described in the first aspect and/or an expression vector as described in the second aspect, together with one or more pharmaceutically acceptable ingredients, for use in the treatment of a metabolic disorder, wherein the therapy involves expression of the gene construct in the CNS, preferably in the brain, more preferably in the hypothalamus and/or the cortex and/or the hippocampus and/or the cerebellum and/or the olfactory bulb, most preferably in the hypothalamus.

In a fourth aspect, there is provided a gene construct for use as described in the first aspect and/or an expression vector for use as described in the second aspect and/or a pharmaceutical composition for use as described in the third aspect, wherein the gene construct and/or expression vector and/or pharmaceutical composition is administered by intra-CSF administration.

In a fifth aspect, there is provided a gene construct for use as described in the first aspect and/or an expression vector for use as described in the second aspect and/or a pharmaceutical composition for use as described in the third aspect, for use in the treatment and/or prevention of a metabolic disorder, preferably wherein the metabolic disorder is a diabetes and/or obesity.

DESCRIPTION

The present inventors have developed an improved gene therapy strategy based on FGF21 gene therapy directed to the central nervous system (CNS) to counteract obesity and/or diabetes. Particularly, as elaborated in the experimental part, the present inventors have found the following unexpected advantages of brain-directed FGF21 gene therapy:

The gene constructs and vectors as described herein can obtain a robust and wide-spread overexpression in the brain (Examples 1, 2, 3 and 4)

The gene constructs and vectors as described herein cause decreased adipocyte size, decreased fat accumulation in brown adipocytes, increased thermogenesis, reduced circulating triglycerides and free fatty acids, healthier pancreas (increase number of islet, amelioration of beta cell mass) and reduced systemic inflammation (reduction or pro-inflammatory cytokines such as F4/80, IL-6, TNFalpha) (Example 1.1).

In a widely used mouse model of obesity and diabetes, expression of FGF21 in the brain led to a clear reduction in weight gain, adiposity and liver weight as well as complete normalization of fed glycemia (Example 1), improved insulin resistance, improved glucose tolerance and decreased gluconeogenesis (Example 4)

In a widely used mouse model of senescence with age-related brain pathologies, expression of FGF21 in the brain led to a clear reduction in weight gain and liver weight (Example 2).

In both mouse models, inflammation of the hypothalamus is reduced (Examples 1, 2).

Accordingly, the aspects and embodiments of the present invention as described herein solve at least some of the problems and needs as discussed herein.

Gene Construct

In a first aspect, there is provided a gene construct comprising a nucleotide sequence encoding a fibroblast growth factor 21 (FGF21).

A "gene construct" as described herein has its customary and ordinary meaning as understood by one of skill in the art in view of this disclosure. A "gene construct" can also be called "expression cassette" or "expression construct" and refers to a gene or a group of genes, including a gene that encodes a protein of interest, which is operatively linked to a promoter that controls its expression. The part of this application entitled "general information" comprises more detail as to a "gene construct". "Operatively linked" as used herein is further described in the part of this application entitled "general information".

In some embodiments, a gene construct as described herein is suitable for expression in a mammal. As used herein, "suitable for expression in a mammal" may mean that the gene construct includes one or more regulatory sequences, selected on the basis of the mammalian host cells to be used for expression, that is operatively linked to the nucleotide sequence to be expressed. Preferably, said mammalian host cells to be used for expression are human, murine or canine cells.

In some embodiments, a gene construct as described herein is for use in therapy. In a preferred embodiment, a gene construct as described herein is for use in the treatment and/or prevention of a metabolic disorder. In a preferred embodiment, the therapy involves expression of the gene construct in the CNS, preferably in the brain, more preferably in the hypothalamus. In some embodiments, expression of the gene construct in the brain may mean expression of the gene construct in the hypothalamus and/or the cortex and/or the hippocampus and/or the cerebellum and/or the olfactory bulb, preferably the hypothalamus. Accordingly, expression of the gene construct in the brain may mean expression of the gene construct in at least one or at least two or at least three or all brain regions selected from the group consisting of the hypothalamus, the cortex, the hippocampus, the cerebellum and the olfactory bulb. In a preferred embodiment, the therapy involves expression of the gene construct in the hypothalamus. In some embodiments, expression in the CNS and/or the brain and/or the hypothalamus and/or the cortex and/or the hippocampus and/or the cerebellum and/or the olfactory bulb may mean specific expression in the CNS and/or the brain and/or the hypothalamus and/or the cortex and/or the hippocampus and/or the cerebellum and/or the olfactory bulb. In an embodiment, expression does not involve expression in the liver, pancreas, adipose tissue, skeletal muscle and/or heart. In some embodiments, expression does not involve expression in at least one, at least two, at least three, at least four or all organs selected from the group consisting of the liver, pancreas, adipose tissue, skeletal muscle and heart. A description of CNS- and/or brain- and/or hypothalamus and/or cortex- and/or hippocampus- and/or cerebellum- and/or olfactory bulb-specific expression has been provided under the section entitled "general information".

Expression may be assessed as described under the section entitled "general information". A description of "CNS", "brain" and "hypothalamus" has been provided under the section entitled "general information".

In some embodiments, a gene construct as described herein is for use in therapy, wherein the gene construct is administered by intra-CSF (cerebrospinal fluid) administration (via cisterna magna, intrathecal or intraventricular delivery), intraparenchymal administration or intranasal administration. A preferred administration is intra-CSF administration.

"Intra-CSF administration", "intranasal administration", "intraparenchymal administration" "intra-cisterna magna administration", "intrathecal administration" and "intraventricular administration", as used herein, are described in the part of this application entitled "general information".

In some embodiments, the gene construct as described herein comprises a nucleotide sequence encoding an FGF21 to be expressed in the CNS, preferably in the brain, more preferably in the hypothalamus. In some embodiments, the gene construct as described herein is suitable for expression in the CNS, preferably in the brain, more preferably in the hypothalamus. In some embodiments, expression of the gene construct in the brain may mean expression of the gene construct in the hypothalamus and/or the cortex and/or the hippocampus and/or the cerebellum and/or the olfactory bulb. Accordingly, expression of the gene construct in the brain may mean expression of the gene construct in at least one or at least two or at least three or all brain regions selected from the group consisting of the hypothalamus, the cortex, the hippocampus, the cerebellum and the olfactory bulb. Expression in the hypothalamus is most preferred. Expression may be assessed as described under the section entitled "general information".

In the context of embodiments of the invention, an FGF21 to be expressed in the CNS and/or the brain and/or the hypothalamus and/or the cortex and/or the hippocampus and/or the cerebellum and/or the olfactory bulb; and a gene construct suitable for expression in the CNS and/or the brain and/or the hypothalamus and/or the cortex and/or the hippocampus and/or the cerebellum and/or the olfactory bulb, refer to the preferential or predominant (at least 10% higher, at least 20% higher, at least 30% higher, at least 40% higher, at least 50% higher, at least 60% higher, at least 70% higher, at least 80% higher, at least 90% higher, at least 100% higher, at least 150% higher, at least 200% higher or more) expression of FGF21 in the CNS and/or the brain and/or the hypothalamus and/or the cortex and/or the hippocampus and/or the cerebellum and/or the olfactory bulb as compared to other organs or tissues. Other organs or tissues may be the liver, pancreas, adipose tissue, skeletal muscle, heart, kidney, colon, hematopoietic tissue, lung, ovary, spleen, stomach, testis and others. Preferably, other organs are the liver and/or the heart. In an embodiment, expression is not detectable in the liver, pancreas, adipose tissue, skeletal muscle and/or heart. In some embodiments, expression is not detectable in at least one, at least two, at least three, at least four or all organs selected from the group consisting of the liver, pancreas, adipose tissue, skeletal muscle, heart, kidney, colon, hematopoietic tissue, lung, ovary, spleen, stomach and testis. Expression may be assessed as described under the section entitled "general information".

A nucleotide sequence encoding an FGF21 present in a gene construct according to the invention may be derived from any FGF21 gene or FGF21 coding sequence, preferably an FGF21 gene or FGF21 coding sequence from human, mouse or dog; or a mutated FGF21 gene or FGF21 coding sequence, preferably from human, mouse or dog; or a codon optimized FGF21 gene or FGF21 coding sequence, preferably from human, mouse or dog.

Accordingly, in some embodiments, a preferred nucleotide sequence encoding an FGF21 encodes a polypeptide comprising an amino acid sequence that has at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity or similarity with SEQ ID NO: 1, 2 or 3. SEQ ID NO: 1 represents an amino acid sequence of human FGF21. SEQ ID NO: 2 represents an amino acid sequence of murine FGF21. SEQ ID NO: 3 represents an amino acid sequence of canine FGF21. In some embodiments, a nucleotide sequence encoding an FGF21 present in a gene construct according to the invention has at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity with any sequence selected from the group consisting of SEQ ID NO's: 4, 5, 6, 7, 8, 9, 10 or 11.

A description of "identity" or "sequence identity" and "similarity" or "sequence similarity" has been provided under the section entitled "general information".

In some embodiments, a nucleotide sequence encoding a human FGF21 present in a gene construct according to the invention has at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity with SEQ ID NO: 4, 5, 6 or 7. SEQ ID NO: 4 is a nucleotide sequence encoding human FGF21. SEQ ID NO: 5 is a codon optimized nucleotide sequence encoding human FGF21, variant 1. SEQ ID NO: 6 is a codon optimized nucleotide sequence encoding human FGF21, variant 2. SEQ ID NO: 7 is a codon optimized nucleotide sequence encoding human FGF21, variant 3. Variant 1, variant 2 and variant 3 encode for the same human FGF21 protein and were obtained by different algorithms of codon optimization. A description of "codon optimization" has been provided under the section entitled "general information".

In some embodiments, a nucleotide sequence encoding mouse FGF21 present in a gene construct according to the invention has at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity with SEQ ID NO: 8 or 9. SEQ ID NO: 8 is a nucleotide sequence encoding mouse FGF21. SEQ ID NO: 9 is a codon optimized nucleotide sequence encoding mouse FGF21.

In some embodiments, a nucleotide sequence encoding canine FGF21 present in a gene construct according to the invention has at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity with SEQ ID NO: 10 or 11. SEQ ID NO: 10 is a nucleotide sequence encoding canine FGF21. SEQ ID NO: 11 is a codon optimized nucleotide sequence encoding canine FGF21.

In some embodiments, there is provided a gene construct as described herein, wherein the nucleotide sequence encoding an FGF21 is selected from the group consisting of:

(a) a nucleotide sequence encoding a polypeptide comprising an amino acid sequence that has at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity or similarity with the amino acid sequence of SEQ ID NO: 1, 2 or 3.

(b) a nucleotide sequence that has at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity with the nucleotide sequence of SEQ ID NO: 4, 5, 6, 7, 8, 9, 10 or 11.

(c) a nucleotide sequence the sequence of which differs from the sequence of a nucleotide sequence of (b) due to the degeneracy of the genetic code.

In a preferred embodiment, a nucleotide sequence encoding an FGF21 is a codon-optimized nucleotide sequence, preferably a codon-optimized human sequence, preferably selected from the sequences of SEQ ID NO: 5, 6 and 7.

An FGF21 encoded by the nucleotide sequences described herein exerts at least a detectable level of an activity of an FGF21 as known to a person of skill in the art. An activity of an FGF21 can be to exhibit an anti-obesity and/or an anti-diabetes effect as described in more detail later herein. An activity of an FGF21 can also be to increase insulin sensitivity. This activity could be assessed by methods known to a person of skill in the art, for example by using an insulin tolerance test or a glucose tolerance test.

In some embodiments, the nucleotide sequence encoding FGF21 is operably linked to a ubiquitous promoter. A preferred ubiquitous promoter is selected from the CMV promoter and the CAG promoter, preferably the CAG promoter. In some embodiments, the nucleotide sequence encoding FGF21 is operably linked to a ubiquitous promoter and at least one target sequence of a microRNA expressed in a tissue where the expression of FGF21 is wanted to be prevented.

A description of "ubiquitous promoter", "operably linked" and "microRNA" has been provided under the section entitled "general information". A "target sequence of a microRNA expressed in a tissue" or "target sequence binding to a microRNA expressed in a tissue" or "binding site of a microRNA expressed in a tissue" as used herein refers to a nucleotide sequence which is complementary or partially complementary to at least a portion of a microRNA expressed in said tissue, as described elsewhere herein.

In some embodiments, the at least one target sequence of a microRNA is selected from those target sequences that bind to microRNAs expressed in heart and/or liver of a mammal.

In some embodiments, the nucleotide sequence encoding FGF21 is operably linked to a ubiquitous promoter and at least one target sequence of a microRNA expressed in the liver and at least one target sequence of a microRNA expressed in the heart.

A "target sequence of a microRNA expressed in the liver" or "target sequence binding to a microRNA expressed in the liver" or "binding site of a microRNA expressed in the liver" as used herein refers to a nucleotide sequence which is complementary or partially complementary to at least a portion of a microRNA expressed in the liver. Similarly, a "target sequence of a microRNA expressed in the heart" or "target sequence binding to a microRNA expressed in the heart" or "binding site of a microRNA expressed in the heart" as used herein refers to a nucleotide sequence which is complementary or partially complementary to at least a portion of a microRNA expressed in the heart.

A portion of a microRNA expressed in the liver or a portion of a microRNA expressed in the heart, as described herein, means a nucleotide sequence of at least four, at least five, at least six or at least seven consecutive nucleotides of said microRNA. The binding site sequence can have perfect complementarity to at least a portion of an expressed microRNA, meaning that the sequences are a perfect match without any mismatch occurring. Alternatively, the binding site sequence can be partially complementary to at least a portion of an expressed microRNA, meaning that one mismatch in four, five, six or seven consecutive nucleotides may occur. Partially complementary binding sites preferably contain perfect or near perfect complementarity to the seed region of the microRNA, meaning that no mismatch (perfect complementarity) or one mismatch per four, five, six or seven consecutive nucleotides (near perfect complementarity) may occur between the seed region of the microRNA and its binding site. The seed region of the microRNA consists of the 5' region of the microRNA from about nucleotide 2 to about nucleotide 8 of the microRNA. The portion as described herein is preferably the seed region of said microRNA. Degradation of the messenger RNA (mRNA) containing the target sequence for a microRNA expressed in the liver or a microRNA expressed in the heart may be through the RNA interference pathway or via direct translational control (inhibition) of the mRNA. This invention is in no way limited by the pathway ultimately utilized by the miRNA in inhibiting expression of the transgene or encoded protein.

In the context of the invention, a target sequence that binds to microRNAs expressed in the liver may be replaced by a nucleotide sequence comprising a nucleotide sequence that has at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity with SEQ ID NO: 12 or 14-20.

In a preferred embodiment, the target sequence of a microRNA expressed in the liver may be replaced by a nucleotide sequence comprising a nucleotide sequence that has at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity with SEQ ID NO: 12. In a further embodiment, at least one copy of a target sequence of a microRNA expressed in the liver, as described in SEQ ID NO: 12 or 14-20, is present in the gene construct of the invention. In a further embodiment, two, three, four, five, six, seven or eight copies of a target sequence of a microRNA expressed in the liver, as described in SEQ ID NO: 12 or 14-20, are present in the gene construct of the invention. In a preferred embodiment, one, two, three, four, five, six, seven or eight copies of the sequence miRT-122a (SEQ ID NO: 12) are present in the gene construct of the invention. A preferred number of copies of a target sequence of a microRNA expressed in the liver is four.

A target sequence of a microRNA expressed in the liver as used herein exerts at least a detectable level of activity of a target sequence of a microRNA expressed in the liver as known to a person of skill in the art. An activity of a target sequence of a microRNA expressed in the liver is to bind to its cognate microRNA expressed in the liver and, when operatively linked to a transgene, to mediate detargeting of transgene expression in the liver. This activity may be assessed by measuring the levels of transgene expression in the liver on the level of the mRNA or the protein by standard assays known to a person of skill in the art, such as qPCR, Western blot analysis or ELISA.

In the context of the invention, a target sequence of a microRNA expressed in the heart may be replaced by a nucleotide sequence comprising a nucleotide sequence that has at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity with SEQ ID NO: 13 or 21-25.

In a preferred embodiment, the target sequence of a microRNA expressed in the heart may be replaced by a nucleotide sequence comprising a nucleotide sequence that has at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity with SEQ ID NO: 13. In a further embodiment, at least one copy of a target sequence of a microRNA expressed in the heart, as described in SEQ ID NO: 13 or 21-25, is present in the gene construct of the invention. In a further embodiment, two, three, four, five, six, seven or eight copies of a target sequence of a microRNA expressed in the heart, as described in SEQ ID NO: 13 or 21-25, are present in the gene construct of the invention. In a preferred embodiment, one, two, three, four, five, six, seven or eight copies of a nucleotide sequence encoding miRT-1 (SEQ ID NO: 13), are present in the gene construct of the invention. A preferred number of copies of a target sequence of a microRNA expressed in the heart is four.

A target sequence of a microRNA expressed in the heart as used herein exerts at least a detectable level of activity of a target sequence of a microRNA expressed in the heart as known to a person of skill in the art. An activity of a target sequence of a microRNA expressed in the heart is to bind to its cognate microRNA expressed in the heart and, when operatively linked to a transgene, to mediate detargeting of transgene expression in the heart. This activity may be assessed by measuring the levels of transgene expression in the heart on the level of the mRNA or the protein by standard assays known to a person of skill in the art, such as qPCR, Western blot analysis or ELISA.

In some embodiments, at least one copy of a target sequence of a microRNA expressed in the liver, as described in SEQ ID NO: 12 or 14-20, and at least one copy of a target sequence of a microRNA expressed in the heart, as described in SEQ ID NO: 13 or 21-25, are present in the gene construct of the invention. In a further embodiment, two, three, four, five, six, seven or eight copies of a target sequence of a microRNA expressed in the liver, as described in SEQ ID NO: 12 or 14-20, and two, three, four, five, six, seven or eight copies of a target sequence of a microRNA expressed in the heart, as described in SEQ ID NO: 13 or 21-25, are present in the gene construct of the invention. In a further embodiment one, two, three, four, five, six, seven or eight copies of a nucleotide sequence encoding miRT-122a (SEQ ID NO: 12) and one, two, three, four, five, six, seven or eight copies nucleotide sequence encoding miRT-1 (SEQ ID NO: 13) are combined in the gene construct of the invention. In a further embodiment, four copies of a nucleotide sequence encoding miRT-122a (SEQ ID NO: 12) and four copies of nucleotide sequence encoding miRT-1 (SEQ ID NO: 13) are combined in the gene construct of the invention.

In some embodiments there is provided a gene construct as described above, wherein the target sequence of a microRNA expressed in the liver and the target sequence of a microRNA expressed in the heart is selected from a group consisting of sequences SEQ ID NO: 12 to 25 and/or combinations thereof. In some embodiments there is provided a gene construct as described above, wherein the target sequence of a microRNA expressed in the heart is selected from SEQ ID NO's: 13 and 21-25 and a target sequence of a microRNA expressed in the liver is selected from SEQ ID NO's: 12 and 14-20. In some embodiments there is provided a gene construct as described above, wherein the gene construct comprises a target sequence of microRNA-122a and a target sequence of microRNA-1.

In some embodiments, a ubiquitous promoter as described herein is selected from the group consisting of a CAG promoter, a CMV promoter, a mini-CMV promoter, a β-actin promoter, a rous-sarcoma-virus (RSV) promoter, an elongation factor 1 alpha (EF1α) promoter, an early growth response factor-1 (Egr-1) promoter, an Eukaryotic Initiation Factor 4A (eIF4A) promoter, a ferritin heavy chain-encoding gene (FerH) promoter, a ferritin heavy light-encoding gene (FerL) promoter, a glyceraldehyde-3-phosphate dehydrogenase (GAPDH) promoter, a GRP78 promoter, a GRP94 promoter, a heat-shock protein 70 (hsp70) promoter, an ubiquitin B promoter, a SV40 promoter, a Beta-Kinesin promoter, a ROSA26 promoter and a PGK-1 promoter.

In a preferred embodiment, the ubiquitous promoter is a CAG promoter. CAG promoters are demonstrated in the examples to be suitable for use in a gene construct according to the invention. In some embodiments, a CAG promoter comprises, consists essentially of, or consists of a nucleotide sequence that has at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity with SEQ ID NO: 27.

Another preferred ubiquitous promoter is a cytomegalovirus (CMV) promoter. In some embodiments, a CMV promoter comprises, consists essentially of, or consists of a nucleotide sequence that has at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity with SEQ ID NO: 28. Preferably said CMV promoter is used together with an intronic sequence. In some embodiments, an intronic sequence comprises, consists essentially of, or consists of a nucleotide sequence that has at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity with SEQ ID NO: 26.

Another preferred ubiquitous promoter is a mini-CMV promoter. In some embodiments, a mini-CMV promoter comprises, consists essentially of, or consists of a nucleotide sequence that has at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity with SEQ ID NO: 36.

Another preferred ubiquitous promoter is an EF1a promoter. In some embodiments, an EF1a promoter comprises, consists essentially of, or consists of a nucleotide sequence that has at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity with SEQ ID NO: 37.

Another preferred ubiquitous promoter is an RSV promoter. In some embodiments, an RSV promoter comprises, consists essentially of, or consists of a nucleotide sequence that has at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity with SEQ ID NO: 38.

In some embodiments, the nucleotide sequence encoding FGF21 is operably linked to a tissue-specific promoter. In a preferred embodiment, a tissue-specific promoter is a CNS-specific promoter, more preferably a brain-specific promoter, most preferably a hypothalamus-specific promoter.

A description of "tissue-specific promoter" has been provided under the section entitled "general information".

In some embodiments, a CNS-specific promoter as described herein is selected from the group consisting of a Synapsin 1 promoter, a Neuron-specific enolase (NSE) promoter, a Calcium/calmodulin-dependent protein kinase II (CaMKII) promoter, a tyrosine hydroxylase (TH) promoter, a Forkhead Box A2 (FOXA2) promoter, an alpha-internexin (INA) promoter, a Nestin (NES) promoter, a Glial fibrillary acidic protein (GFAP) promoter, an Aldehyde Dehydrogenase 1 Family Member L1 (ALDH1L1) promoter, a myelin-associated oligodendrocyte basic protein (MOBP) promoter, a Homeobox Protein 9 (HB9) promoter and a Myelin basic protein (MBP) promoter.

In some embodiments, a brain-specific promoter as described herein is selected from the group consisting of a Synapsin 1 promoter, a Neuron-specific enolase (NSE) promoter, a Calcium/calmodulin-dependent protein kinase II (CaMKII) promoter, a tyrosine hydroxylase (TH) promoter, a Forkhead Box A2 (FOXA2) promoter, an alpha-internexin (INA) promoter, a Nestin (NES) promoter, a Glial fibrillary acidic protein (GFAP) promoter, an Aldehyde Dehydrogenase 1 Family Member L1 (ALDH1L1) promoter, a myelin-associated oligodendrocyte basic protein (MOBP) promoter and a Myelin basic protein (MBP) promoter.

In some embodiments, a hypothalamus-specific promoter may be a Gonadotropin-releasing hormone (GnRH) promoter.

In a preferred embodiment, the CNS- and/or brain-specific promoter is a synapsin 1 promoter. In some embodiments, a synapsin 1 promoter comprises, consists essentially of, or consists of a nucleotide sequence that has at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity with SEQ ID NO: 39.

Another preferred CNS- and/or brain-specific promoter is a calcium/calmodulin-dependent protein kinase II (CaMKII) promoter. In some embodiments, a calcium/calmodulin-dependent protein kinase II (CaMKII) promoter comprises, consists essentially of, or consists of a nucleotide sequence that has at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity with SEQ ID NO: 40.

Another preferred CNS- and/or brain-specific promoter is a Glial fibrillary acidic protein (GFAP) promoter. In some embodiments, a Glial fibrillary acidic protein (GFAP) promoter comprises, consists essentially of, or consists of a nucleotide sequence that has at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity with SEQ ID NO: 41.

Another preferred CNS- and/or brain-specific promoter is a Nestin promoter. In some embodiments, a Nestin promoter comprises, consists essentially of, or consists of a nucleotide sequence that has at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity with SEQ ID NO: 42.

Another preferred CNS-specific promoter is a Homeobox Protein 9 (HB9) promoter. In some embodiments, a Homeobox Protein 9 (HB9) promoter comprises, consists essentially of, or consists of a nucleotide sequence that has at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity with SEQ ID NO: 43.

Another preferred CNS- and/or brain-specific promoter is a tyrosine hydroxylase (TH) promoter. In some embodiments, a tyrosine hydroxylase (TH) promoter comprises, consists essentially of, or consists of a nucleotide sequence that has at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity with SEQ ID NO: 44.

Another preferred CNS- and/or brain-specific promoter is a Myelin basic protein (MBP) promoter. In some embodiments, a Myelin basic protein (MBP) promoter comprises, consists essentially of, or consists of a nucleotide sequence that has at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity with SEQ ID NO: 45.

In some embodiments, CNS-, brain- and/or hypothalamus-specific promoters as described herein direct expression of said nucleotide sequence in at least one cell of the CNS and/or brain and/or hypothalamus. Preferably, said promoter directs expression in at least 10%, 20%, 30%, 40%, 40%, 60%, 70%, 80%, 90%, or 100% of cells of the CNS and/or the brain and/or the hypothalamus. A CNS- and/or brain-specific promoter, as used herein, also encompasses promoters directing expression in a specific region or cellular subset of the CNS and/or brain. Accordingly, CNS- and/or brain specific promoters as described herein may also direct expression in at least 10%, 20%, 30%, 40%, 40%, 60%, 70%, 80%, 90%, or 100% of cells of the hippocampus, the cerebellum, the cortex, the hypothalamus and/or the olfactory bulb. Expression may be assessed as described under the section entitled "general information".

A promoter as used herein (especially when the promoter sequence is described as having a minimal identity percentage with a given SEQ ID NO) should exert at least an activity of a promoter as known to a person of skill in the art. Preferably a promoter described as having a minimal identity percentage with a given SEQ ID NO should control transcription of the nucleotide sequence to which it is operably linked (i.e. at least a nucleotide sequence encoding a FGF21) as assessed in an assay known to a person of skill in the art. For example, such assay could involve measuring expression of the transgene. Expression may be assessed as described under the section entitled "general information".

Additional sequences may be present in the gene construct of the invention. Exemplary additional sequences suitable herein include inverted terminal repeats (ITRs), an SV40 polyadenylation signal (SEQ ID NO: 32), a rabbit β-globin polyadenylation signal (SEQ ID NO: 33), a CMV enhancer sequence (SEQ ID NO: 29). Within the context of the invention, "ITRs" is intended to encompass one 5'ITR and one 3'ITR, each being derived from the genome of an AAV. Preferred ITRs are from AAV2 and are represented by SEQ ID NO: 30 (5' ITR) and SEQ ID NO: 31 (3' ITR). Within the context of the invention, it is encompassed to use the CMV enhancer sequence (SEQ ID NO: 29) and the CMV promoter sequence (SEQ ID NO: 28) as two separate sequences or as a single sequence (SEQ ID NO: 34). Each of these additional sequences may be present in a gene construct according to the invention.

Optionally, additional nucleotide sequences may be operably linked to the nucleotide sequence(s) encoding an FGF21, such as nucleotide sequences encoding signal sequences, nuclear localization signals, expression enhancers, and the like.

In some embodiments, there is provided a gene construct comprising a nucleotide sequence encoding FGF21, optionally wherein the gene construct does not comprise a target sequence of a microRNA expressed in a tissue where the expression of FGF21 is wanted to be prevented.

Expression Vector

Gene constructs described herein can be placed in expression vectors. Thus, in another aspect there is provided an expression vector comprising a gene construct as described in any of the preceding embodiments. A description of "expression vector" has been provided under the section entitled "general information".

In some embodiments, an expression vector as described herein is for use in therapy. In a preferred embodiment, an expression vector as described herein is for use in the treatment and/or prevention of a metabolic disorder. In a preferred embodiment, the therapy involves expression of the gene construct comprised in the expression vector in the CNS, preferably in the brain, more preferably in the hypothalamus. In some embodiments, expression of the gene construct in the brain may mean expression of the gene construct in the hypothalamus and/or the cortex and/or the hippocampus and/or the cerebellum and/or the olfactory bulb, preferably the hypothalamus. Accordingly, expression of the gene construct in the brain may mean expression of the gene construct in at least one or at least two or at least three or all brain regions selected from the group consisting of the hypothalamus, the cortex, the hippocampus, the cerebellum and the olfactory bulb. In a preferred embodiment, the therapy involves expression of the gene construct in the hypothalamus. In some embodiments, expression in the CNS and/or the brain and/or the hypothalamus and/or the cortex and/or the hippocampus and/or the cerebellum and/or the olfactory bulb may mean specific expression in the CNS and/or the brain and/or the hypothalamus and/or the cortex and/or the hippocampus and/or the cerebellum and/or the olfactory bulb. In an embodiment, expression does not involve expression in the liver, pancreas, adipose tissue, skeletal muscle and/or heart. In some embodiments, expression does not involve expression in at least one, at least two, at least three, at least four or all organs selected from the group consisting of the liver, pancreas, adipose tissue, skeletal muscle and heart. A description of CNS- and/or brain- and/or hypothalamus and/or cortex- and/or hippocampus- and/or cerebellum- and/or olfactory bulb-specific expression has been provided under the section entitled "general information".

Expression may be assessed as described under the section entitled "general information". A description of "CNS", "brain" and "hypothalamus" has been provided under the section entitled "general information".

In some embodiments, an expression vector as described herein is for use in therapy, wherein the expression vector is administered by intra-CSF (cerebrospinal fluid) administration (via cisterna magna, intrathecal or intraventricular delivery), intraparenchymal or by intranasal administration. A preferred administration is intra-CSF administration.

"Intra-CSF administration", "intranasal administration", "intraparenchymal administration" "intra-cisterna magna administration", "intrathecal administration" and "intraventricular administration", as used herein, are described in the part of this application entitled "general information".

In some embodiments, the expression vector is a viral expression vector. A description of "viral expression vector" has been provided under the section entitled "general information".

A viral vector may be a viral vector selected from the group consisting of adenoviral vectors, adeno-associated viral vectors, retroviral vectors and lentiviral vectors. An adenoviral vector is also known as an adenovirus derived vector, an adeno-associated viral vector is also known as an adeno-associated virus derived vector, a retroviral vector is also known as a retrovirus derived vector and a lentiviral vector is also known as a lentivirus derived vector. A preferred viral vector is an adeno-associated viral vector. A description of "adeno-associated viral vector" has been provided under the section entitled "general information".

In some embodiments, the vector is an adeno-associated vector or adeno-associated viral vector or an adeno-associated virus derived vector (AAV) selected from the group consisting of AAV of serotype 1 (AAV1), AAV of serotype 2 (AAV2), AAV of serotype 3 (AAV3), AAV of serotype 4 (AAV4), AAV of serotype 5 (AAV5), AAV of serotype 6 (AAV6), AAV of serotype 7 (AAV7), AAV of serotype 8 (AAV8), AAV of serotype 9 (AAV9), AAV of serotype rh10 (AAVrh10), AAV of serotype rh8 (AAVrh8), AAV of serotype Cb4 (AAVCb4), AAV of serotype rh74 (AAVrh74), AAV of serotype DJ (AAVDJ), AAV of serotype 2/5 (AAV2/5), AAV of serotype 2/1 (AAV2/1), AAV of serotype 1/2 (AAV1/2), AAV of serotype Anc80 (AAVAnc80).

In a preferred embodiment, the vector is an AAV of serotype 1, 2 or 9 (AAV1, AAV2, or AAV9). These AAV serotypes are demonstrated in the examples to be suitable for use as an expression vector according to the invention.

In a preferred embodiment, the expression vector is an AAV1 or AAV2 or AAV9, preferably an AAV9, and comprises a gene construct comprising a nucleotide sequence encoding FGF21. More preferably such gene construct comprises a CAG promoter comprising, consisting essentially of, or consisting of a nucleotide sequence that has at least 60% with SEQ ID NO:27. More preferably, such gene construct comprises at least one target sequence of a microRNA expressed in a tissue where the expression of FGF21 is wanted to be prevented as described herein.

In another preferred embodiment, the expression vector is an AAV1 and comprises a gene construct comprising a nucleotide sequence encoding FGF21, optionally wherein the gene construct does not comprise a target sequence of a microRNA. In an embodiment, the gene construct does not comprise a target sequence of a miRNA, which is expressed in a tissue where the expression of FGF21 is wanted to be prevented. More preferably such gene construct comprises a CAG promoter comprising, consisting essentially of, or consisting of a nucleotide sequence that has at least 60% with SEQ ID NO:27.

Composition

In a further aspect there is provided a composition comprising a gene construct as described above and/or a viral vector as described above, together with one or more pharmaceutically acceptable ingredients.

Such composition may be called a gene therapy composition. Preferably, the composition is a pharmaceutical composition.

As used herein, "pharmaceutically acceptable ingredients" include pharmaceutically acceptable carriers, fillers, preservatives, solubilizers, vehicles, diluents and/or excipients. Accordingly, the one or more pharmaceutically acceptable ingredients may be selected from the group consisting of pharmaceutically acceptable carriers, fillers, preservatives, solubilizers, vehicles, diluents and/or excipients. Such pharmaceutically acceptable carriers, fillers, preservatives, solubilizers, vehicles, diluents and/or excipients may for instance be found in Remington: The Science and Practice of Pharmacy, 22nd edition. Pharmaceutical Press (2013).

In some embodiments, a composition as described herein is for use in therapy. In a preferred embodiment, a composition as described herein is for use in the treatment and/or prevention of a metabolic disorder. In a preferred embodiment, the therapy involves expression of the gene construct comprised in the composition in the CNS, preferably in the brain, more preferably in the hypothalamus. In some embodiments, expression of the gene construct in the brain may mean expression of the gene construct in the hypothalamus and/or the cortex and/or the hippocampus and/or the cerebellum and/or the olfactory bulb, preferably the hypothalamus. Accordingly, expression of the gene construct in the brain may mean expression of the gene construct in at least one or at least two or at least three or all brain regions selected from the group consisting of the hypothalamus, the cortex, the hippocampus, the cerebellum and the olfactory bulb. In a preferred embodiment, the therapy involves expression of the gene construct in the hypothalamus. In some embodiments, expression in the CNS and/or the brain and/or the hypothalamus and/or the cortex and/or the hippocampus and/or the cerebellum and/or the olfactory bulb may mean specific expression in the CNS and/or the brain and/or the hypothalamus and/or the cortex and/or the hippocampus and/or the cerebellum and/or the olfactory bulb. In an embodiment, expression does not involve expression in the liver, pancreas, adipose tissue, skeletal muscle and/or heart. In some embodiments, expression does not involve expression in at least one, at least two, at least three, at least four or all organs selected from the group consisting of the liver, pancreas, adipose tissue, skeletal muscle and heart. A description of CNS- and/or brain- and/or hypothalamus and/or cortex- and/or hippocampus- and/or cerebellum- and/or olfactory bulb-specific expression has been provided under the section entitled "general information".

Expression may be assessed as described under the section entitled "general information". A description of "CNS", "brain" and "hypothalamus" has been provided under the section entitled "general information".

In some embodiments, a composition as described herein is for use in therapy, wherein the composition is administered by intra-CSF (cerebrospinal fluid) administration (via cisterna *magna*, intrathecal or intraventricular delivery), intraparenchymal or by intranasal administration. A preferred administration is intra-CSF administration.

"Intra-CSF administration", "intranasal administration", "intraparenchymal administration" "intra-cisterna magna administration", "intrathecal administration" and "intraventricular administration", as used herein, are described in the part of this application entitled "general information".

A further compound may be present in a composition of the invention. Said compound may help in delivery of the composition. Suitable compounds in this context are: compounds capable of forming complexes, nanoparticles, micelles and/or liposomes that deliver each constituent as described herein, complexed or trapped in a vesicle or liposome through a cell membrane. Many of these compounds are known in the art. Suitable compounds comprise polyethylenimine (PEI), or similar cationic polymers, including polypropyleneimine or polyethylenimine copolymers (PECs) and derivatives; synthetic amphiphiles (SAINT-18); lipofectin™, DOTAP. A person of skill in the art will know which type of formulation is the most appropriate for a composition as described herein.

Method and Use

In a further aspect, there is provided a gene construct as described herein, for use in therapy, wherein the therapy involves expression of the gene construct in the CNS, preferably in the brain, more preferably in the hypothalamus and/or the cortex and/or the hippocampus and/or the cerebellum and/or the olfactory bulb, most preferably in the hypothalamus.

Further provided is an expression vector as described herein, for use in therapy, wherein the therapy involves expression of the gene construct comprised in the expression vector in the CNS, preferably in the brain, more preferably in the hypothalamus and/or the cortex and/or the hippocampus and/or the cerebellum and/or the olfactory bulb, most preferably in the hypothalamus.

Further provided is a pharmaceutical composition as described herein, for use in therapy, wherein the therapy involves expression of the gene construct comprised in the pharmaceutical composition in the CNS, preferably in the brain, more preferably in the hypothalamus and/or the cortex and/or the hippocampus and/or the cerebellum and/or the olfactory bulb, most preferably in the hypothalamus.

In some embodiments, a gene construct as described herein, and/or expression vector as described herein and/or a pharmaceutical composition as described herein is for use in the treatment and/or prevention of a metabolic disorder, preferably obesity and/or diabetes, wherein the therapy involves expression of the gene construct in the CNS, preferably in the brain, more preferably in the hypothalamus and/or the cortex and/or the hippocampus and/or the cerebellum and/or the olfactory bulb, most preferably in the hypothalamus.

In a further aspect there is provided a method of treatment, comprising administering a gene construct, an expression vector or a pharmaceutical composition as described herein, wherein the method involves the expression of a gene construct as described herein in the CNS, preferably in the brain, more preferably in the hypothalamus and/or the cortex and/or the hippocampus and/or the cerebellum and/or the olfactory bulb, most preferably in the hypothalamus.

In some embodiments, administering a gene construct, an expression vector or a pharmaceutical composition means administering to a subject in need thereof a therapeutically effective amount of a gene construct, an expression vector or a pharmaceutical composition.

In some embodiments there is provided a method of treatment, comprising administering a gene construct, an expression vector or a pharmaceutical composition as described herein, wherein the method is for treating and/or preventing a metabolic disorder and involves the expression of a gene construct as described herein in the CNS, preferably in the brain, more preferably in the hypothalamus and/or the cortex and/or the hippocampus and/or the cerebellum and/or the olfactory bulb, most preferably in the hypothalamus.

In a further aspect there is provided a use of a gene construct, an expression vector or a pharmaceutical composition as described herein, for the manufacture of a medicament, wherein said medicament involves the expression of a gene construct as described herein in the CNS, preferably in the brain, more preferably in the hypothalamus and/or the cortex and/or the hippocampus and/or the cerebellum and/or the olfactory bulb, most preferably in the hypothalamus.

In some embodiments there is provided a use of a gene construct, an expression vector or a pharmaceutical composition as described herein, for the manufacture of a medicament, wherein said medicament is for the treatment and/or prevention of a metabolic disorder and involves the expression of a gene construct as described herein in the CNS, preferably in the brain, more preferably in the hypothalamus and/or the cortex and/or the hippocampus and/or the cerebellum and/or the olfactory bulb, most preferably in the hypothalamus.

In a further aspect there is provided a use of a gene construct, an expression vector or a pharmaceutical composition as described herein, for medical treatment, wherein said medical treatment involves the expression of a gene construct as described herein in the CNS, preferably in the brain, more preferably in the hypothalamus and/or the cortex and/or the hippocampus and/or the cerebellum and/or the olfactory bulb, most preferably in the hypothalamus.

In some embodiments there is provided a use of a gene construct, an expression vector or a pharmaceutical composition as described herein, for medical treatment, wherein said medical treatment is for the treatment and/or prevention of a metabolic disorder and involves the expression of a gene construct as described herein in the CNS, preferably in the brain, more preferably in the hypothalamus and/or the cortex and/or the hippocampus and/or the cerebellum and/or the olfactory bulb, most preferably in the hypothalamus.

Within the context of gene constructs for use, expression vectors for use, pharmaceutical compositions for use, methods and uses according to the invention, "involving the expression of a gene construct" may be replaced by "causing the expression of a gene construct" or "inducing the expression of a gene construct".

Within the context of gene constructs for use, expression vectors for use, pharmaceutical compositions for use, methods and uses according to the invention, the therapy and/or treatment and/or medicament may involve expression of the gene construct in the CNS, preferably the brain, more preferably the hypothalamus. In some embodiments, expression of the gene construct in the brain may mean expression of the gene construct in the hypothalamus and/or the cortex and/or the hippocampus and/or the cerebellum and/or the olfactory bulb, preferably in the hypothalamus. Accordingly, expression of the gene construct in the brain may mean expression of the gene construct in at least one or at least two or at least three or all brain regions selected from the group consisting of the hypothalamus, the cortex, the hippocampus, the cerebellum and the olfactory bulb. In a preferred embodiment, the therapy involves expression of the gene construct in the hypothalamus. In some embodiments, expression in the CNS and/or the brain and/or the hypothalamus and/or the cortex and/or the hippocampus and/or the cerebellum and/or the olfactory bulb may mean specific expression in the CNS and/or the brain and/or the hypothalamus and/or the cortex and/or the hippocampus and/or the cerebellum and/or the olfactory bulb. In an embodiment, expression does not involve expression in the liver, pancreas, adipose tissue, skeletal muscle and/or heart. In some embodiments, expression does not involve expression in at least one, at least two, at least three, at least four or all organs selected from the group consisting of the liver, pancreas, adipose tissue, skeletal muscle and heart. A description of CNS- and/or brain- and/or hypothalamus and/or cortex- and/or hippocampus- and/or cerebellum- and/or olfactory bulb-specific expression has been provided under the section entitled "general information".

Within the context of gene constructs for use, expression vectors for use, pharmaceutical compositions for use, methods and uses according to the invention, a gene construct and/or an expression vector and/or a pharmaceutical composition may be administered by intra-CSF (cerebrospinal fluid) administration (via cisterna magna, intrathecal or intraventricular delivery).

Within the context of gene constructs for use, expression vectors for use, pharmaceutical compositions for use, methods and uses according to the invention, a gene construct and/or an expression vector and/or a pharmaceutical composition may be administered by intraparenchymal administration.

Within the context of gene constructs for use, expression vectors for use, pharmaceutical compositions for use, methods and uses according to the invention, a gene construct and/or an expression vector and/or a pharmaceutical composition may be administered by intranasal administration.

"Intra-CSF administration", "intranasal administration", "intraparenchymal administration" "intra-cisterna magna administration", "intrathecal administration" and "intraventricular administration", as used herein, are described in the part of this application entitled "general information".

Within the context of gene constructs for use, expression vectors for use, pharmaceutical compositions for use, methods and uses according to the invention, the therapy and/or treatment and/or medicament may be for use in the treatment and/or prevention of a metabolic disorder, preferably obesity and/or diabetes. Complications of a metabolic disorder may also be encompassed.

Metabolic disorders may include metabolic syndrome, diabetes, obesity, obesity-related comorbidities, diabetes-related comorbidities, hyperglycaemia, insulin resistance, glucose intolerance, hepatic steatosis, alcoholic liver diseases (ALD), non-alcoholic fatty liver disease (NAFLD), non-alcoholic steatohepatitis (NASH), coronary heart disease (CHD), hyperlipidemia, atherosclerosis, endocrinopathies, osteosarcopenic obesity syndrome (OSO), diabetic nephropathy, chronic kidney disease (CKD), cardiac hypertrophy, diabetic retinopathy, diabetic nephropathy, diabetic neuropathy, arthritis, sepsis, ocular neovascularization, neurodegeneration, dementia, and may also include depression, adenoma, carcinoma.

Diabetes may include prediabetes, hyperglycaemia, Type 1 diabetes, Type 2 diabetes, maturity-onset diabetes of the young (MODY), monogenic diabetes, neonatal diabetes, gestational diabetes, brittle diabetes, idiopathic diabetes, drug- or chemical-induced diabetes, Stiff-man syndrome, lipoatrophic diabetes, latent autoimmune diabetes in adults (LADA).

Obesity may include overweight, central/upper body obesity, peripheral/lower body obesity, morbid obesity, osteosarcopenic obesity syndrome (OSO), pediatric obesity, Mendelian (monogenic) syndromic obesity, Mendelian non-syndromic obesity, polygenic obesity.

Preferred metabolic disorders are obesity and/or a diabetes.

In a preferred embodiment, a treatment or a therapy or a use or the administration of a medicament as described herein does not have to be repeated. In some embodiments, a treatment or a therapy or a use or the administration of a medicament as described herein may be repeated each year or each 2, 3, 4, 5, 6, 7, 8, 9 or 10, including intervals between any two of the listed values, years.

The subject treated may be a higher mammal, such as a cat, a rodent, (preferably mice, rats, gerbils and guinea pigs, and more preferably mice and rats), a dog, or a human being.

Within the context of gene constructs for use, expression vectors for use, pharmaceutical compositions for use, methods and uses according to the invention, a gene construct and/or an expression vector and/or a pharmaceutical composition as described herein preferably exhibits an anti-diabetes effect and/or an anti-obesity effect.

An anti-diabetes effect may be reached when glucose disposal in blood is increased and/or when glucose tolerance is improved and/or when insulin sensitivity is increased. This could be assessed using techniques known to a person of skill in the art such as measurement of glycaemia, insulinemia and/or performance of an insulin tolerance test and/or of a glucose tolerance test, for example as done in the experimental part. In this context, "increase" (respectively "improvement") means at least a detectable increase (respectively a detectable improvement) using an assay known to a person of skill in the art. The increase may be an increase of at least 5%, at least 10%, at least 20%, at least 30%, at least 40%, at least 50%, at least 60%, at least 70%, at least 80%, at least 90% or at least 100% using assays such as the measurement of glycaemia, insulinemia and/or performance of an insulin tolerance test and/or of a glucose tolerance test.

An anti-obesity effect may be reached when body weight, body weight gain and/or body fat percentage is decreased. An anti-obesity effect may also be reached when body mass index (BMI), waist circumference, waist-to-hip ratio (WHR) and/or waist-to-height ratio (WHtR) is decreased. An anti-obesity effect may also be reached when weight of tissues, such as the liver, is decreased. This could be assessed using techniques known to a person of skill in the art, for example as done in the experimental part. In this context, "decrease" (respectively "improvement") means at least a detectable decrease (respectively a detectable improvement) using an assay known to a person of skill in the art, such as assays as carried out in the experimental part. Anti-obesity effects include both prevention of obesity and reversion of obesity.

An anti-diabetes effect and/or an anti-obesity effect may also be observed when the progression of a typical symptom (e.g. insulitis, beta cell loss, decrease of beta cellmass, increase of body weight) has been slowed down as assessed by a physician. A decrease of a typical symptom may mean a slowdown in progression of symptom development or a complete disappearance of symptoms. Symptoms, and thus also a decrease in symptoms, can be assessed using a variety of methods, to a large extent the same methods as used in diagnosis of diabetes and/or obesity, including clinical examination and routine laboratory tests. Such methods include both macroscopic and microscopic methods, as well as molecular methods, radiographic methods such as X-rays, biochemical methods, immunohistochemical methods and others. Beta cell loss and/or decrease of beta cell mass may be assessed using immunohistochemical methods, preferably as carried out in the experimental part.

An anti-diabetes effect and/or an anti-obesity effect may also be observed when a reduced systemic inflammation is assessed (reduction of pro-inflammatory cytokines such as F4/80, IL-6, TNFalpha). In this context, "decrease" means at least a detectable decrease using an assay known to a person of skill in the art. The decrease may be a decrease of at least 5%, at least 10%, at least 20%, at least 30%, at least 40%, at least 50%, at least 60%, at least 70%, at least 80%, at least 90% or at least 100% using assays such as the measurement of a pro-inflammatory cytokine such as F4/80, IL-6 and/or TNF alpha using techniques known to the skilled person, preferably those used in the experimental part (i.e. RTPCR).

Within the context of gene constructs for use, expression vectors for use, pharmaceutical compositions for use, methods and uses according to the invention, a gene construct and/or an expression vector and/or a pharmaceutical composition as described herein preferably alleviates one or more symptom(s) of a metabolic disorder, such as a diabetes and/or obesity, in an individual, in a cell, tissue or organ of said individual or alleviates one or more characteristic(s) or symptom(s) of a cell, tissue or organ of said individual.

A gene construct and/or an expression vector and/or a pharmaceutical composition as described herein is preferably able to alleviate a symptom or a characteristic of a patient or of a cell, tissue or organ of said patient if after at least one week, one month, six months, one year or more of treatment using a gene construct and/or an expression vector and/or a composition of the invention, said symptom or characteristic has decreased (e.g. is no longer detectable or has slowed down), as described herein.

A gene construct and/or an expression vector and/or a pharmaceutical composition as described herein may be suitable for administration to a cell, tissue and/or an organ in vivo of individuals affected by or at risk of developing a metabolic disorder, such as a diabetes and/or obesity, and may be administered in vivo, ex vivo or in vitro. Said gene construct and/or expression vector and/or pharmaceutical composition may be directly or indirectly administered to a cell, tissue and/or an organ in vivo of an individual affected by or at risk of developing a metabolic disorder, such as a diabetes and/or obesity, and may be administered directly or indirectly in vivo, ex vivo or in vitro.

An administration mode may be intravenous, intramuscular, intrathecal, intraventricular, intraperitoneal, via inhalation, intranasal, intra-ocular and/or intraparenchymal administration. Preferred administration modes are intranasal, intraparenchymal and intra-CSF (via cisterna magna, intrathecal or intraventricular delivery) administration. Intra-CSF administration is most preferred.

A viral expression construct and/or a viral vector and/or a nucleic acid molecule and/or a composition of the invention may be directly or indirectly administered using suitable means known in the art. Improvements in means for providing an individual or a cell, tissue, organ of said individual with a viral expression construct and/or a viral vector and/or a nucleic acid molecule and/or a composition of the invention are anticipated, considering the progress that has already thus far been achieved. Such future improvements may of course be incorporated to achieve the mentioned effect of the invention. A viral expression construct and/or a viral vector and/or a nucleic acid molecule and/or a composition can be delivered as is to an individual, a cell, tissue or organ of said individual. Depending on the disease or condition, a cell, tissue or organ of said individual may be as earlier described herein. When administering a viral expression construct and/or a viral vector and/or a nucleic acid molecule and/or a composition of the invention, it is preferred that such viral expression construct and/or vector and/or nucleic acid and/or composition is dissolved in a solution that is compatible with the delivery method.

As encompassed herein, a therapeutically effective dose of a viral expression construct, vector, nucleic acid molecule and/or composition as mentioned above is preferably administered in a single and unique dose hence avoiding repeated periodical administration.

General Information

Unless stated otherwise, all technical and scientific terms used herein have the same meaning as customarily and ordinarily understood by a person of ordinary skill in the art to which this invention belongs, and read in view of this disclosure.

Sequence Identity/Similarity

In the context of the invention, a nucleic acid molecule such as a nucleic acid molecule encoding an FGF21 is represented by a nucleic acid or nucleotide sequence which encodes a protein fragment or a polypeptide or a peptide or a derived peptide. In the context of the invention, an FGF21 protein fragment or a polypeptide or a peptide or a derived peptide as Fibroblast growth factor 21 (FGF21) is represented by an amino acid sequence.

It is to be understood that each nucleic acid molecule or protein fragment or polypeptide or peptide or derived peptide or construct as identified herein by a given sequence identity number (SEQ ID NO) is not limited to this specific sequence as disclosed. Each coding sequence as identified herein encodes a given protein fragment or polypeptide or peptide or derived peptide or construct or is itself a protein fragment or polypeptide or construct or peptide or derived peptide. Throughout this application, each time one refers to a specific nucleotide sequence SEQ ID NO (take SEQ ID NO: X as example) encoding a given protein fragment or polypeptide or peptide or derived peptide, one may replace it by:

i. a nucleotide sequence comprising a nucleotide sequence that has at least 60% sequence identity with SEQ ID NO: X;

ii. a nucleotide sequence the sequence of which differs from the sequence of a nucleic acid molecule of (i) due to the degeneracy of the genetic code; or, iii. a nucleotide sequence that encodes an amino acid sequence that has at least 60% amino acid identity or similarity with an amino acid sequence encoded by a nucleotide sequence SEQ ID NO: X.

Throughout this application, each time one refers to a specific amino acid sequence SEQ ID NO (take SEQ ID NO: Y as example), one may replace it by: a polypeptide comprising an amino acid sequence that has at least 60% sequence identity or similarity with amino acid sequence SEQ ID NO: Y.

Each nucleotide sequence or amino acid sequence described herein by virtue of its identity or similarity percentage (at least 60%) with a given nucleotide sequence or amino acid sequence respectively has in a further preferred embodiment an identity or a similarity of at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% with the given nucleotide or amino acid sequence, respectively.

Each non-coding nucleotide sequence (i.e. of a promoter or of another regulatory region) could be replaced by a nucleotide sequence comprising a nucleotide sequence that has at least 60% sequence identity or similarity with a specific nucleotide sequence SEQ ID NO (take SEQ ID NO: A as example). A preferred nucleotide sequence has at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity with SEQ ID NO: A. In a preferred embodiment, such non-coding nucleotide sequence such as a promoter exhibits or exerts at least an activity of such a non-coding nucleotide sequence such as an activity of a promoter as known to a person of skill in the art.

The terms "homology", "sequence identity", "identity" and the like are used interchangeably herein. Sequence identity is herein described as a relationship between two or more amino acid (polypeptide or protein) sequences or two or more nucleic acid (polynucleotide) sequences, as determined by comparing the sequences. "Similarity" or "sequence similarity" between two amino acid sequences is determined by comparing the amino acid sequence and its conserved amino acid substitutes of one polypeptide to the sequence of a second polypeptide. "Identity" and "similarity" can be readily calculated by known methods, including but not limited to those described in Bioinformatics and the Cell: Modern Computational Approaches in Genomics, Proteomics and transcriptomics, Xia X., Springer International Publishing, New York, 2018; and Bioinformatics: Sequence and Genome Analysis, Mount D., Cold Spring Harbor Laboratory Press, New York, 2004.

Sequence identity or similarity can be calculated based on the full length of two given SEQ ID NO's or on part thereof. In some embodiments, part thereof means at least 50%, 60%, 70%, 80%, 90%, or 100% of both SEQ ID NO. In a preferred embodiment, sequence identity or similarity is determined by comparing the whole length of the sequences as identified herein. Unless otherwise indicated herein, identity or similarity with a given SEQ ID NO means identity or similarity based on the full length of said sequence (i.e. over its whole length or as a whole). In the art, "identity" also refers to the degree of sequence relatedness between amino acid or nucleic acid sequences, as the case may be, as determined by the match between strings of such sequences.

Sequence identity or similarity can be determined by alignment of two peptide or two nucleotide sequences using global or local alignment algorithms, depending on the length of the two sequences. Sequences of similar lengths are preferably aligned using a global alignment algorithms (e.g. Needleman-Wunsch) which aligns the sequences optimally over the entire length, while sequences of substantially different lengths are preferably aligned using a local alignment algorithm (e.g. Smith-Waterman). Sequences may then be referred to as "substantially identical" or "essentially similar" when they (when optimally aligned by for example the program EMBOSS needle or EMBOSS water using default parameters) share at least a certain minimal percentage of sequence identity or similarity (as described below).

A global alignment is suitably used to determine sequence identity or similarity when the two sequences have similar lengths. When sequences have a substantially different overall length, local alignments, such as those using the Smith-Waterman algorithm, are preferred. EMBOSS needle uses the Needleman-Wunsch global alignment algorithm to align two sequences over their entire length (full length), maximizing the number of matches and minimizing the number of gaps. EMBOSS water uses the Smith-Waterman local alignment algorithm. Generally, the EMBOSS needle and EMBOSS water default parameters are used, with a gap open penalty=10 (nucleotide sequences)/10 (proteins) and gap extension penalty=0.5 (nucleotide sequences)/0.5 (proteins). For nucleotide sequences the default scoring matrix used is DNAfull and for proteins the default scoring matrix is Blosum62 (Henikoff & Henikoff, 1992, PNAS 89, 915-919).

Alternatively percentage similarity or identity may be determined by searching against public databases, using algorithms such as FASTA, BLAST, etc. Thus, the nucleic acid and protein sequences of some embodiments of the present invention can further be used as a "query sequence" to perform a search against public databases to, for example, identify other family members or related sequences. Such searches can be performed using the BLASTn and BLASTx programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to oxidoreductase nucleic acid molecules of the invention. BLAST protein searches can be performed with the BLASTx program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., BLASTx and BLASTn) can be used. See the homepage of the National Center for Biotechnology Information accessible on the world wide web at www.ncbi.nlm.nih/gov/.

Optionally, in determining the degree of amino acid similarity, a person of skill in the art may also take into account so-called conservative amino acid substitutions.

As used herein, "conservative" amino acid substitutions refer to the interchangeability of residues having similar side chains. Examples of classes of amino acid residues for conservative substitutions are given in the Tables below.

| | |
|---|---|
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

Alternative conservative amino acid residue substitution classes:

| | | | |
|---|---|---|---|
| 1 | A | S | T |
| 2 | D | E | |
| 3 | N | Q | |
| 4 | R | K | |
| 5 | I | L | M |
| 6 | F | Y | W |

Alternative physical and functional classifications of amino acid residues:

| | |
|---|---|
| Alcohol group-containing residues | S and T |
| Aliphatic residues | I, L, V, and M |
| Cycloalkenyl-associated residues | F, H, W, and Y |
| Hydrophobic residues | A, C, F, G, H, I, L, M, R, T, V, W, and Y |
| Negatively charged residues | D and E |
| Polar residues | C, D, E, H, K, N, Q, R, S, and T |
| Positively charged residues | H, K, and R |
| Small residues | A, C, D, G, N, P, S, T, and V |
| Very small residues | A, G, and S |
| Residues involved in turn formation | A, C, D, E, G, H, K, N, Q, R, S, P and T |
| Flexible residues | Q, T, K, S, G, P, D, E, and R |

For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to Ser; Arg to Lys; Asn to Gln or His; Asp to Glu; Cys to Ser or Ala; Gln to Asn; Glu to Asp; Gly to Pro; His to Asn or Gln; Ile to Leu or Val; Leu to Ile or Val; Lys to Arg; Gln or Glu; Met to Leu or Ile; Phe to Met, Leu or Tyr; Ser to Thr; Thr to Ser; Trp to Tyr; Tyr to Trp or Phe; and, Val to Ile or Leu.

Gene or Coding Sequence

The term "gene" means a DNA fragment comprising a region (transcribed region), which is transcribed into an RNA molecule (e.g. an mRNA) in a cell, operably linked to suitable regulatory regions (e.g. a promoter). A gene will usually comprise several operably linked fragments, such as a promoter, a 5' leader sequence, a coding region and a 3'-nontranslated sequence (3'-end) e.g. comprising a poly-adenylation- and/or transcription termination site. A chimeric or recombinant gene (such as a FGF21 gene) is a gene not normally found in nature, such as a gene in which for example the promoter is not associated in nature with part or all of the transcribed DNA region. "Expression of a gene" refers to the process wherein a DNA region which is operably linked to appropriate regulatory regions, particularly a promoter, is transcribed into an RNA, which is biologically active, i.e. which is capable of being translated into a biologically active protein or peptide.

A "transgene" is herein described as a gene or a coding sequence or a nucleic acid molecule (i.e. a molecule encoding a FGF21) that has been newly introduced into a cell, i.e. a gene that may be present but may normally not be expressed or expressed at an insufficient level in a cell. In this context, "insufficient" means that although said FGF21 is expressed in a cell, a condition and/or disease as described herein could still be developed. In this case, the invention allows the over-expression of a FGF21. The transgene may comprise sequences that are native to the cell, sequences that naturally do not occur in the cell and it may comprise combinations of both. A transgene may contain sequences coding for a FGF21 and/or additional proteins as earlier identified herein that may be operably linked to appropriate regulatory sequences for expression of the sequences coding for a FGF21 in the cell. Preferably, the transgene is not integrated into the host cell's genome.

Promoter

As used herein, the term "promoter" or "transcription regulatory sequence" refers to a nucleic acid fragment that functions to control the transcription of one or more coding sequences, and is located upstream with respect to the direction of transcription of the transcription initiation site of the coding sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most tissues under most physiological and developmental conditions. An "inducible" promoter is a promoter that is physiologically or developmentally regulated, e.g. by the application of a chemical inducer.

A "ubiquitous promoter" is active in substantially all tissues, organs and cells of an organism.

A "organ-specific" or "tissue-specific" promoter is a promoter that is active in a specific type of organ or tissue, respectively. Organ-specific and tissue-specific promoters regulate expression of one or more genes (or coding sequence) primarily in one organ or tissue, but can allow detectable level ("leaky") expression in other organs or tissues as well. Leaky expression in other organs or tissues means at least one-fold, at least two-fold, at least three-fold, at least four-fold or at least five-fold lower, but still detectable expression as compared to the organ-specific or tissue-specific expression, as evaluated on the level of the mRNA or the protein by standard assays known to a person of skill in the art (e.g. qPCR, Western blot analysis, ELISA). The maximum number of organs or tissues where leaky expression may be detected is five, six, seven or eight.

A "CNS- or brain- or hypothalamus-specific promoter" is a promoter that is capable of initiating transcription in the CNS and/or brain and/or hypothalamus, whilst still allowing for any leaky expression in other (maximum five, six, seven or eight) organs and parts of the body. Transcription in the CNS and/or brain and/or hypothalamus can be detected in relevant areas, such as the hypothalamus, cortex, hippocampus, cerebellum and olfactory bulb, and cells, such as neurons and/or glial cells.

In the context of the invention, CNS- and/or brain- and/or hypothalamus and/or cortex- and/or hippocampus- and/or cerebellum- and/or olfactory bulb-specific promoters may be promoters that are capable of driving the preferential or predominant (at least 10% higher, at least 20% higher, at least 30% higher, at least 40% higher, at least 50% higher, at least 60% higher, at least 70% higher, at least 80% higher, at least 90% higher, at least 100% higher, at least 150% higher, at least 200% higher or more) expression of FGF21 in the CNS and/or the brain and/or the hypothalamus and/or the cortex and/or the hippocampus and/or the cerebellum and/or the olfactory bulb as compared to other organs or tissues. Other organs or tissues may be the liver, pancreas, adipose tissue, skeletal muscle, heart, kidney, colon, hematopoietic tissue, lung, ovary, spleen, stomach, testis and others. Preferably, other organs are the liver and the heart. Expression may be assessed as described elsewhere under the section entitled "general information".

Throughout the application, where CNS- and/or brain-and/or hypothalamus and/or cortex- and/or hippocampus-and/or cerebellum- and/or olfactory bulb-specific is mentioned in the context of expression, cell-type specific expression of the cell type(s) making up the CNS and/or the brain and/or the hypothalamus and/or the cortex and/or the hippocampus and/or the cerebellum and/or the olfactory bulb is also envisaged, respectively.

Operably Linked

As used herein, the term "operably linked" refers to a linkage of polynucleotide elements in a functional relationship. A nucleic acid is "operably linked" when it is placed into a functional relationship with another nucleic acid sequence. For instance, a transcription regulatory sequence is operably linked to a coding sequence if it affects the transcription of the coding sequence. Operably linked means that the DNA sequences being linked are typically contiguous and, where necessary to join two protein encoding regions, contiguous and in reading frame. Linking can be accomplished by ligation at convenient restriction sites or at adapters or linkers inserted in lieu thereof, or by gene synthesis.

microRNA

As used herein, "microRNA" or "miRNA" or "miR" has its customary and ordinary meaning as understood by one of skill in the art in view of this disclosure. A microRNA is a small non-coding RNA molecule found in plants, animals and some viruses, that may function in RNA silencing and post-transcriptional regulation of gene expression. A target sequence of a microRNA may be denoted as "miRT". For example, a target sequence of microRNA-1 or miRNA-1 or miR-1 may be denoted as miRT-1.

Proteins and Amino Acids

The terms "protein" or "polypeptide" or "amino acid sequence" are used interchangeably and refer to molecules consisting of a chain of amino acids, without reference to a specific mode of action, size, 3-dimensional structure or origin. In amino acid sequences as described herein, amino acids or "residues" are denoted by three-letter symbols. These three-letter symbols as well as the corresponding one-letter symbols are well known to a person of skill in the art and have the following meaning: A (Ala) is alanine, C (Cys) is cysteine, D (Asp) is aspartic acid, E (Glu) is glutamic acid, F (Phe) is phenylalanine, G (Gly) is glycine, H (His) is histidine, I (Ile) is isoleucine, K (Lys) is lysine, L (Leu) is leucine, M (Met) is methionine, N (Asn) is asparagine, P (Pro) is proline, Q (Gln) is glutamine, R (Arg) is arginine, S (Ser) is serine, T (Thr) is threonine, V (Val) is valine, W (Trp) is tryptophan, Y (Tyr) is tyrosine. A residue may be any proteinogenic amino acid, but also any non-proteinogenic amino acid such as D-amino acids and modified amino acids formed by post-translational modifications, and also any non-natural amino acid.

CNS and Brain

As used herein, "central nervous system" or "CNS" refers to the part of the nervous system that comprises the brain and the spinal cord, to which sensory impulses are transmitted and from which motor impulses pass out, and which coordinates the activity of the entire nervous system.

As used herein, "brain" refers to the central organ of the nervous system and consists of the cerebrum, the brainstem and the cerebellum. It controls most of the activities of the body, processing, integrating, and coordinating the information it receives from the sense organs, and making decisions as to the instructions sent to the rest of the body.

In particular, as used herein, 'hypothalamus" refers to a region of the forebrain below the thalamus which coordinates both the autonomic nervous system and the activity of the pituitary, controlling body temperature, thirst, hunger, and other homeostatic systems, and involved in sleep and emotional activity.

Gene Constructs

Gene constructs as described herein could be prepared using any cloning and/or recombinant DNA techniques, as known to a person of skill in the art, in which a nucleotide sequence encoding said FGF21 is expressed in a suitable cell, e.g. cultured cells or cells of a multicellular organism, such as described in Ausubel et al., "Current Protocols in Molecular Biology", Greene Publishing and Wiley-Interscience, New York (1987) and in Sambrook and Russell (2001, supra); both of which are incorporated herein by reference in their entirety. Also see, Kunkel (1985) Proc. Natl. Acad. Sci. 82:488 (describing site directed mutagenesis) and Roberts et al. (1987) Nature 328:731-734 or Wells, J. A., et al. (1985) Gene 34: 315 (describing cassette mutagenesis).

Expression Vectors

The phrase "expression vector" or "vector" generally refers to a nucleotide sequence that is capable of effecting expression of a gene or a coding sequence in a host compatible with such sequences. An expression vector carries a genome that is able to stabilize and remain episomal in a cell. Within the context of the invention, a cell may mean to encompass a cell used to make the construct or a cell wherein the construct will be administered. Alternatively, a vector is capable of integrating into a cell's genome, for example through homologous recombination or otherwise.

These expression vectors typically include at least suitable promoter sequences and optionally, transcription termination signals. An additional factor necessary or helpful in effecting expression can also be used as described herein. A nucleic acid or DNA or nucleotide sequence encoding a FGF21 is incorporated into a DNA construct capable of introduction into and expression in an in vitro cell culture. Specifically, a DNA construct is suitable for replication in a prokaryotic host, such as bacteria, e.g., *E. coli*, or can be introduced into a cultured mammalian, plant, insect, (e.g., Sf9), yeast, fungi or other eukaryotic cell lines.

A DNA construct prepared for introduction into a particular host may include a replication system recognized by the host, an intended DNA segment encoding a desired polypeptide, and transcriptional and translational initiation and termination regulatory sequences operably linked to the polypeptide-encoding segment. The term "operably linked" has already been described herein. For example, a promoter or enhancer is operably linked to a coding sequence if it stimulates the transcription of the sequence. DNA for a signal sequence is operably linked to DNA encoding a polypeptide if it is expressed as a preprotein that participates in the secretion of a polypeptide. Generally, a DNA sequence that is operably linked are contiguous, and, in the case of a signal sequence, both contiguous and in reading frame. However, enhancers need not be contiguous with a coding sequence whose transcription they control. Linking is accomplished by ligation at convenient restriction sites or at adapters or linkers inserted in lieu thereof, or by gene synthesis.

The selection of an appropriate promoter sequence generally depends upon the host cell selected for the expression of a DNA segment. Examples of suitable promoter sequences include prokaryotic, and eukaryotic promoters well known in the art (see, e.g. Sambrook and Russell, 2001, supra). A transcriptional regulatory sequence typically includes a heterologous enhancer or promoter that is recognised by the host. The selection of an appropriate promoter depends upon the host, but promoters such as the trp, lac and phage promoters, tRNA promoters and glycolytic enzyme promoters are known and available (see, e.g. Sambrook and Russell, 2001, supra). An expression vector includes the replication system and transcriptional and translational regulatory sequences together with the insertion site for the polypeptide encoding segment. In most cases, the replication system is only functional in the cell that is used to make the vector (bacterial cell as *E. Coli*). Most plasmids and vectors do not replicate in the cells infected with the vector. Examples of workable combinations of cell lines and expression vectors are described in Sambrook and Russell (2001, supra) and in Metzger et al. (1988) Nature 334: 31-36. For example, suitable expression vectors can be expressed in, yeast, e.g. *S. cerevisiae*, e.g., insect cells, e.g., Sf9 cells, mammalian cells, e.g., CHO cells and bacterial cells, e.g., *E. coli*. A cell may thus be a prokaryotic or eukaryotic host cell. A cell may be a cell that is suitable for culture in liquid or on solid media.

Alternatively, a host cell is a cell that is part of a multicellular organism such as a transgenic plant or animal.

The selection of an appropriate promoter sequence generally depends upon the host cell selected for the expression of a DNA segment. Examples of suitable promoter sequences include prokaryotic, and eukaryotic promoters well known in the art (see, e.g. Sambrook and Russell, 2001, supra). A transcriptional regulatory sequence typically includes a heterologous enhancer or promoter that is recognised by the host. The selection of an appropriate promoter depends upon the host, but promoters such as the trp, lac and phage promoters, tRNA promoters and glycolytic enzyme promoters are known and available (see, e.g. Sambrook and Russell, 2001, supra). An expression vector includes the replication system and transcriptional and translational regulatory sequences together with the insertion site for the polypeptide encoding segment. In most cases, the replication system is only functional in the cell that is used to make the vector (bacterial cell as *E. Coli*). Most plasmids and vectors do not replicate in the cells infected with the vector. Examples of workable combinations of cell lines and expression vectors are described in Sambrook and Russell (2001, supra) and in Metzger et al. (1988) Nature 334: 31-36. For example, suitable expression vectors can be expressed in yeast, e.g. *S. cerevisiae*, e.g., insect cells, e.g., Sf9 cells, mammalian cells, e.g., CHO cells and bacterial cells, e.g., *E. coli*. A cell may thus be a prokaryotic or eukaryotic host cell. A cell may be a cell that is suitable for culture in liquid or on solid media.

Alternatively, a host cell is a cell that is part of a multicellular organism such as a transgenic plant or animal.

Viral Vector

A viral vector or a viral expression vector a viral gene therapy vector is a vector that comprises a gene construct as described herein.

A viral vector or a viral gene therapy vector is a vector that is suitable for gene therapy. Vectors that are suitable for gene therapy are described in Anderson 1998, Nature 392: 25-30; Walther and Stein, 2000, Drugs 60: 249-71; Kay et al., 2001, Nat. Med. 7: 33-40; Russell, 2000, J. Gen. Virol. 81: 2573-604; Amado and Chen, 1999, Science 285: 674-6; Federico, 1999, Curr. Opin. Biotechnol. 10: 448-53; Vigna and Naldini, 2000, J. Gene Med. 2: 308-16; Marin et al., 1997, Mol. Med. Today 3: 396-403; Peng and Russell, 1999, Curr. Opin. Biotechnol. 10: 454-7; Sommerfelt, 1999, J. Gen. Virol. 80: 3049-64; Reiser, 2000, Gene Ther. 7: 910-3; and references cited therein.

A particularly suitable gene therapy vector includes an adenoviral and adeno-associated virus (AAV) vector. These vectors infect a wide number of dividing and non-dividing cell types including synovial cells and liver cells. The episomal nature of the adenoviral and AAV vectors after cell entry makes these vectors suited for therapeutic applications, (Russell, 2000, J. Gen. Virol. 81: 2573-2604; Goncalves, 2005, Virol J. 2(1):43) as indicated above. AAV vectors are even more preferred since they are known to result in very stable long-term expression of transgene expression (up to 9 years in dog (Niemeyer et al, Blood. 2009 Jan. 22; 113(4):797-806) and ~10 years in human (Buchlis, G. et al., Blood. 2012 Mar. 29; 119(13):3038-41). Preferred adenoviral vectors are modified to reduce the host response as reviewed by Russell (2000, supra). Method for gene therapy using AAV vectors are described by Wang et al., 2005, J Gene Med. March 9 (Epub ahead of print), Mandel et al., 2004, Curr Opin Mol Ther. 6(5):482-90, and Martin et al., 2004, Eye 18(11):1049-55, Nathwani et al, N Engl J Med. 2011 Dec. 22; 365(25):2357-65, Apparailly et al, Hum Gene Ther. 2005 April; 16(4):426-34.

Another suitable gene therapy vector includes a retroviral vector. A preferred retroviral vector for application in the present invention is a lentiviral based expression construct. Lentiviral vectors have the ability to infect and to stably integrate into the genome of dividing and non-dividing cells (Amado and Chen, 1999 Science 285: 674-6). Methods for the construction and use of lentiviral based expression constructs are described in U.S. Pat. Nos. 6,165,782, 6,207, 455, 6,218,181, 6,277,633 and 6,323,031 and in Federico (1999, Curr Opin Biotechnol 10: 448-53) and *Vigna* et al. (2000, J Gene Med 2000; 2: 308-16).

Other suitable gene therapy vectors include an adenovirus vector, a herpes virus vector, a polyoma virus vector or a vaccinia virus vector.

Adeno-Associated Virus Vector (AAV Vector)

The terms "adeno associated virus", "AAV virus", "AAV virion", "AAV viral particle" and "AAV particle", used as synonyms herein, refer to a viral particle composed of at least one capsid protein of AAV (preferably composed of all capsid protein of a particular AAV serotype) and an encapsulated polynucleotide of the AAV genome. If the particle comprises a heterologous polynucleotide (i.e. a polynucleotide different from a wild-type AAV genome, such as a transgene to be delivered to a mammalian cell) flanked by AAV inverted terminal repeats, then they are typically known as a "AAV vector particle" or "AAV viral vector" or "AAV vector". AAV refers to a virus that belongs to the genus Dependovirus family Parvoviridae. The AAV genome is approximately 4.7 Kb in length and it consists of single strand deoxyribonucleic acid (ssDNA) that can be positive or negative detected. The invention also encompasses the use of double stranded AAV also called dsAAV or scAAV. The genome includes inverted terminal repeats (ITR) at both ends of the DNA strand, and two open reading frames (ORFs): rep and cap. The frame rep is made of four overlapping genes that encode proteins Rep necessary for AAV lifecycle. The frame cap contains nucleotide sequences overlapping with capsid proteins: VP1, VP2 and VP3, which interact to form a capsid of icosahedral symmetry (see Carter and Samulski 2000, and Gao et al, 2004).

A preferred viral vector or a preferred gene therapy vector is an AAV vector. An AAV vector as used herein preferably comprises a recombinant AAV vector (rAAV vector). A "rAAV vector" as used herein refers to a recombinant vector comprising part of an AAV genome encapsidated in a protein shell of capsid protein derived from an AAV serotype as explained herein. Part of an AAV genome may contain the inverted terminal repeats (ITR) derived from an adeno-associated virus serotype, such as AAV1, AAV2, AAV3, AAV4, AAV5 and others. Preferred ITRs are those of AAV2 which are represented by sequences comprising, consisting essentially of, or consisting of SEQ ID NO: 30 (5' ITR) and SEQ ID NO: 31 (3' ITR). The invention also preferably encompasses the use of a sequence having at least 80% (or at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100%) identity with SEQ ID NO: 30 as 5' ITR and a sequence having at least 80% (or at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100%) identity with SEQ ID NO: 31 as 3' ITR.

Protein shell comprised of capsid protein may be derived from any AAV serotype. A protein shell may also be named a capsid protein shell. rAAV vector may have one or preferably all wild type AAV genes deleted, but may still comprise functional ITR nucleic acid sequences. Functional ITR sequences are necessary for the replication, rescue and packaging of AAV virions. The ITR sequences may be wild type sequences or may have at least 80%, at least 85%, at least 90%, at least 95%, at least 97%, at least 98%, at least 99% or 100% sequence identity with wild type sequences or may be altered by for example by insertion, mutation, deletion or substitution of nucleotides, as long as they remain functional. In this context, functionality refers to the ability to direct packaging of the genome into the capsid shell and then allow for expression in the host cell to be infected or target cell. In the context of the present invention a capsid protein shell may be of a different serotype than the rAAV vector genome ITR.

A nucleic acid molecule represented by a nucleic acid sequence of choice is preferably inserted between the rAAV genome or ITR sequences as identified above, for example an expression construct comprising an expression regulatory element operably linked to a coding sequence and a 3' termination sequence. Said nucleic acid molecule may also be called a transgene.

"AAV helper functions" generally refers to the corresponding AAV functions required for rAAV replication and packaging supplied to the rAAV vector in trans. AAV helper functions complement the AAV functions which are missing in the rAAV vector, but they lack AAV ITRs (which are provided by the rAAV vector genome). AAV helper functions include the two major ORFs of AAV, namely the rep coding region and the cap coding region or functional substantially identical sequences thereof. Rep and Cap regions are well known in the art, see e.g. Chiorini et al. (1999, J. of Virology, Vol 73(2): 1309-1319) or U.S. Pat. No. 5,139,941, incorporated herein by reference. The AAV helper functions can be supplied on an AAV helper construct. Introduction of the helper construct into the host cell can occur e.g. by transformation, transfection, or transduction prior to or concurrently with the introduction of the rAAV genome present in the rAAV vector as identified herein. The AAV helper constructs of the invention may thus be chosen such that they produce the desired combination of serotypes for the rAAV vector's capsid protein shell on the one hand and for the rAAV genome present in said rAAV vector replication and packaging on the other hand.

"AAV helper virus" provides additional functions required for AAV replication and packaging. Suitable AAV helper viruses include adenoviruses, herpes simplex viruses (such as HSV types 1 and 2) and vaccinia viruses. The additional functions provided by the helper virus can also be introduced into the host cell via plasmids, as described in U.S. Pat. No. 6,531,456 incorporated herein by reference.

"Transduction" refers to the delivery of a FGF21 into a recipient host cell by a viral vector. For example, transduction of a target cell by a rAAV vector of the invention leads to transfer of the rAAV genome contained in that vector into the transduced cell. "Host cell" or "target cell" refers to the cell into which the DNA delivery takes place, such as the muscle cells of a subject. AAV vectors are able to transduce both dividing and non-dividing cells.

Production of an AAV Vector

The production of recombinant AAV (rAAV) for vectorizing transgenes have been described previously. See Ayuso E, et al., Curr. Gene Ther. 2010; 10:423-436, Okada T, et al., Hum. Gene Ther. 2009; 20:1013-1021, Zhang H, et al., Hum. Gene Ther. 2009; 20:922-929, and Virag T, et al., Hum. Gene Ther. 2009; 20:807-817. These protocols can be used or adapted to generate the AAV of the invention. In one embodiment, the producer cell line is transfected transiently with the polynucleotide of the invention (comprising the expression cassette flanked by ITRs) and with construct(s) that encodes rep and cap proteins and provides helper functions. In another embodiment, the cell line supplies stably the helper functions and is transfected transiently with the polynucleotide of the invention (comprising the expression cassette flanked by ITRs) and with construct(s) that encodes rep and cap proteins. In another embodiment, the cell line supplies stably the rep and cap proteins and the helper functions and is transiently transfected with the polynucleotide of the invention. In another embodiment, the cell line supplies stably the rep and cap proteins and is transfected transiently with the polynucleotide of the invention and a polynucleotide encoding the helper functions. In yet another embodiment, the cell line supplies stably the polynucleotide of the invention, the rep and cap proteins and the helper functions. Methods of making and using these and other AAV production systems have been described in the art. See Muzyczka N, et al., U.S. Pat. No. 5,139,941, Zhou X, et al., U.S. Pat. No. 5,741,683, Samulski R, et al., U.S. Pat. No. 6,057,152, Samulski R, et al., U.S. Pat. No. 6,204,059, Samulski R, et al., U.S. Pat. No. 6,268,213, Rabinowitz J, et al., U.S. Pat. No. 6,491,907, Zolotukhin S, et al., U.S. Pat. No. 6,660,514, Shenk T, et al., U.S. Pat. No. 6,951,753, Snyder R, et al., U.S. Pat. No. 7,094,604, Rabinowitz J, et al., U.S. Pat. No. 7,172,893, Monahan P, et al., U.S. Pat. No. 7,201,898, Samulski R, et al., U.S. Pat. No. 7,229,823, and Ferrari F, et al., U.S. Pat. No. 7,439,065.

The rAAV genome present in a rAAV vector comprises at least the nucleotide sequences of the inverted terminal repeat regions (ITRs) of one of the AAV serotypes (preferably the ones of serotype AAV2 as disclosed earlier herein), or nucleotide sequences substantially identical thereto or nucleotide sequences having at least 60% identity thereto, and nucleotide sequence encoding a FGF21 (under control of a suitable regulatory element) inserted between the two ITRs. A vector genome requires the use of flanking 5' and a 3' ITR sequences to allow for efficient packaging of the vector genome into the rAAV capsid.

The complete genome of several AAV serotypes and corresponding ITR has been sequenced (Chiorini et al. 1999, J. of Virology Vol. 73, No. 2, p 1309-1319). They can be either cloned or made by chemical synthesis as known in the art, using for example an oligonucleotide synthesizer as supplied e.g. by Applied Biosystems Inc. (Fosters, CA, USA) or by standard molecular biology techniques. The ITRs can be cloned from the AAV viral genome or excised from a vector comprising the AAV ITRs. The ITR nucleotide sequences can be either ligated at either end to the nucleotide sequence encoding one or more therapeutic proteins using standard molecular biology techniques, or the AAV sequence between the ITRs can be replaced with the desired nucleotide sequence.

Preferably, the rAAV genome as present in a rAAV vector does not comprise any nucleotide sequences encoding viral proteins, such as the rep (replication) or cap (capsid) genes of AAV. This rAAV genome may further comprise a marker or reporter gene, such as a gene for example encoding an antibiotic resistance gene, a fluorescent protein (e.g. gfp) or a gene encoding a chemically, enzymatically or otherwise detectable and/or selectable product (e.g. lacZ, aph, etc.) known in the art.

The rAAV genome as present in said rAAV vector further comprises a promoter sequence operably linked to the nucleotide sequence encoding a FGF21.

A suitable 3' untranslated sequence may also be operably linked to the nucleotide sequence encoding a FGF21. Suitable 3' untranslated regions may be those naturally associated with the nucleotide sequence or may be derived from different genes, such as for example the SV40 polyadenylation signal (SEQ ID NO: 32) and the rabbit β-globin polyadenylation signal (SEQ ID NO: 33).

Expression

Expression may be assessed by any method known to a person of skill in the art. For example, expression may be assessed by measuring the levels of transgene expression in the liver on the level of the mRNA or the protein by standard assays known to a person of skill in the art, such as qPCR, Western blot analysis or ELISA.

Expression may be assessed at any time after administration of the gene construct, expression vector or composition as described herein. In some embodiments herein, expression may be assessed after 1 week, 2 weeks, 3 weeks, 4, weeks, 5 weeks, 6 weeks, 7 weeks, 8 weeks, 9, weeks, 10 weeks, 11 weeks, 12 weeks, 14 weeks, 16 weeks, 18 weeks, 20 weeks, 22 weeks, 24 weeks, 28 weeks, 32 weeks, 36 weeks, 40 weeks, or more.

In the context of the invention, CNS- and/or brain- and/or hypothalamus and/or cortex- and/or hippocampus- and/or cerebellum- and/or olfactory bulb-specific expression refers to the preferential or predominant (at least 10% higher, at least 20% higher, at least 30% higher, at least 40% higher, at least 50% higher, at least 60% higher, at least 70% higher, at least 80% higher, at least 90% higher, at least 100% higher, at least 150% higher, at least 200% higher or more) expression of FGF21 in the CNS and/or the brain and/or the hypothalamus and/or the cortex and/or the hippocampus and/or the cerebellum and/or the olfactory bulb as compared to other organs or tissues. Other organs or tissues may be the liver, pancreas, adipose tissue, skeletal muscle, heart, kidney, colon, hematopoietic tissue, lung, ovary, spleen, stomach, testis and others. Preferably, other organs are the liver and/or the heart. In an embodiment, expression is not detectable in the liver, pancreas, adipose tissue, skeletal muscle and/or heart. In some embodiments, expression is not detectable in at least one, at least two, at least three, at least four or all organs selected from the group consisting of the liver, pancreas, adipose tissue, skeletal muscle, heart, kidney, colon, hematopoietic tissue, lung, ovary, spleen, stomach and testis. Expression may be assessed as described above.

Throughout the application, where CNS- and/or brain- and/or hypothalamus and/or cortex- and/or hippocampus- and/or cerebellum- and/or olfactory bulb-specific is mentioned in the context of expression, cell-type specific expression of the cell type(s) making up the CNS and/or the brain and/or the hypothalamus and/or the cortex and/or the hippocampus and/or the cerebellum and/or the olfactory bulb is also envisaged, respectively.

Administration

As used herein, "intra-CSF administration" means direct administration into the CSF, located in the subarachnoid space between the arachnoid and pia mater layers of the meninges surrounding the brain. Intra-CSF administration can be performed via intra-cisterna magna, intraventricular or intrathecal administration. As used herein, "intra-cisterna magna administration" means administration into the cisterna magna, an opening of the subarachnoid space located between the cerebellum and the dorsal surface of the medulla oblongata. As used herein, "intraventricular administration" means administration into the either of both lateral ventricles of the brain As used herein, "intrathecal administration" involves the direct administration into the CSF within the intrathecal space of the spinal column. As used herein, "intraparenchymal administration" means local administration directly into any region of the brain parenchyma. As used herein, "intranasal administration" means administration by way of the nasal structures.

Codon Optimization

"Codon optimization", as used herein, refers to the processes employed to modify an existing coding sequence, or to design a coding sequence, for example, to improve translation in an expression host cell or organism of a transcript RNA molecule transcribed from the coding sequence, or to improve transcription of a coding sequence. Codon optimization includes, but is not limited to, processes including selecting codons for the coding sequence to suit the codon preference of the expression host organism. For example, to suit the codon preference of mammalians, preferably of murine, canine or human expression hosts. Codon optimization also eliminates elements that potentially impact negatively RNA stability and/or translation (e. g. termination sequences, TATA boxes, splice sites, ribosomal entry sites, repetitive and/or GC rich sequences and RNA secondary structures or instability motifs).). In some embodiments, codon-optimized sequences show at least 3%, 5%, 10%, 15%, 20%, 25%, 30%, 40%, 50%, 60%, 70%, 80%, 90%, 100% or more increase in transcription, RNA stability and/or translation.

In this document and in its claims, the verb "to comprise" and its conjugations is used in its non-limiting sense to mean that items following the word are included, but items not specifically mentioned are not excluded. In addition, the verb "to consist" may be replaced by "to consist essentially of" meaning that a peptide or peptidomimetic, a culture medium, or a composition as described herein may comprise additional component(s) than the ones specifically identified, said additional component(s) not altering the unique characteristic of the invention. In addition, the verb "to consist" may be replaced by "to consist essentially of" meaning that a method as described herein may comprise additional step(s) than the ones specifically identified, said additional step(s) not altering the unique characteristic of the invention.

Reference to an element by the indefinite article "a" or "an" does not exclude the possibility that more than one of the element is present, unless the context clearly requires that there be one and only one of the elements. The indefinite article "a" or "an" thus usually means "at least one".

As used herein, "at least" a particular value means that particular value or more. For example, "at least 2" is understood to be the same as "2 or more" i.e., 2, 3, 4, 5, 6, 7, 8, 9, 10, 11, 12, 13, 14, 15, . . . , etc.

Individual numerical values are stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. In the absence of any contrary consideration, the word "about" or "approximately" when used in association with a numerical value (e.g. about 10) preferably means that the value may be the given value (of 10) more or less 1% of the value.

As used herein, the term "and/or" indicates that one or more of the stated cases may occur, alone or in combination with at least one of the stated cases, up to with all of the stated cases.

Each embodiment as identified herein may be combined together unless otherwise indicated.

All patent applications, patents, and printed publications cited herein are incorporated herein by reference in the entireties, except for any definitions, subject matter disclaimers or disavowals, and except to the extent that the incorporated material is inconsistent with the express disclosure herein, in which case the language in this disclosure controls.

A person of skill in the art will recognize many methods and materials similar or equivalent to those described herein, which could be used in the practice of the present invention. Indeed, the present invention is in no way limited to the methods and materials described.

The present invention is further described by the following examples which should not be construed as limiting the scope of the invention.

DESCRIPTION OF THE FIGURES

FIG. 3. Reversal of diabetes in db/db mice by intra-CSF administration of AAV9-FGF21 vectors. Evolution of fed blood glucose levels of non-treated and AAV9-CAG-moFGF21-dmiRT-treated db/db mice after intra-CSF vector administration. Results are expressed as the mean±SEM, n=9 animals/group. ***p<0.001 vs non-treated mice.

FIG. 13. Reduced inflammation in adipose tissue and liver of db/db mice after treatment with AAV9-FGF21 vectors. (A) Representative images of MAC-2 immunohistochemistry of the eWAT from non-treated and AAV9-FGF21-treated db/db mice (n=6 animals/group) (B) Expression levels of the inflammatory marker F4/80 was measured by RTqPCR in eWAT of db/db mice, and normalized with Rplp0 values. Analyses were performed 12 weeks after intra-CSF administration of 5×10$^{10}$ vg/mouse of AAV9-CAG-moFGF21-dmiRT vectors. (C-D) Expression levels of the inflammatory markers F4/80, Il6 and Tnfa were measured by RTqPCR in BAT (C) and liver (D) of db/db mice, and normalized with Rplp0 values. Analyses were performed 12 weeks after intra-CSF administration of 5×10$^{10}$ vg/mouse of AAV9-CAG-moFGF21-dmiRT vectors. Results are expressed as the mean±SEM, n=9 animals/group. * p<0.05,  p<0.01 and *p<0.001 ***p<0.001 vs non-treated mice. F4/80, adhesion G protein-coupled receptor E1; Il6, interleukin 6; Tnfa, tumor necrosis factor alpha; eWAT, epididymal white adipose tissue; BAT, brown adipose tissue. MAC-2, lectin, galactose binding, soluble 3; Arrows indicate MAC-2 signalling.

Figure 18:
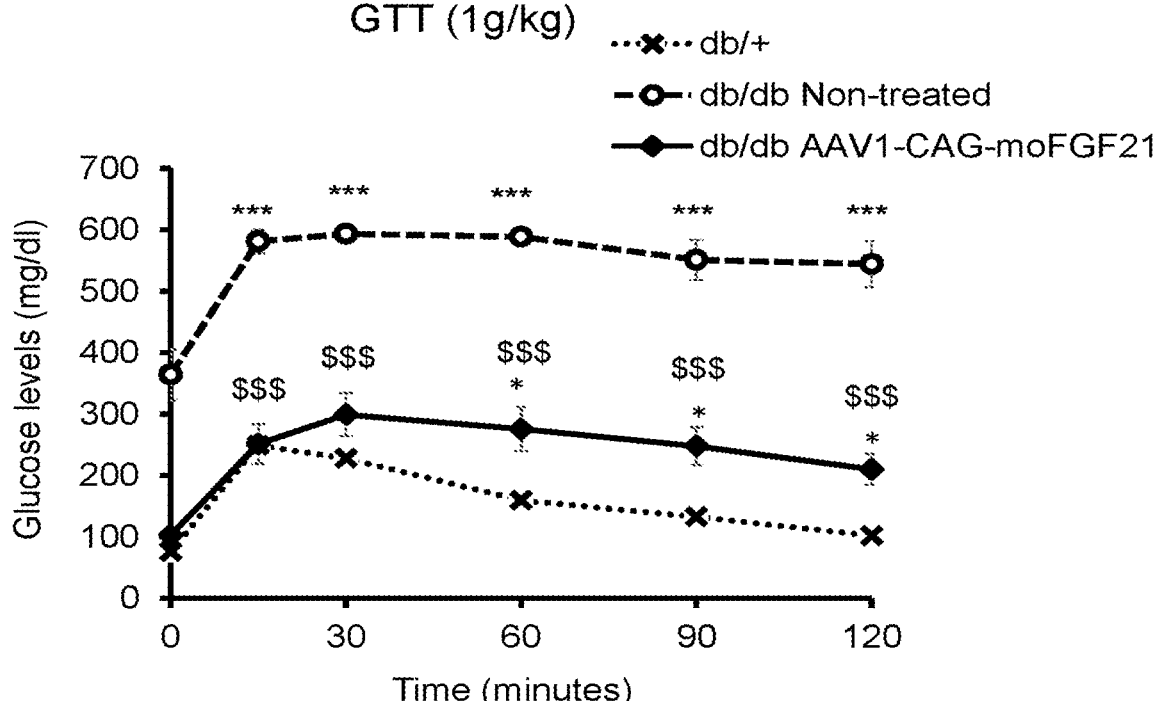

FIG. 18. Treatment with AAV1-CAG-FGF21 improves glucose tolerance. Glucose tolerance was studied 11 weeks after AAV administration in non-treated db/+(lean), non-treated db/db and AAV1-CAG-FGF21-treated db/db mice after an intraperitoneal injection of glucose (1 g/kg body weight). Results are expressed as the mean±SEM, n=7 animals/group. *p<0.05 and *** p<0.001 vs db/+ mice. $$$p<0.001 vs db/db non-treated mice.

Figure 19:
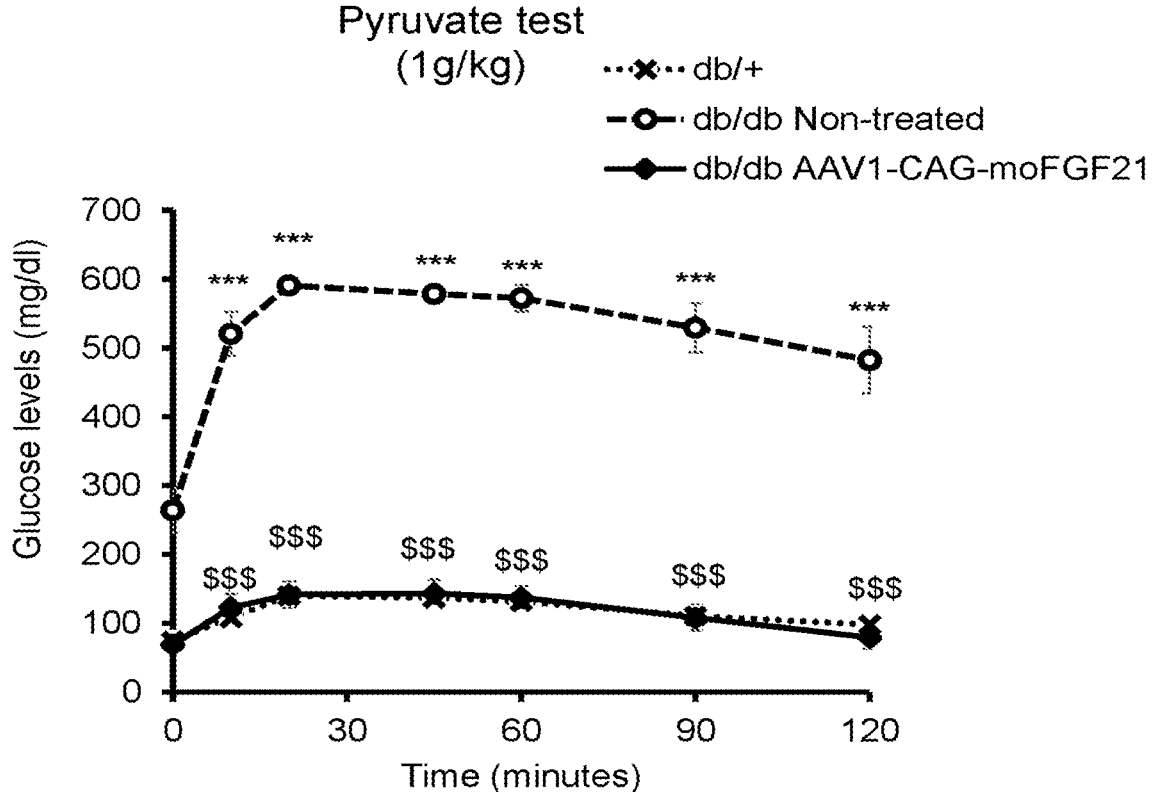

FIG. 19. Decreased gluconeogenesis in db/db mice after AAV1-FGF21 administration. A pyruvate tolerance test was performed in lean (db/+), non-treated and AAV9-CAG-moFGF21-dmiRT-treated db/db mice. All groups were given an intraperitoneal injection of pyruvate (1 g/kg body weight) and blood glucose levels were measured at the indicated time points. The test was performed 12 weeks post-AAV administration. Results are expressed as the mean±SEM, n=7 animals/group. ***p<0.001 vs non-treated mice. $$$p<0.001 vs db/db non-treated mice.

EXAMPLES

To study the effects of FGF21 in the brain when overexpressed in this organ by using AAV vectors. Three different experiments have been performed:

Treatment of db/db mice with AAV9-CAG-moFGF21-dmiRT. Dose used: 5×10$^{10}$ vg/mouse (Example 1).

Treatment of SAMP8 mice with AAV9-CAG-moFGF21-dmiRT. Dose used: 5×10$^{10}$ vg/mouse (Example 2).

Treatment of db/db mice with AAV1-CAG-moFGF21. Dose used: 5×10$^{10}$ vg/mouse (Example 4).

Moreover, we also examined brain transduction efficiency by AAV1-FGF21, AAV2-FGF21 and AAV9-FGF21 vectors after intra-CSF administration of wild-type mice (Example 3).

dmiRT refers to 4 copies of the miRT-122a and 4 copies of the miRT-1 sequences.

The CAG-moFGF21-dmiRT gene construct sequence is comprised in the sequence of SEQ ID NO: 35. The CAG-moFGF21 gene construct sequence is comprised in the sequence of SEQ ID NO: 46.

General Procedures to the Examples

Subject Characteristics

Male BKS.Cg-+Lepr$^{db}$/+Lepr$^{db}$ OlaHsd (db/db), BKS.Cg-m+/+Lepr$^{db}$/OlaHsd (db/+, lean) SAMP8/TaHsd (SAMP8) and C57Bl/6J (wild-type) mice were used. Mice were fed ad libitum with a standard diet (2018S Teklad Global Diets®, Harlan Labs., Inc., Madison, Wis., US and kept under a light-dark cycle of 12 h (lights on at 8:00 a.m.) and stable temperature (22° C.±2). For tissue sampling, mice were anesthetized by means of inhalational anesthetic isoflurane (IsoFlo®, Abbott Laboratories, Abbott Park, Ill., US) and decapitated. Tissues of interest were excised and kept at −80° C. until analysis. All experimental procedures were approved by the Ethics Committee for Animal and Human Experimentation of the Universitat Autònoma de Barcelona.

Recombinant AAV Vectors

Single-stranded AAV vectors of serotype 1, 2 and 9 were produced by triple transfection of HEK293 cells according to standard methods (Ayuso, E. et al., 2010. Curr Gene Ther. 10(6):423-36). Cells were cultured in 10 roller bottles (850 cm$^2$, flat; Corning™, Sigma-Aldrich Co., Saint Louis, Mo., US) in DMEM 10% FBS to 80% confluence and co-transfected by calcium phosphate method with a plasmid carrying the expression cassette flanked by the AAV2 ITRs (SEQ ID NO: 35), a helper plasmid carrying the AAV2 rep gene and the AAV of serotype 1, 2 or 9 cap gene, respectively, and a plasmid carrying the adenovirus helper functions. The transgene used was the murine codon-optimized FGF21 coding-sequence (SEQ ID NO: 9) driven by the early enhancer/chicken beta actin (CAG) promoter (SEQ ID NO: 27). In examples 1, 2 and 3 the transgene also contained the addition of four tandem repeats of the miRT-122a sequence (5'CAAACACCATTGTCACACTCCA3', SEQ ID NO: 12) and four tandems repeats of the miRT-1 sequence (5'TTA-CATACTTCTTTACATTCCA3', SEQ ID NO: 13) cloned in the 3' untranslated region of the expression cassette. In example 4, the cassette was not carrying the miRT-122a and miRT-1; AAVs were purified with an optimized method based on a polyethylene glycol precipitation step and two consecutive cesium chloride (CsCl) gradients. This second-generation CsCl-based protocol reduced empty AAV capsids and DNA and protein impurities dramatically (Ayuso, E. et al., 2010. *Curr Gene Ther.* 10(6):423-36). Purified AAV vectors were dialyzed against PBS, filtered and stored at −80° C. Titers of viral genomes were determined by quantitative PCR following the protocol described for the AAV2 reference standard material using linearized plasmid DNA as standard curve (Lock M, et al., Hum. Gene Ther. 2010; 21:1273-1285). The vectors were constructed according to molecular biology techniques well known in the art.

In Vivo Intra-CSF Administration of AAV Vectors

Mice were anesthetized with an intraperitoneal injection of ketamine (100 mg/kg) and xylazine (10 mg/kg), and the skin of the posterior part of the head, from behind the ears to approximately between the scapulas, was shaved and rinsed with ethanol. Mice were held in prone position, with the head at a slightly downward inclination. A 2-mm rostro-caudal incision was made to introduce a Hamilton syringe at an angle of 45-55° into the cisterna magna, between the occiput and the C1-vertebra and 5 μl of vector dilution was administered. Given that the CNS is the main target compartment for vector delivery, mice were dosed with the same number of vector genomes/mouse irrespective of body weight ($5×10^{10}$ vg/mice).

Immunohistochemical and Morphometric Analysis

Tissues were fixed for 24 h in formalin (Panreac Química), embedded in paraffin, and sectioned. Tissue samples were stained with hematoxylin-eosin and images were taken with the Nikon Eclipse E800 microscope (Nikon, Tokyo, Japan) connected to a videocamera with a monitor with an image analysis software (analySIS 3.0; Soft Imaging System, Center Valley, Pa., EEUU).

Immunohistochemistry

Tissues were fixed for 12-24 h in 10% formalin, embedded in paraffin and sectioned. For immunohistochemical detection, sections were deparaffinised and incubated overnight at 4° C. with rat anti-MAC2 (1:50; CL8942AP; Cedarlane) and guinea pig anti-insulin (1:100; 1-8510; Sigma-Aldrich). Biotinylated rabbit anti-rat (1:300; E0467; Dako) and rabbit anti-guinea pig coupled to peroxidase (1:300; P0141; Dako) were used as secondary antibodies. The ABC peroxidase kit (Pierce) was used for immunodetection, and sections were counterstained in Mayer's hematoxylin. The percentage of β-cell area in the pancreas was analyzed in two insulin-stained sections 200 μm apart, by dividing the area of all insulin positive cells in one section by the total pancreas area of that section. β-cell mass was calculated by multiplying pancreas weight by percentage of β-cell area, as previously described (Casellas et al, 2006).

RNA Analysis

Total RNA was obtained from hypothalamus, cortex, hippocampus, cerebellum and olfactory bulb using Tripure isolation reagent (Roche Diagnostics Corp., Indianapolis, Ind., US) and from white adipose tissue, brown adipose tissue and liver using Qiazol lysis reagent (Qiagen NV, Venlo, NL), and RNeasy Mini Kit or RNeasy Micro Kit for hippocampus samples (Qiagen NV, Venlo, NL). In order to eliminate the residual viral genomes, total RNA was treated with DNAseI (Qiagen NV, Venlo, NL). For RT-PCR analysis, 1 μg of RNA samples was reverse-transcribed using Transcriptor First Strand cDNA Synthesis Kit (04379012001, Roche, Calif., USA). Real-time quantitative PCR was performed in a SmartCyclerII® (Cepheid, Sunnyvale, USA) using TB Green Premix Ex TaqII (Takara Bio Europe, France). Data was normalized with Rplp0 values and analyzed as previously described (Pfaffl, M., Nucleic Acids Res. 2001; 29(9):e45).

An overview of the primers used is shown below:

```
moFgf21-Fw:
                              (SEQ ID NO: 47)
5'-CCTAACCAGGACGCCACAAG-3' moFgf21-Rv:
                              (SEQ ID NO: 48)
5'-GTTCCACCATGCTCAGAGGG-3'

Gfap-Fw:
                              (SEQ ID NO: 49)
5'-ACAGACTTTCTCCAACCTCCAG-3'

Gfap-Rv:
                              (SEQ ID NO: 50)
5'-CCTTCTGACACGGATTTGGT-3'

S100b-Fw:
                              (SEQ ID NO: 51)
5'-AACAACGAGCTCTCTCACTTCC-3'

S100b-Rv:
                              (SEQ ID NO: 52)
5'-CGTCTCCATCACTTTGTCCA-3'

Aif1-Fw:
                              (SEQ ID NO: 53)
5'-TGAGCCAAAGCAGGGATTTG-3'

Aif1-Rv:
                              (SEQ ID NO: 54)
5'-TCAAGTTTGGACGGCAGATC-3'

Nfkb-Fw:
                              (SEQ ID NO: 55)
5'-GACCACTGCTCAGGTCCACT-3'

Nfkb-Rv:
                              (SEQ ID NO: 56)
5'-TGTCACTATCCCGGAGTTCA-3'

Il1b-Fw:
                              (SEQ ID NO: 57)
5'-ATGAAGGGCTGCTTCCAAAC-3'

Il1b-Rv:
                              (SEQ ID NO: 58)
5'-ATGTGCTGCTGCGAGATTTG-3'

Il6-Fw:
                              (SEQ ID NO: 59)
5'-TCGCTCAGGGTCACAAGAAA-3'

Il6-Rv:
                              (SEQ ID NO: 60)
5'-CATCAGAGGCAAGGAGGAAAAC-3'

Ucp1-Fw:
                              (SEQ ID NO: 61)
5'-GGCCTCTACGACTCAGTCCA-3'
```

-continued

```
Ucpl-Rv:
                            (SEQ ID NO: 62)
5'-TAAGCCGGCTGAGATCTTGT-3'

Cidea-Fw:
                            (SEQ ID NO: 63)
5'-AAACCATGACCGAAGTAGCC-3'

Cidea-Rv:
                            (SEQ ID NO: 64)
5'-AGGCCAGTTGTGATGACTAAGAC-3'

Tnfa-Fw:
                            (SEQ ID NO: 65)
5'-CGGCATGGATCTCAAAGACAAC-3'

Tnfa-Rv:
                            (SEQ ID NO: 66)
5'-AGATAGCAAATCGGCTGACG-3'

F4/80-Fw:
                            (SEQ ID NO: 67)
5'-CTTTGGCTATGGGCTTCCAGTC-3'

F4/80-Rv:
                            (SEQ ID NO: 68)
5'-GCAAGGAGGACAGAGTTTATC-3'

Rplp0-Fw:
                            (SEQ ID NO: 69)
5'-ACTGGTCTAGGACCCGAGAA-3'

Rplp0-Fw:
                            (SEQ ID NO: 70)
5'-TCCCACCTTGTCTCCAGTCT-3'
```

Hormone and Metabolite Assays

Blood glucose levels were measured with a Glucometer Elite™ analyzer (Bayer, Leverkusen, Germany). Brain levels of FGF21 protein were determined by quantitative sandwich enzyme immunoassay Mouse/Rat FGF-21 ELISA kit (MF2100, R&Dsystems, Abingdon, UK), and normalized by total protein content measured with Bradford reagent (Bio-Rad Protein Assay, Bio-Rad, Germany) in whole brain homogenates. To extract lipids from liver, frozen samples of approximately 100 mg were weighted and homogenized in chloroform:methanol (2:1), as described by Carr et al. Hepatic triglycerides and serum triglycerides were quantified spectrophotometrically using an enzymatic assay kit (Horiba-ABX, Montpellier, France). Serum free fatty acids were measured by the acyl-CoA synthase and acyl-CoA oxidaxe methods (Wako Chemicals GmbH, Neuss, Germany). All biochemical parameters were determined using Pentra 400 Analyzer (Horiba-ABX).

Insulin Tolerance Test For insulin tolerance test, insulin (0.75 IU/kg body wt; Humulin Regular; Eli Lilly, Indianapolis, Ind.) was injected intraperitoneally into awake fed mice. Glucose concentration was determined in blood samples obtained from the tail vein at the indicated time points after the insulin injection.

Glucose Tolerance Test

Awake mice were fasted overnight (16 h) and administered with an intraperitoneal injection of glucose (1 g/kg body weight). Glycemia was measured in tail vein blood samples at the indicated time points.

Pyruvate Tolerance Test

Awake mice were fasted overnight (16 h) and administered with an intraperitoneal injection of pyruvate (1 g/kg body weight). Glycemia was measured in tail vein blood samples at the indicated time points.

Example 1. Reversion of Obesity and Diabetes by Intra-CSF Administration of AAV9-CAG-moFGF21-dmirT Vectors in Db/Db Mice We evaluated the anti-diabetogenic and anti-obesogenic therapeutic potential of the AAV-mediated genetic engineering of the brain with FGF21 in 7-week-old db/db male mice, which have defective leptin signalling and are a widely used genetic model of obesity and diabetes. To this end, db/db mice were administered locally intra-cerebrospinal fluid (CSF), through the cisterna magna, with $5\times10^{10}$ vg/mouse of AAV9 vectors encoding a murine codon-optimized FGF21 coding sequence under the control of the CAG ubiquitous promoter which included target sites of the liver-specific miR-122a and the heart-specific miR-1 (AAV9-CAG-moFGF21-dmiRT). As control, non-treated db/db animals were used.

Figure 1:
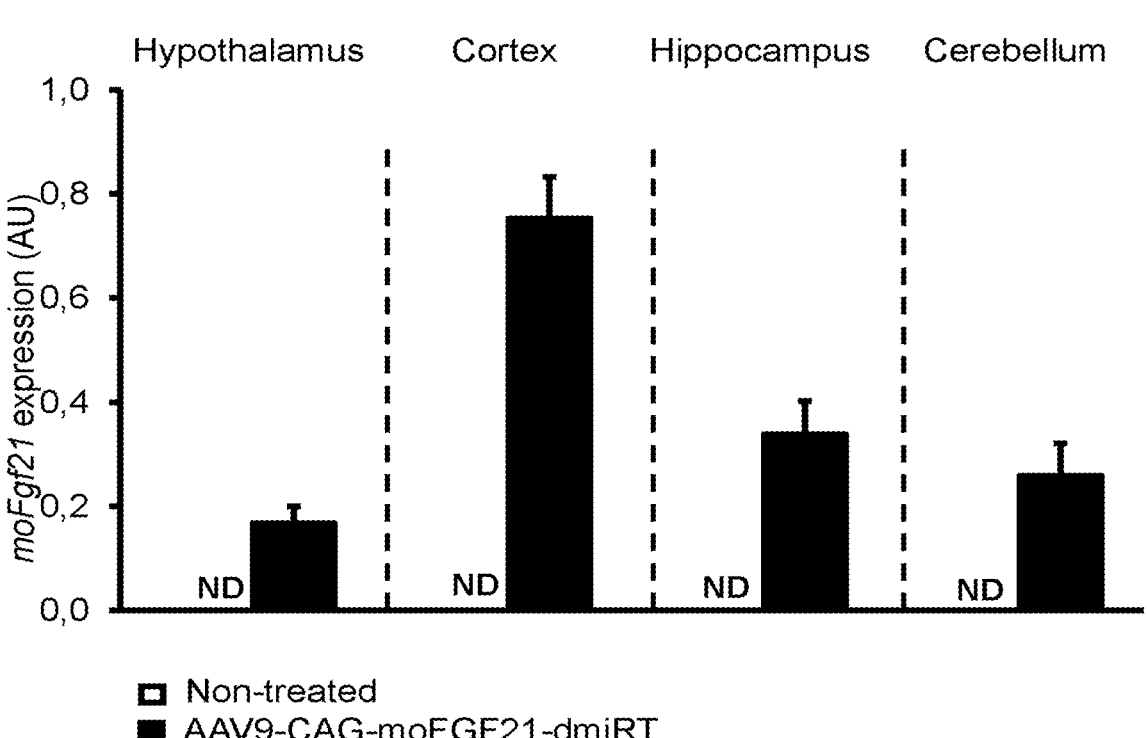
FIG. 1. Expression of moFGF21 in the brain of db/db mice. The expression levels of the murine codon-optimized FGF21 (moFgf21) coding sequence were measured by RTqPCR in Hypothalamus, Cortex, Hippocampus and Cerebellum of db/db mice, and normalized with Rplp0 values. Analyses were performed 12 weeks after intra-CSF administration of $5 \times 10^{10}$ vg/mouse of AAV9-CAG-moFGF21-dmiRT vectors. Results are expressed as the mean±SEM, n=9 animals/group. ND, non-detected.

Intra-CSF administration of AAV9-CAG-moFGF21-dmiRT vectors mediated widespread overexpression of FGF21 in the brain, as evidenced by the increased expression levels of the factor in different areas of the brain such as hypothalamus, cortex, hippocampus and cerebellum, 12 weeks after AAV administration (FIG. 1).

Figures 2A, 2B, 2C:
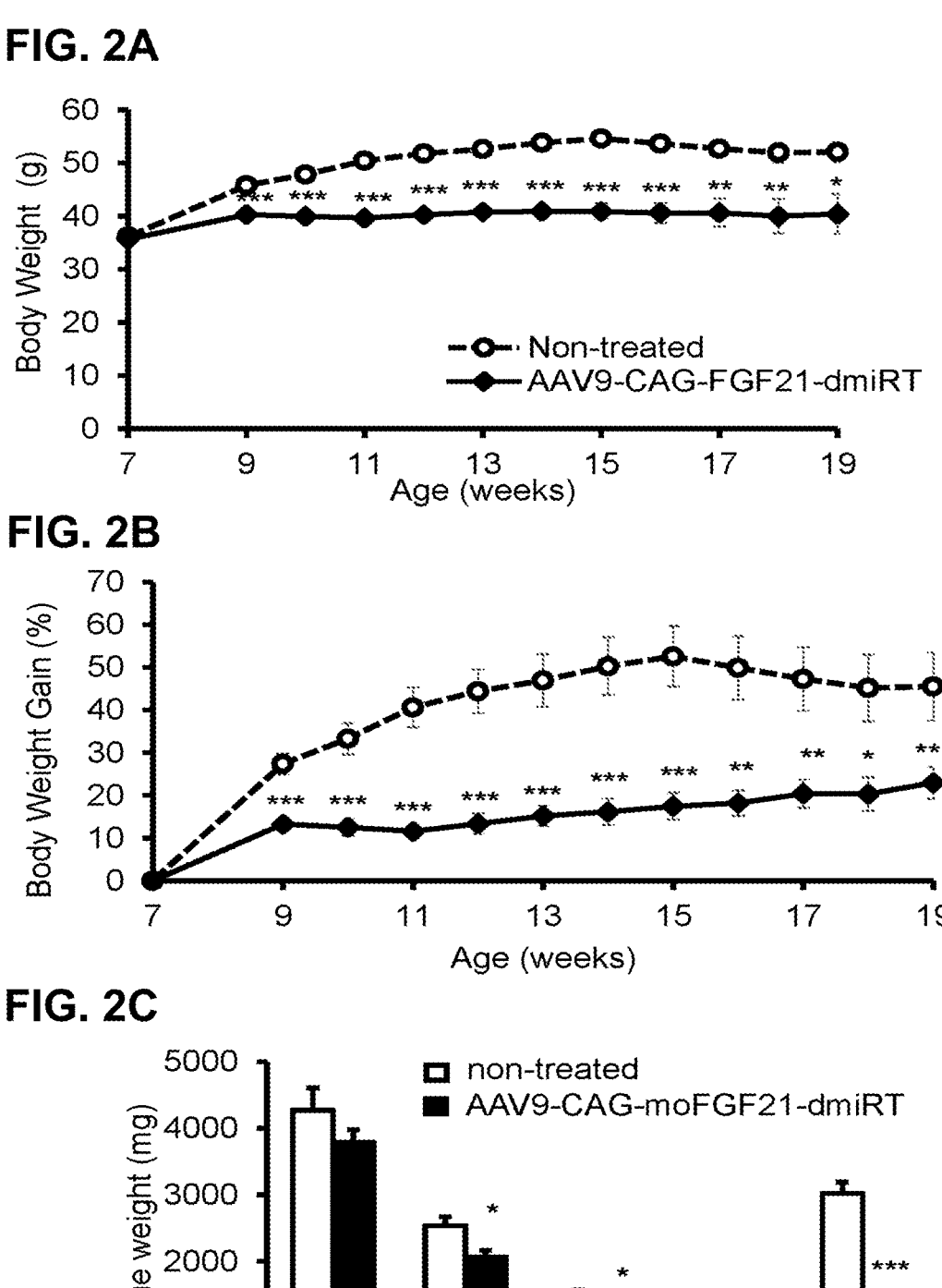
FIG. 2. Decreased body and tissue weight of db/db mice after treatment with AAV9-FGF21 vectors. (A) Body weight evolution. Body weight was measured weekly after the AAV administration. (B) Body weight gain. Body weight gain was calculated as percentage of the increased weight divided by the body weight at the time of AAV administration. (C) Weight of iWAT, eWAT, mWAT, BAT and liver of non-treated and AAV9-FGF21-treated db/db. Analyses were performed 12 weeks after intra-CSF administration of $5 \times 10^{10}$ vg/mouse of AAV9-CAG-moFGF21-dmiRT vectors. Results are expressed as the mean±SEM, n=9 animals/group. * p<0.05,  p<0.01 and * p<0.001 vs non-treated mice. iWAT, inguinal white adipose tissue; eWAT, epididymal white adipose tissue; mWAT, mesenteric white adipose tissue; BAT, interscapular brown adipose tissue; L, liver.
Figure 3:
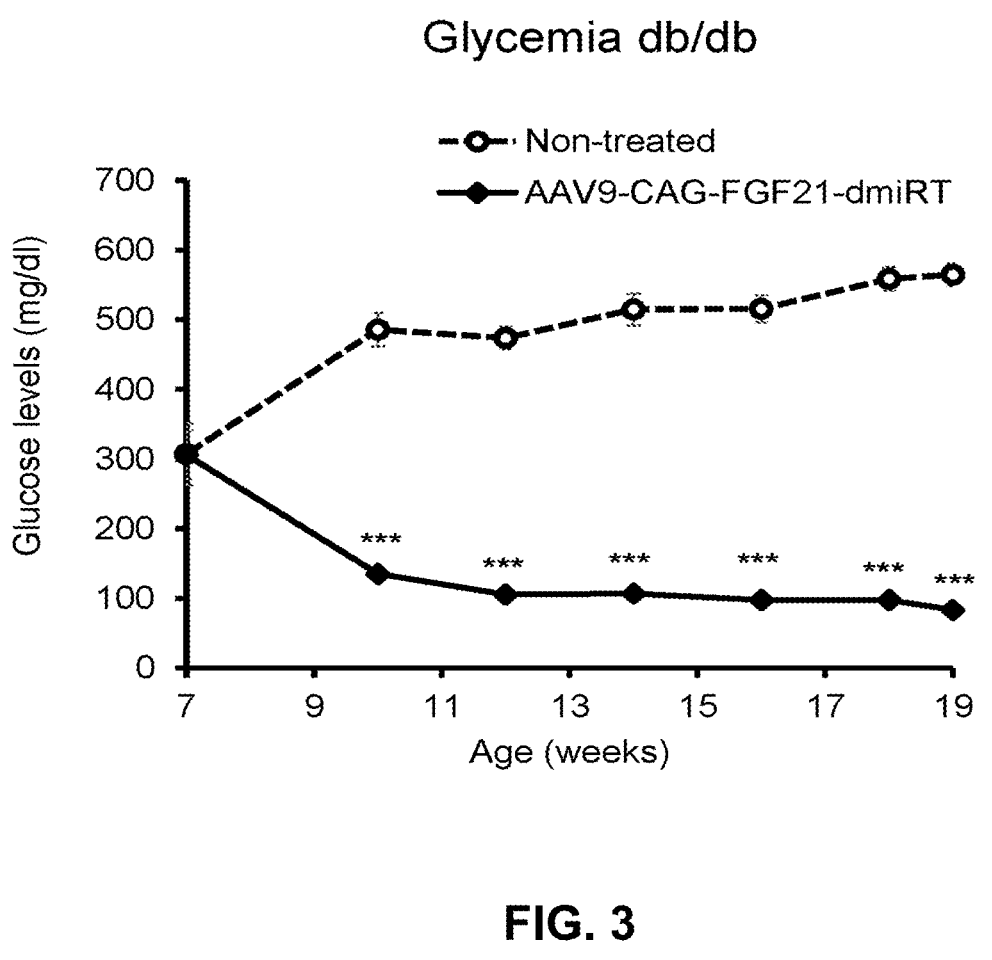

While non-treated db/db mice continued to gain weight during the 12-week follow-up period (~50% weight gain), there was a clear reduction of weight gain in the cohort treated with FGF21-encoding vectors (~20% weight gain) (FIGS. 2A and 2B). In agreement, animals treated with AAV9-CAG-moFGF21-dmiRT vectors showed decreased adiposity and 60% reduction of the weight of the liver (FIG. 2C). Noticeably, db/db mice in which FGF21 gene transfer was targeted to the brain also showed complete normalization of fed glycemia, demonstrating counteraction of diabetes in these animals (FIG. 3).

Figure 4:
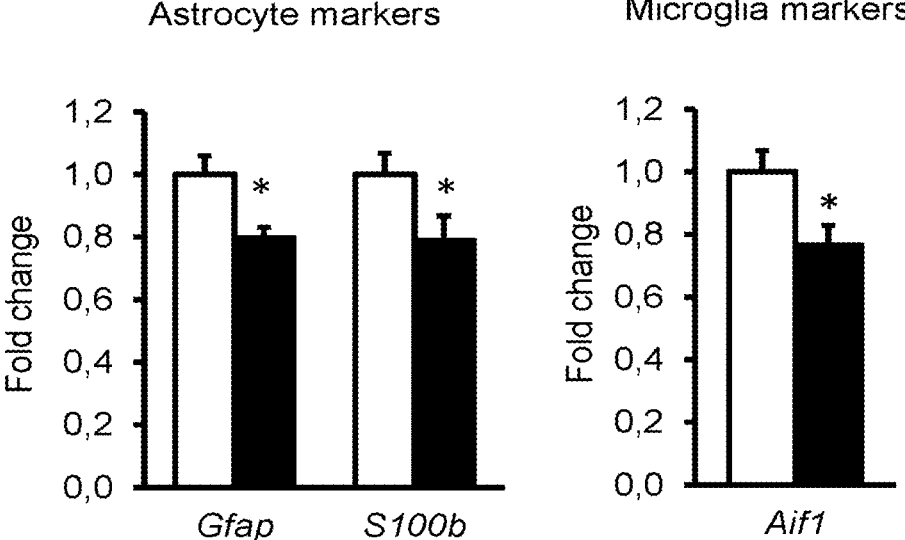
FIG. 4. Reduction of brain inflammation in db/db mice treated with AAV9-FGF21 vectors. Expression levels of astrocyte markers (Gfap and S100b), microglia markers (Aif1) and inflammatory molecules (Nfkb, Il1b and Il6) were measured by RTqPCR in Hypothalamus of db/db mice, and normalized with Rplp0 values. Analyses were performed 12 weeks after intra-CSF administration of $5 \times 10^{10}$ vg/mouse of AAV9-CAG-moFGF21-dmiRT vectors. Results are expressed as the mean±SEM, n=9 animals/group. *p<0.05 vs non-treated mice. Gfap, glial fibrillary acidic protein; S100b, calcium-binding protein B; Aif1, allograft inflammatory factor 1; Nfkb, nuclear factor kappa B; Il1b, interleukin 1 beta; Il6, Interleukin 6.
Figure 4:
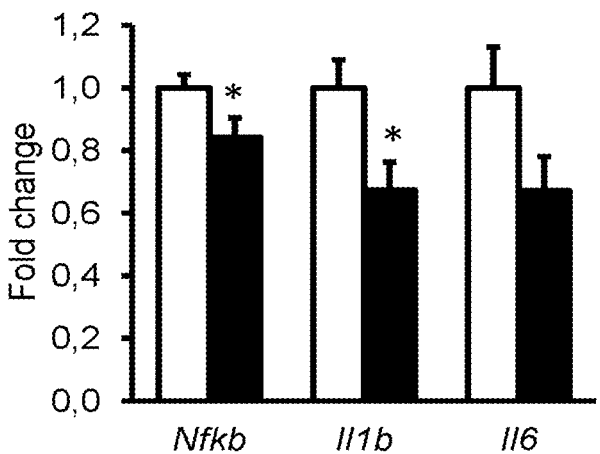

Obesity is associated with brain inflammation (O. Guillemot-Legris, G. G. Muccioli, *Trends Neurosci.* 40, 237-253 (2017). Inflammation in this organ was analyzed through the expression of astrocyte markers Gfap and S100b, the microglia marker Aif1 and pro-inflammatory molecules, such as Nfkb, Il1b and Il6. Db/db mice treated intra-CSF with AAV9-CAG-moFGF21-dmiRT vectors showed decreased expression of Gfap, S100b, Aif1, Nfkb, Il1b and Il6 in the hypothalamus (FIG. 4).

Example 1.1

Figure 10A:
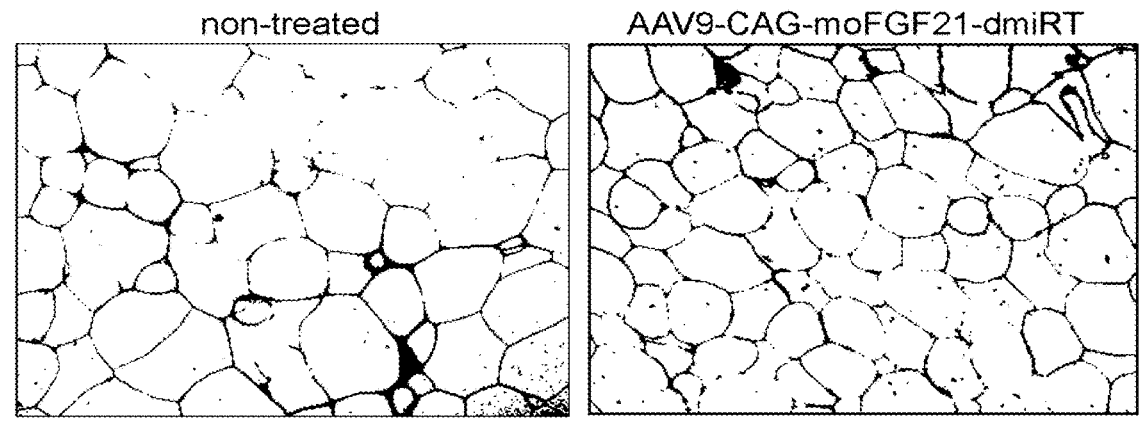
FIG. 10. Reduction of adiposity and increased thermogenesis after treatment with AAV9-FGF21 vectors. Representative images of sections stained with hematoxylin and eosin of (A) eWAT and (B) BAT of AAV9-FGF21-treated and non-treated db/db mice. Original magnification ×200 (C) Expression levels of thermogenic markers (Ucp1 and Cidea) were measured by RTqPCR in BAT of db/db mice, and normalized with Rplp0 values. Analyses were performed 12 weeks after intra-CSF administration of $5 \times 10^{10}$ vg/mouse of AAV9-CAG-moFGF21-dmiRT vectors. Results are expressed as the mean±SEM, n=9 animals/group. ***p<0.001 vs non-treated mice. Ucp1, uncoupling protein 1; Cidea, cell death-inducing DNA fragmentation factor, alpha subunit-like effector A; eWAT, epididymal white adipose tissue; BAT, brown adipose tissue.
Figure 10B:
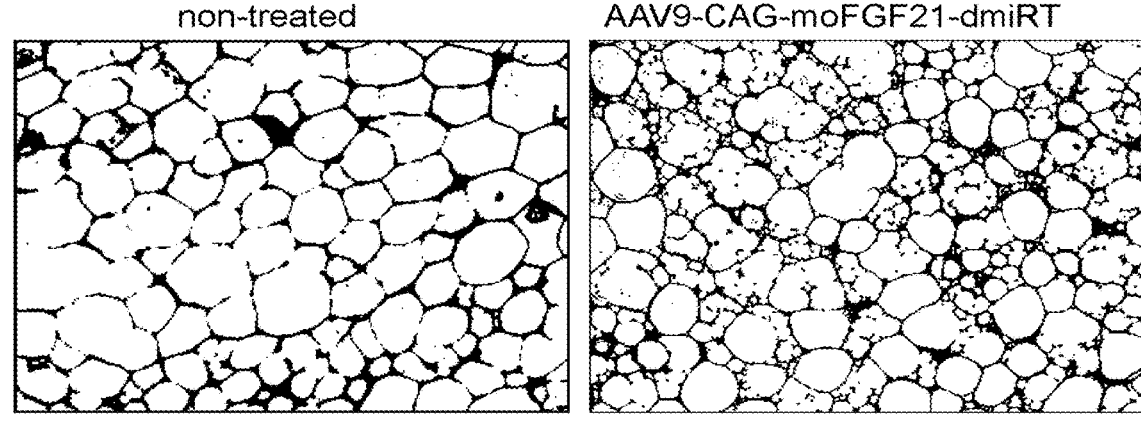
Figure 10C:
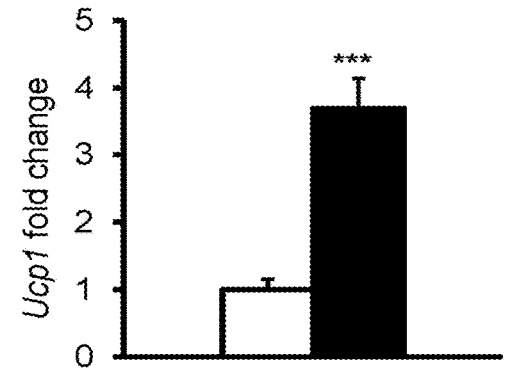
Figure 10C:
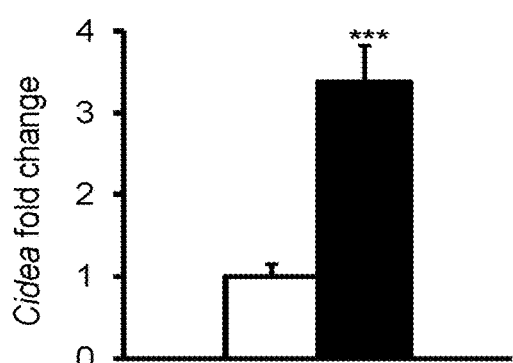
Figures 11A, 11B, 11C:
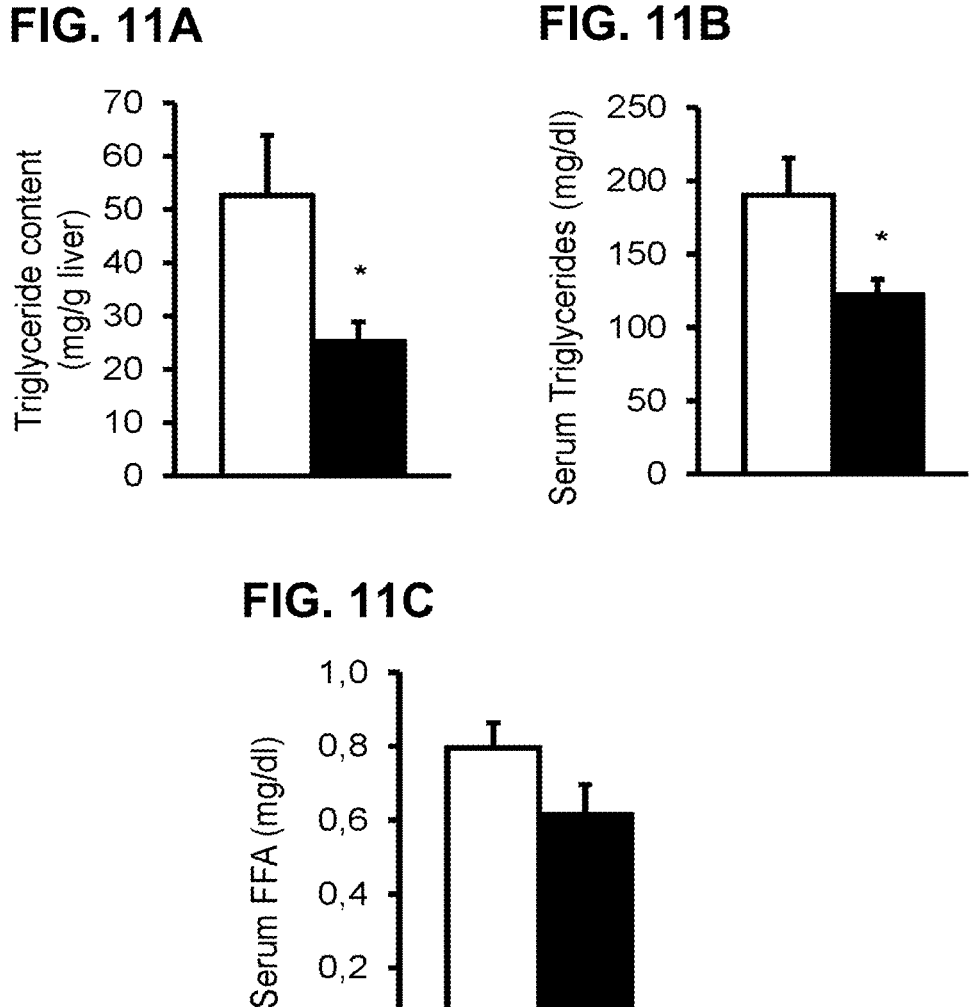
FIG. 11. Decreased hepatic triglyceride content in AAV9-FGF21-treated mice. (A) Hepatic triglyceride content. (B) Serum triglycerides and (C) serum FFA levels, Analyses were performed 12 weeks after intra-CSF administration of the vectors. Results are expressed as the mean±SEM, n=9 animals/group. *p<0.05 vs non-treated mice. FFA, free fatty acids.
Figure 12A:
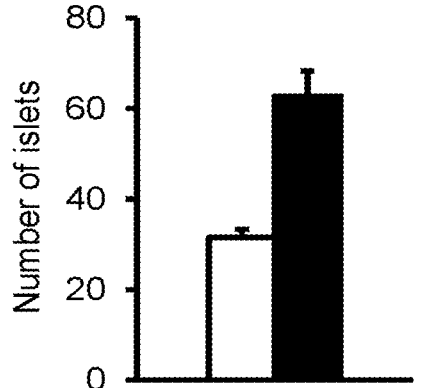
FIG. 12. Amelioration of β-cell mass in FGF21-treated db/db mice. (A) Number of islets and (B) β-cell mass was calculated in non-treated and AAV9-FGF21-treated db/db mice after immunohistochemical analysis of pancreas sections stained with anti-insulin antibody. Results are expressed as the mean±SEM, n=3 animals/group. *p<0.05 vs non-treated mice.
Figure 12B:
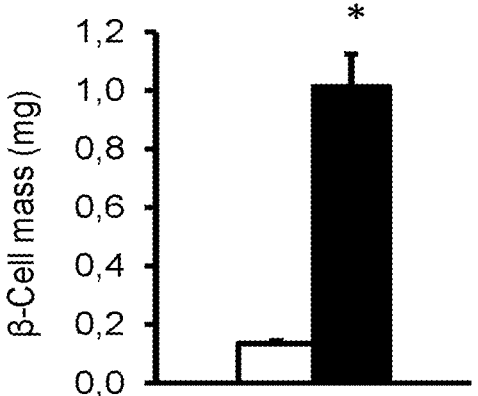

Histological analysis of white adipose tissue by hematoxylin-eosin staining revealed decreased white adipocyte size in eWAT (FIG. 10A). In BAT, the histological analysis showed lower lipid accumulation and more multiloculated brown adipocytes (FIG. 10B). According to these results, the expression levels of Ucp1 and Cidea were highly increased in BAT of FGF21-treated mice (FIG. 10C), suggesting increased thermogenesis after the AAV-FGF21 CNS administration. Hepatic triglyceride content was decreased in AAV9-FGF21-treated db/db mice (FIG. 11A). In parallel circulating levels of triglycerides and serum free fatty acids were also decreased in these mice (FIGS. 11B and 11C). Immunohistochemical analysis of the pancreas revealed increased number of islets (FIG. 12A) and amelioration of β-cell mass (FIG. 12B) in db/db mice after the treatment with AAV9-FGF21 vectors.

Figures 13A, 13B, 13C, 13D:
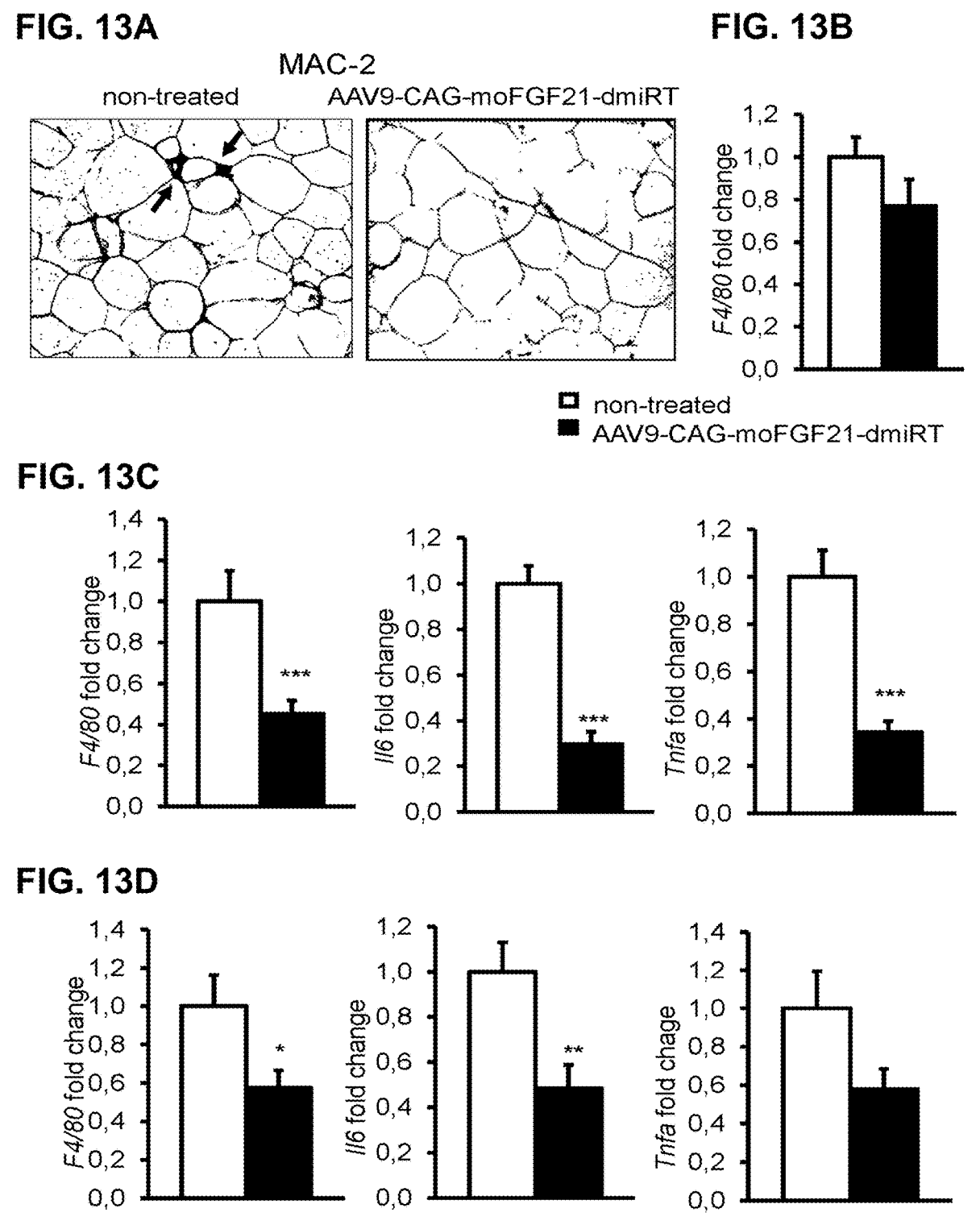

Obesity and diabetes are associated with systemic inflammation. In white adipose tissue, immunohistochemical analysis against the MAC-2 proinflammatory marker indicated decreased macrophages infiltration in AAV9-FGF21- treated mice (FIG. 13A), and this was associated with a decrease in F4/80 mRNA expression levels (FIG. 13B). In brown adipose tissue and in liver, the expression levels of the proinflammatory cytokines F4/80, Il6, and Tnfalpha were also decreased in FGF21-treated animals (FIGS. 13C and 13D, respectively), indicating decreased systemic inflammation after FGF21 gene therapy.

Example 2. Decreased Body Weight Gain by Intra-CSF Administration of AAV9-CAG-moFGF21-dmirT Vectors in SAMP8 Mice Seven-week-old senescence-accelerated mouse-prone 8 (SAMP8) male mice, which is a widely used mouse model of senescence with age-related brain pathologies, were administered locally intra-CSF, through the cisterna magna, with $5 \times 10^{10}$ vg/mouse of AAV9-CAG-moFGF21-dmiRT vectors. As control, non-treated SAMP8 animals were used.

Figure 5:
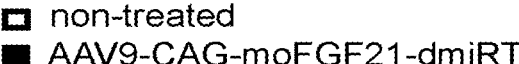
FIG. 5. Expression of moFGF21 in the brain of SAMP8 mice. The expression levels of the murine codon-optimized FGF21 (moFGF21) coding sequence were measured by RTqPCR in Hypothalamus, Cortex, Hippocampus and Cerebellum of SAMP8 mice, and normalized with Rplp0 values. Analyses were performed 14 weeks after intra-CSF administration of $5 \times 10^{10}$ vg/mouse of AAV9-CAG-moFGF21-dmiRT vectors. Results are expressed as the mean±SEM, n=9 animals/group. ND, non-detected.
Figure 5:
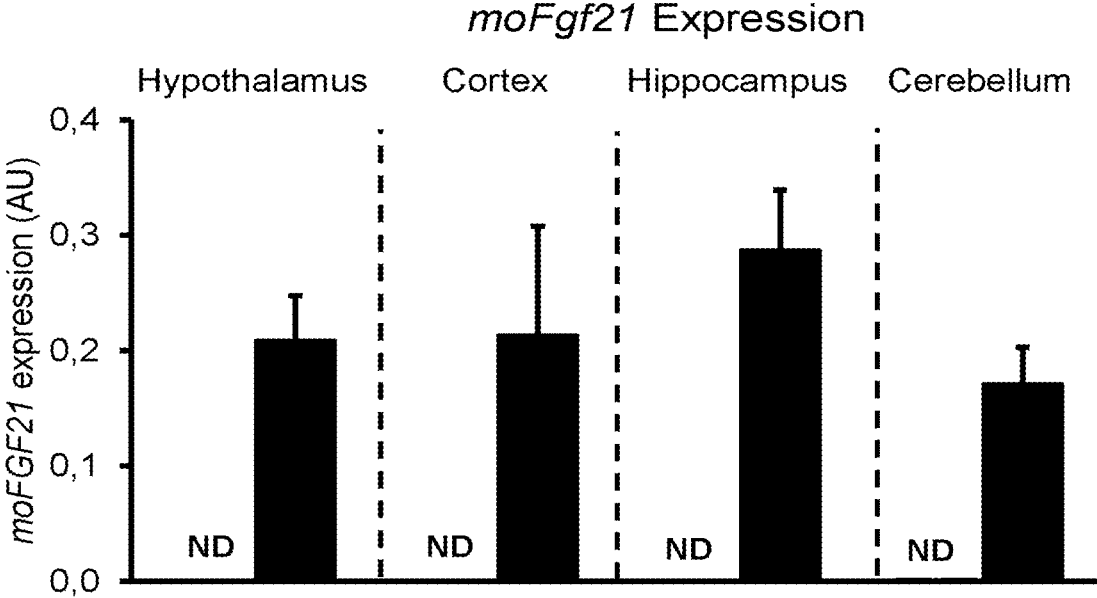
Figures 6A, 6B, 6C:
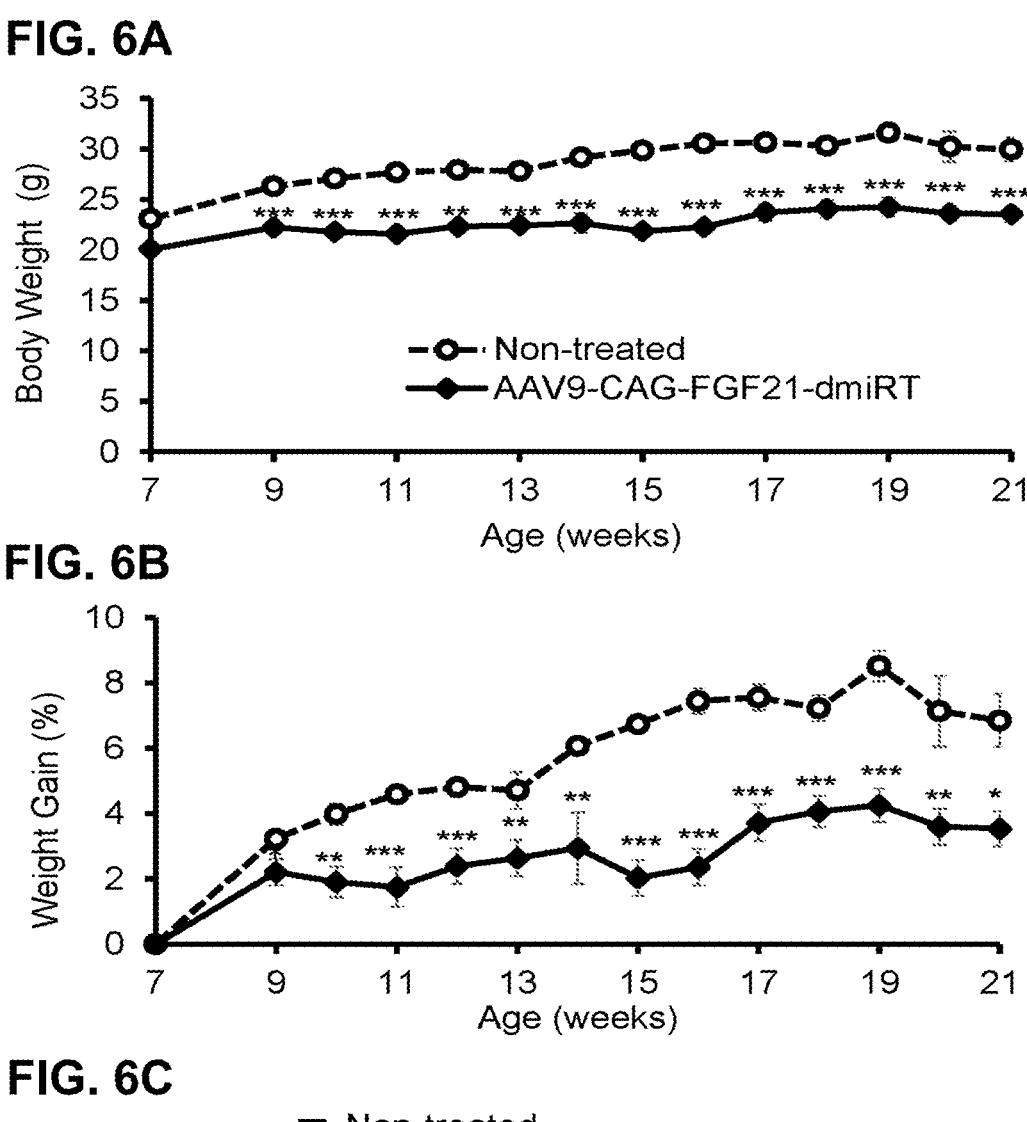
FIG. 6. Decreased body and tissue weight of SAMP8 mice after treatment with AAV9-FGF21 vectors. (A) Body weight evolution. Body weight was measured weekly after the AAV administration. (B) Body weight gain. Body weight gain was calculated as the percentage of increased weight divided by the body weight at the time of AAV administration. (C) Weight of iWAT, eWAT, mWAT, BAT and liver of non-treated and AAV9-FGF21-treated SAMP8. Analyses were performed 14 weeks after intra-CSF administration of $5 \times 10^{10}$ vg/mouse of AAV9-CAG-moFGF21-dmiRT vectors. Results are expressed as the mean±SEM, n=9 animals/group. * p<0.05,  p<0.01 and * p<0.001 vs non-treated mice. iWAT, inguinal white adipose tissue; eWAT, epididymal white adipose tissue; mWAT, mesenteric white adipose tissue; BAT, interscapular brown adipose tissue, L, liver.
Figure 7:
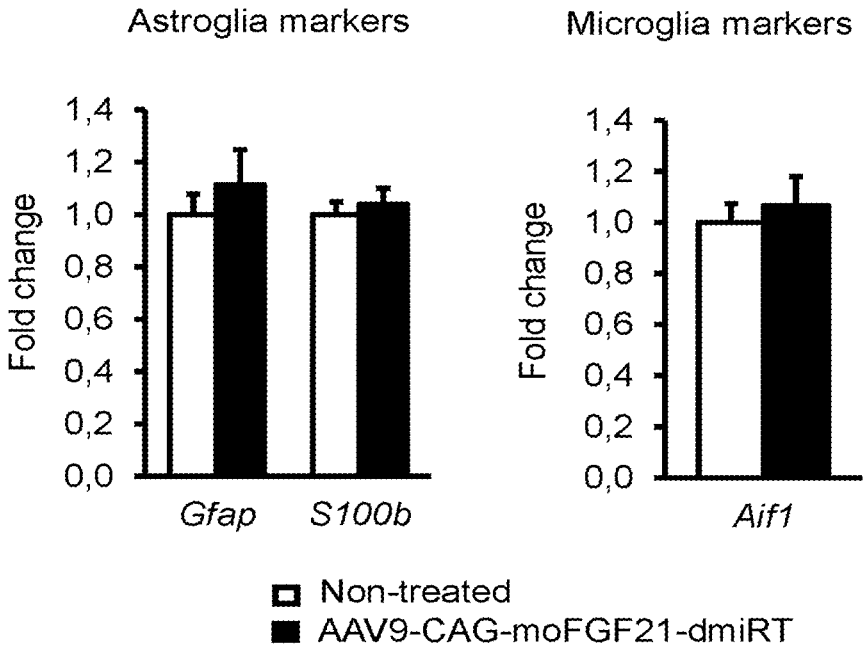
FIG. 7. Reduction of brain inflammation in SAMP8 mice treated with AAV9-FGF21. Expression levels of astrocyte markers (Gfap and S100b), microglia marker (Aif1) and inflammatory molecules (Nfkb, Il1b and Il6) were measured by RTqPCR in Hypothalamus of SAMP8 mice, and normalized with Rplp0 values. Analyses were performed 14 weeks after intra-CSF administration of $5 \times 10^{10}$ vg/mouse of AAV9-CAG-moFGF21-dmiRT vectors. Results are expressed as the mean±SEM, n=9 animals/group. **p<0.01 vs non-treated mice. Gfap, glial fibrillary acidic protein; S100b, calcium-binding protein B; Aif1, allograft inflammatory factor 1; Nfkb, nuclear factor kappa B; Il1b, interleukin 1 beta; Il6, Interleukin 6.
Figure 7:
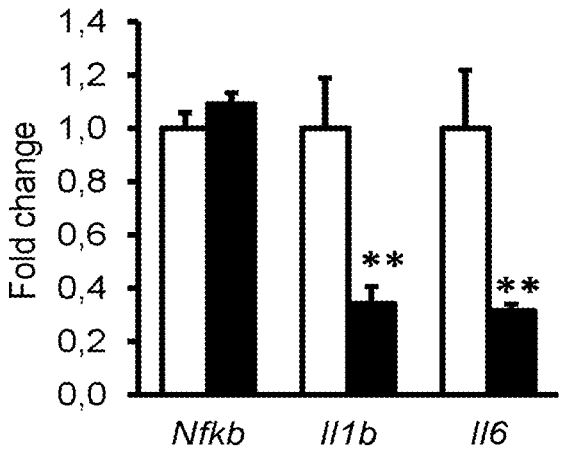

Similar to the observations made in db/db mice, intra-CSF administration of AAV9-CAG-moFGF21-dmiRT vectors mediated robust overexpression of FGF21 in the hypothalamus, cortex, hippocampus and cerebellum of SAMP8 mice (FIG. 5), 14 weeks after AAV administration. FGF21-treated mice showed lower body weight gain than the non-treated cohort (FIGS. 6A and 6B), which was parallel to a decrease in the weight of the liver (FIG. 6C). In addition, expression of the pro-inflammatory cytokines Il1b and Il6 was decreased in the hypothalamus of SAMP8 mice overexpressing FGF21 in the brain (FIG. 7).

Example 3. Brain Transduction after Intra-CSF Administration of AAV1-CAG-moFGF21-dmirT, AAV2-CAG-moFGF21-dmirT and AAV9-CAG-moFGF21-dmirT Vectors To examine whether several AAV serotypes were able to transduce the brain efficiently after direct-CSF administration through the cisterna magna, wild-type mice were treated with $5 \times 10^{10}$ vg/mice of AAV1, AAV2 and AAV9 vectors encoding a murine codon-optimized FGF21 coding sequence under the control of the CAG ubiquitous promoter which included target sites of the liver-specific miR-122a and the heart-specific miR-1 (AAV1-CAG-moFGF21-dmiRT, AAV2-CAG-moFGF21-dmiRT and AAV9-CAG-moFGF21-dmiRT, respectively). As control, non-treated wild-type mice were used.

Figure 8:
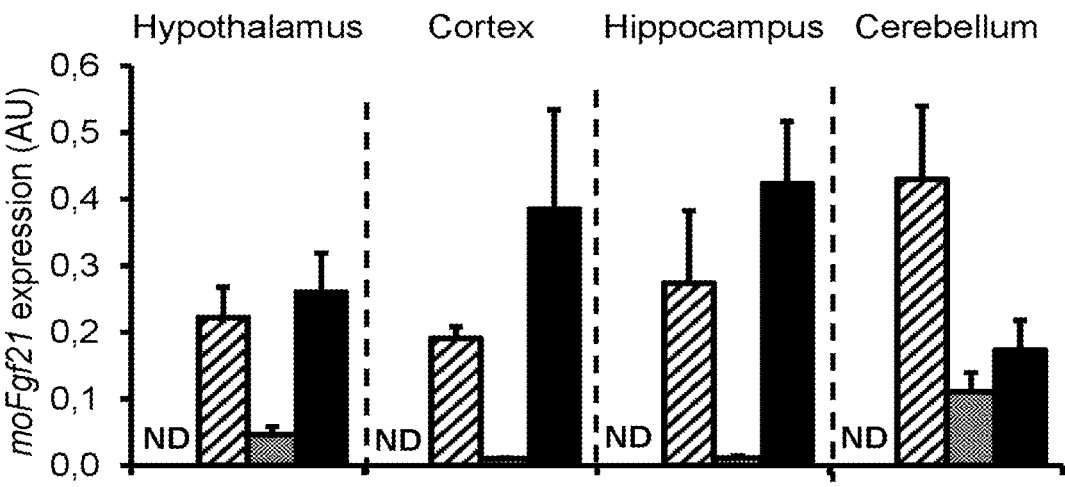
FIG. 8. Expression of moFGF21 in the brain after intra-CSF administration of AAV1-FGF21, AAV2-FGF21 and AAV9-FGF21 vectors. The expression levels of the murine codon-optimized FGF21 (moFGF21) coding sequence were measured by RTqPCR in Hypothalamus, Cortex, Hippocampus and Cerebellum of wild-type mice 3 weeks after intra-CSF administration of $5 \times 10^{10}$ vg/mouse of AAV1-CAG-moFGF21-dmiRT, AAV2-CAG-moFGF21-dmiRT or AAV9-CAG-moFGF21-dmiRT vectors. Results were normalized with Rplp0 values and are expressed as the mean±SEM, n=5 animals/group. ND, non-detected.
Figure 9:
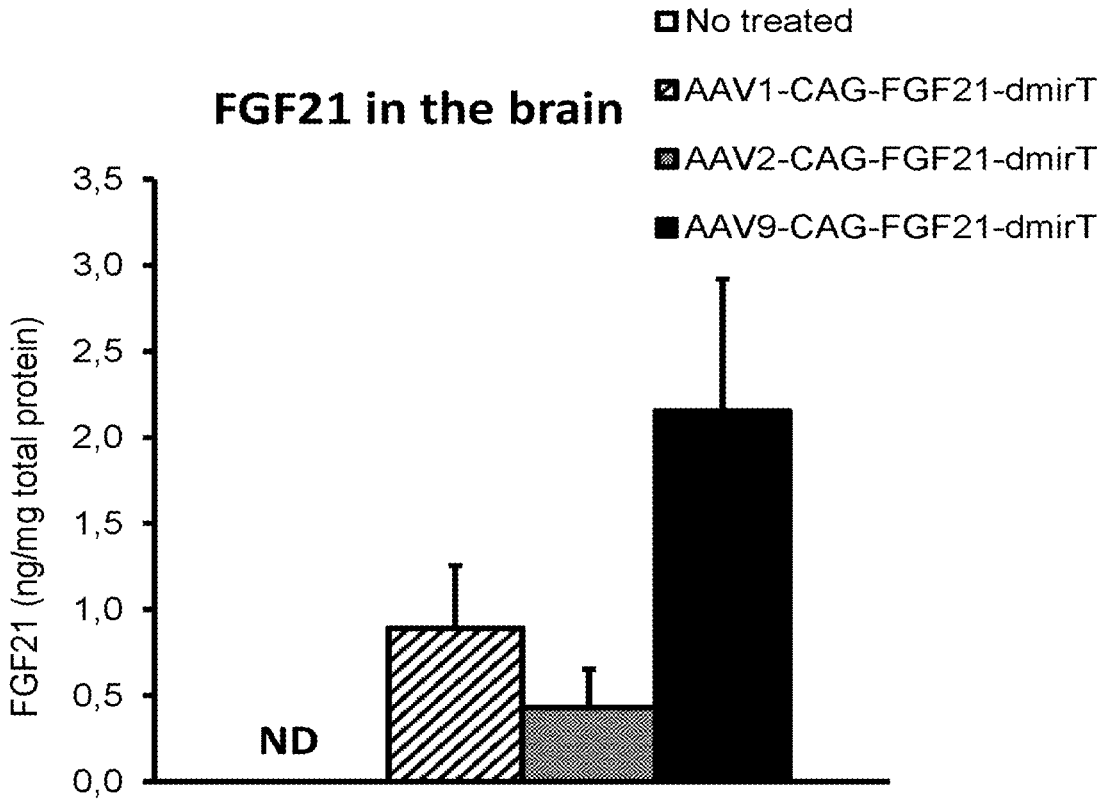
FIG. 9. FGF21 protein levels in the brain. FGF21 protein content was determined by ELISA in brain homogenates of wild-type mice 3 weeks after administration of $5 \times 10^{10}$ vg/mouse of AAV1-CAG-moFGF21-dmiRT, AAV2-CAG-moFGF21-dmiRT or AAV9-CAG-moFGF21-dmiRT vectors. Results were normalized by total protein levels and are expressed as the mean±SEM, n=5 animals/group. ND, non-detected.

Three weeks after intra-CSF administration of the AAV vectors, brain samples were obtained and RT-PCR analysis showed increased moFGF21 expression in different brain areas, such as hypothalamus, cortex, hippocampus and cerebellum (FIG. 8). Moreover, moFGF21 overexpression resulted in increased FGF21 protein content in the whole brain (FIG. 9).

Example 4. Reversion of Obesity and Diabetes by Intra-CSF Administration of AAV1-CAG-moFGF21 Vectors in Db/Db Mice The anti-diabetogenic and anti-obesogenic therapeutic potential of the AAV-mediated genetic engineering of the brain with FGF21 gene therapy, was also evaluated in 7-week-old db/db male mice administered locally intra-cerebrospinal fluid (CSF), through the cisterna magna, with $5 \times 10^{10}$ vg/mouse of AAV1 vectors encoding a murine codon-optimized FGF21 coding sequence under the control of the CAG ubiquitous promoter (AAV1-CAG-moFGF21). As controls, non-treated db/db and non-treated db/+(lean) mice were used.

Figure 14:
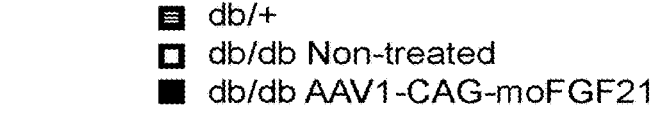
FIG. 14. Expression of FGF21 in the brain of AAV1-FGF21-treated db/db mice. The expression levels of the murine codon-optimized FGF21 (moFgf21) coding sequence were measured by RTqPCR in Hypothalamus, Cortex, Hippocampus, Cerebellum and Olfactory Bulb of db/db mice, and normalized with Rplp0 values. Analyses were performed 16 weeks after intra-CSF administration of 5×10$^{10}$ vg/mouse of AAV1-CAG-moFGF21 vectors. Results are expressed as the mean±SEM, n=7 animals/group. ND, non-detected.
Figure 14:
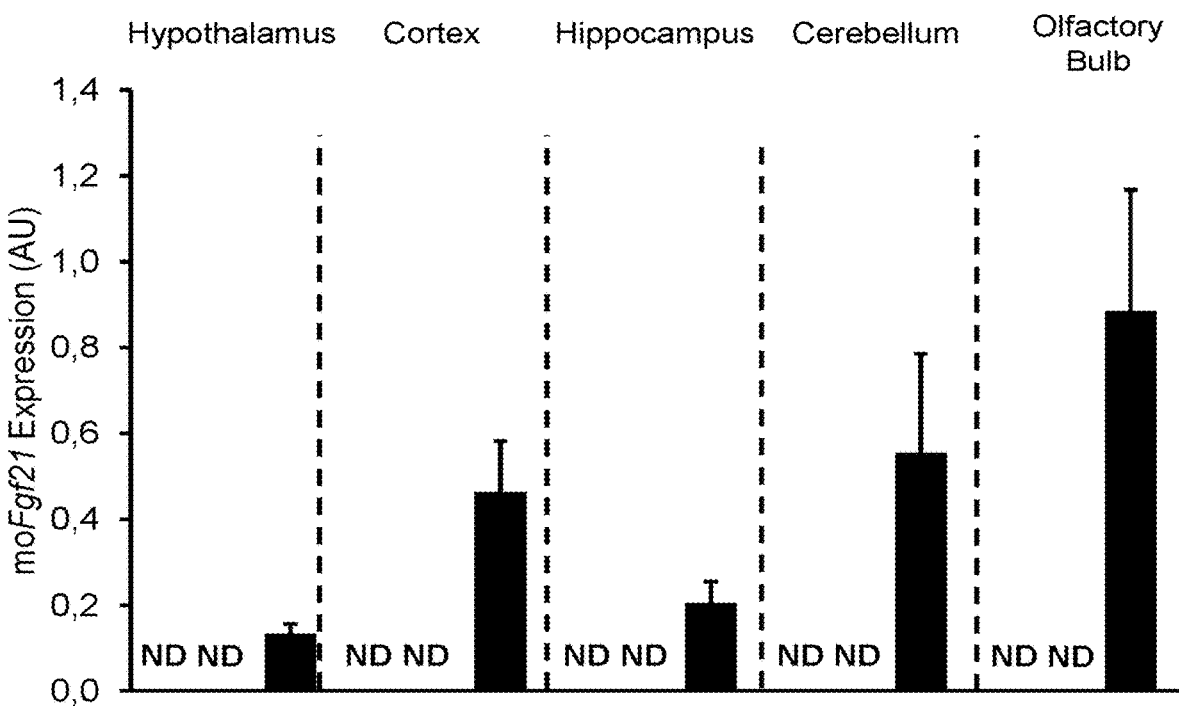

Intra-CSF administration of AAV1-CAG-moFGF21 vectors mediated widespread overexpression of FGF21 in the brain, as evidenced by the increased expression levels of the factor in different areas of the brain such as hypothalamus, cortex, hippocampus, cerebellum and olfactory bulb, 16 weeks after AAV administration (FIG. 14).

Figure 15:
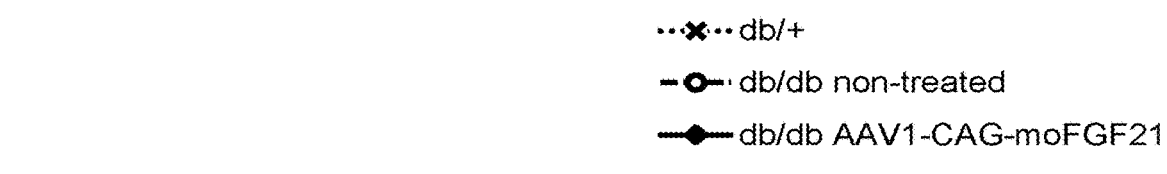
FIG. 15. Decreased body weight of db/db mice after treatment with AAV1-CAG-FGF21 vectors. Body weight was measured weekly after the AAV administration in non-treated db/+(lean), non-treated db/db and AAV1-CAG-FGF21-treated db/db mice. Results are expressed as the mean±SEM, n=7 animals/group. * p<0.05,  p<0.01 and * p<0.001 vs db/+ mice. $$$p<0.001 vs db/db non-treated mice.
Figure 15:
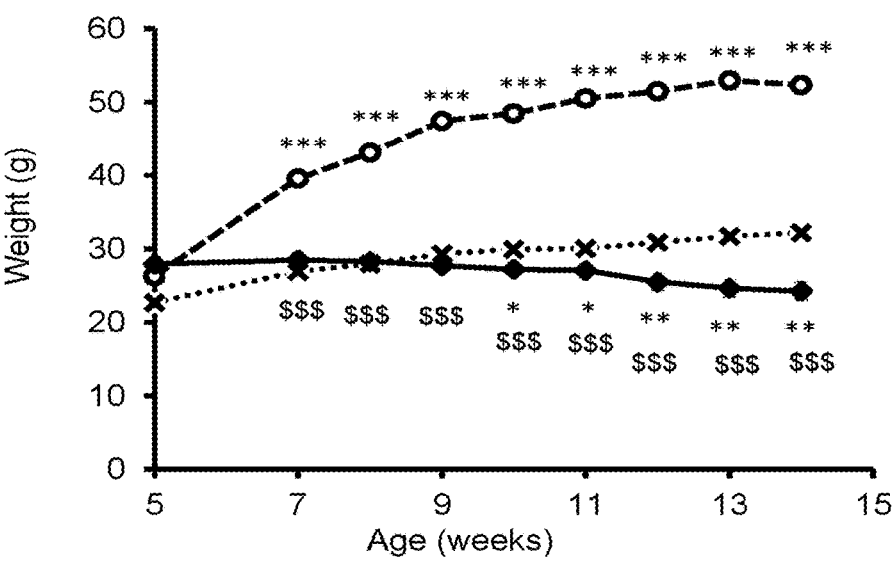
Figure 16A:
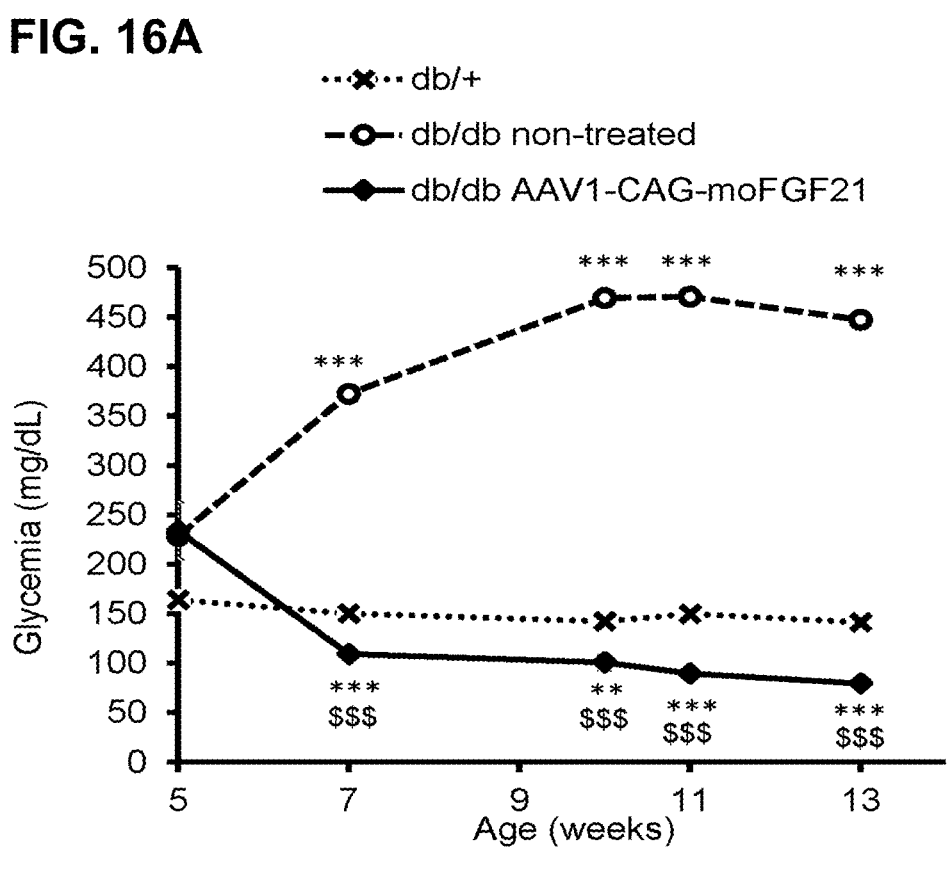
FIG. 16. Reversal of diabetes in AAV1-FGF21-treated db/db. (A) Evolution of fed blood glucose levels of lean (db/+), non-treated and AAV9-CAG-moFGF21-dmiRT-treated db/db mice after intra-CSF vector administration. (B) Fasted blood glucose levels were measured 11 weeks after AAV1-CAG-FGF21 vector administration. Results are expressed as the mean±SEM, n=7 animals/group.  p<0.01 and *p<0.001 vs db/+ mice. $$$p<0.001 vs db/db non-treated mice.
Figure 16B:
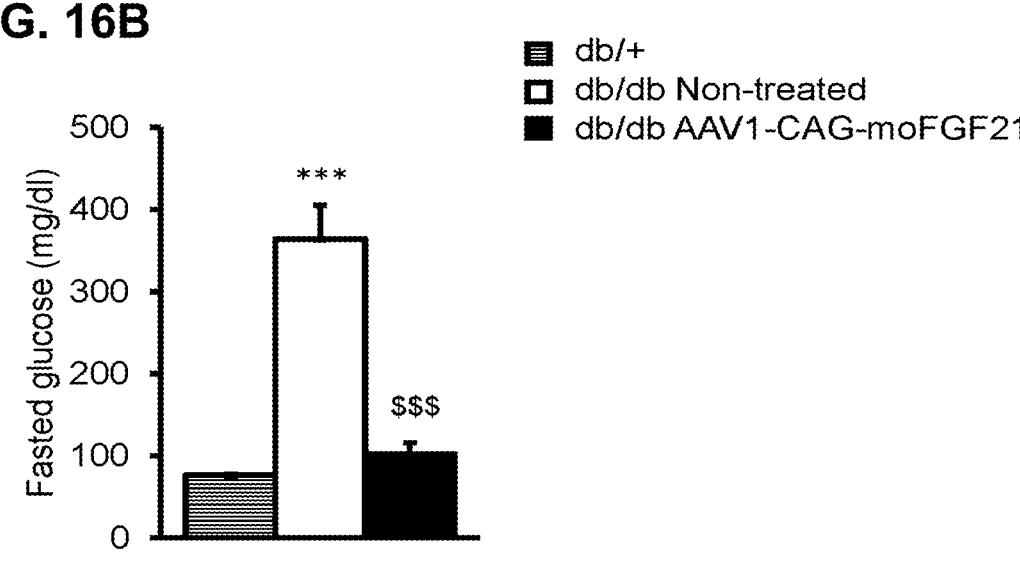

While non-treated db/db mice continued to gain weight during the 14-week follow-up period, the body weight of the cohort treated with AAV1-FGF21-encoding vectors was not increased (FIG. 15). Noticeably, db/db mice in which FGF21 gene transfer was targeted to the brain also showed complete normalization of fed and fasted glycemia (FIGS. 16A and 16B), demonstrating counteraction of diabetes in these animals.

Figure 17:
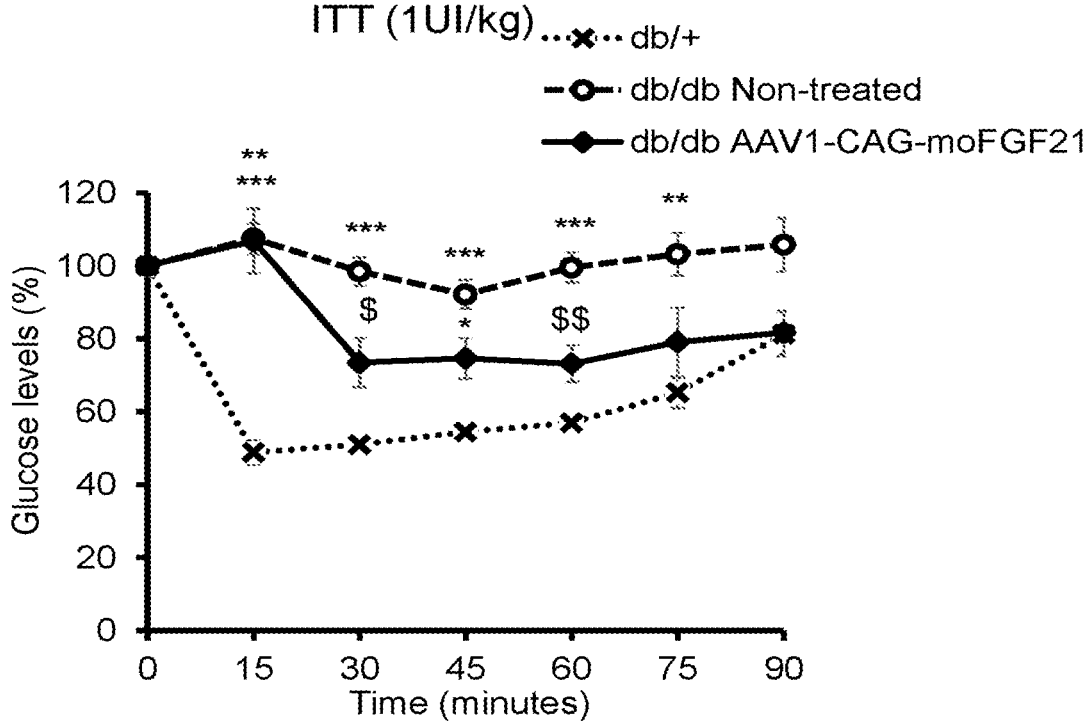
FIG. 17. Increased insulin sensitivity in AAV1-FGF21-treated db/db mice. Intraperitoneal insulin tolerance test. Lean (db/+), non-treated and AAV9-CAG-moFGF21-dmiRT-treated db/db mice were given an intraperitoneal injection of 0.75 U insulin/kg body weight and blood glucose levels were measured at the indicated time points. The test was performed 14 weeks post-AAV administration. Results are expressed as the mean±SEM, n=7 animals/ group. * p<0.05,  p<0.01 and *p<0.001 vs db/+ mice. $p<0.05 and $$p<0.01 vs db/db non-treated mice.

An insulin tolerance test showed that insulin resistance was improved in db/db after the treatment with AAV1-FGF21 viral vectors (FIG. 17) and an intraperitoneal glucose tolerance test on overnight-starved mice showed that db/db mice treated with AAV1-CAG-moFGF21 were more glucose tolerant than db/db non-treated mice (FIG. 18). As an indicator of hepatic gluconeogenesis, an intraperitoneal pyruvate tolerance test was performed. After the pyruvate challenge, blood glucose levels rose to 600 mg/dl in db/db non-treated mice and remained elevated during the test, whereas glucose levels of FGF21 db/db-treated mice and lean mice treated rose to a maximum of 150 mg/dl, thus indicating decreased gluconeogenesis after AAV1-CAG-FGF21 treatment (FIG. 19).

| Sequences | |
|---|---|
| SEQ ID NO: | Description of the sequence |
| 1 | Amino acid sequence of *homo sapiens* FGF21 |
| 2 | Amino acid sequence of *mus musculus* FGF21 |
| 3 | Amino acid sequence of *canis lupus familiaris* FGF21 |
| 4 | Nucleotide sequence of *homo sapiens* FGF21 |
| 5 | Codon optimized nucleotide sequence of *homo sapiens* FGF21-variant 1 |
| 6 | Codon optimized nucleotide sequence of *homo sapiens* FGF21-variant 2 |
| 7 | Codon optimized nucleotide sequence of *homo sapiens* FGF21-variant 3 |

| Sequences |
|---|
| 8 | Nucleotide sequence of *mus musculus* FGF21 |
| 9 | Codon optimized nucleotide sequence of *mus musculus* FGF21 |
| 10 | Nucleotide sequence of *canis lupus familiaris* FGF21 |
| 11 | Codon optimized nucleotide sequence of *canis lupus familiaris* FGF21 |
| 12 | Nucleotide sequence encoding miRT-122a |
| 13 | Nucleotide sequence encoding miRT-1 |
| 14 | Nucleotide sequence encoding miRT-152 |
| 15 | Nucleotide sequence encoding miRT-199a-5p |
| 16 | Nucleotide sequence encoding miRT-199a-3p |
| 17 | Nucleotide sequence encoding miRT-215 |
| 18 | Nucleotide sequence encoding miRT-192 |
| 19 | Nucleotide sequence encoding miRT-148a |
| 20 | Nucleotide sequence encoding miRT-194 |
| 21 | Nucleotide sequence encoding miRT-133a |
| 22 | Nucleotide sequence encoding miRT-206 |
| 23 | Nucleotide sequence encoding miRT-208-5p |
| 24 | Nucleotide sequence encoding miRT-208a-3p |
| 25 | Nucleotide sequence encoding miRT-499-5p |
| 26 | Nucleotide sequence of chimeric intron composed of introns from human β-globin and immunoglobulin heavy chain genes |
| 27 | Nucleotide sequence of CAG promoter |
| 28 | Nucleotide sequence of CMV promoter |
| 29 | Nucleotide sequence of CMV enhancer |
| 30 | Truncated AAV2 5' ITR |
| 31 | Truncated AAV2 3' ITR |
| 32 | SV40 polyadenylation signal |
| 33 | Rabbit β-globin polyadenylation signal |
| 34 | CMV promoter and CMV enhancer sequence |
| 35 | pAAV-CAG-moFGF21-dmiRT |
| 36 | mini-CMV promoter |
| 37 | EF1α promoter |
| 38 | RSV promoter |
| 39 | Synapsin 1 promoter |
| 40 | Calcium/calmodulin-dependent protein kinase II (CaMKII) promoter |
| 41 | Glial fibrillary acidic protein (GFAP) promoter |
| 42 | Nestin promoter |
| 43 | Homeobox Protein 9 (HB9) promoter |
| 44 | Tyrosine hydroxylase (TH) promoter |
| 45 | Myelin basic protein (MBP) promoter |

-continued

| Sequences |
| --- |
| 46      pAAV-CAG-moFGF21 |
| 47-70    RT-qPCR primers |

Amino acid sequence of *homo sapiens* FGF21

(SEQ ID NO: 1)

MDSDETGFEHSGLWVSVLAGLLLGACQAHPIPDSSPLLQFGGQVRQRYLYTDDAQQTEAHLEIREDG

TVGGAADQSPESLLQLKALKPGVIQILGVKTSRFLCQRPDGALYGSLHFDPEACSFRELLLEDGYNVY

QSEAHGLPLHLPGNKSPHRDPAPRGPARFLPLPGLPPALPEPPGILAPQPPDVGSSDPLSMVGPSQG

RSPSYAS

Nucleotide sequence of *homo sapiens* FGF21

(SEQ ID NO: 4)

ATGGACTCGGACGAGACCGGGTTCGAGCACTCAGGACTGTGGGTTTCTGTGCTGGCTGGTCT

TCTGCTGGGAGCCTGCCAGGCACACCCCATCCCTGACTCCAGTCCTCTCCTGCAATTCGGGGGC

CAAGTCCGGCAGCGGTACCTCTACACAGATGATGCCCAGCAGACAGAAGCCCACCTGGAGATCA

GGGAGGATGGGACGGTGGGGGGCGCTGCTGACCAGAGCCCCGAAAGTCTCCTGCAGCTGAAA

GCCTTGAAGCCGGGAGTTATTCAAATCTTGGGAGTCAAGACATCCAGGTTCCTGTGCCAGCGGC

CAGATGGGGCCCTGTATGGATCGCTCCACTTTGACCCTGAGGCCTGCAGCTTCCGGGAGCTGCT

TCTTGAGGACGGATACAATGTTTACCAGTCCGAAGCCCACGGCCTCCCGCTGCACCTGCCAGGG

AACAAGTCCCCACACCGGGACCCTGCACCCCGAGGACCAGCTCGCTTCCTGCCACTACCAGGC

CTGCCCCCCGCACTCCCGGAGCCACCCGGAATCCTGGCCCCCCAGCCCCCCGATGTGGGCTCC

TCGGACCCTCTGAGCATGGTGGGACCTTCCCAGGGCCGAAGCCCCAGCTACGCTTCCTGA

Codon optimized nucleotide sequence of *homo sapiens* FGF21-variant 1

(SEQ ID NO: 5)

ATGGATTCTGATGAGACAGGCTTCGAGCACAGCGGCCTGTGGGTTTCAGTTCTGGCTGGACT

GCTGCTGGGAGCCTGTCAGGCACACCCTATTCCAGATAGCAGCCCTCTGCTGCAGTTCGGCGGA

CAAGTGCGGCAGAGATACCTGTACACCGACGACGCCCAGCAGACAGAAGCCCACCTGGAAATCA

GAGAGGATGGCACAGTTGGCGGAGCCGCCGATCAGTCTCCTGAATCTCTGCTCCAGCTGAAGGC

CCTGAAGCCTGGCGTGATCCAGATCCTGGGCGTGAAAACCAGCCGGTTCCTGTGCCAAAGACCT

GACGGCGCCCTGTATGGCAGCCTGCACTTTGATCCTGAGGCCTGCAGCTTCAGAGAGCTGCTGC

TTGAGGACGGCTACAACGTGTACCAGTCTGAGGCCCATGGCCTGCCTCTGCATCTGCCTGGAAA

CAAGAGCCCTCACAGAGATCCCGCTCCTAGAGGCCCTGCCAGATTTCTGCCTCTTCCTGGATTG

CCTCCTGCTCTGCCAGAGCCTCCTGGAATTCTGGCTCCTCAGCCTCCTGATGTGGGCAGCTCTG

ATCCTCTGAGCATGGTCGGACCTAGCCAGGGCAGATCTCCTAGCTACGCCTCTTGA

Codon optimized nucleotide sequence of *homo sapiens* FGF21-variant 2

(SEQ ID NO: 6)

ATGGACAGCGATGAAACCGGGTTCGAGCACAGCGGTCTGTGGGTGTCCGTGCTGGCCGGAC

TGCTCCTGGGAGCCTGTCAGGCGCACCCCATCCCTGACTCCTCGCCGCTGCTGCAATTCGGCG

GACAAGTCCGCCAGAGATACCTGTACACCGACGACGCCCAGCAGACCGAAGCCCACCTGGAAAT

TCGGGAGGACGGGACTGTGGGAGGCGCTGCAGATCAGTCACCCGAGTCCCTCCTCCAACTGAA

GGCCTTGAAGCCCGGCGTGATTCAGATCCTGGGCGTGAAAACTTCCCGCTTCCTTTGCCAACGG

CCGGATGGAGCTCTGTACGGATCCCTGCACTTCGACCCCGAAGCCTGCTCATTCCGCGAGCTGC

TCCTTGAGGACGGCTATAACGTGTACCAGTCTGAGGCCCATGGACTCCCCCTGCATCTGCCCGG

CAACAAGTCCCCTCACCGGGATCCTGCCCCAAGAGGCCCAGCTCGGTTTCTGCCTCTGCCGGGA

CTGCCTCCAGCGTTGCCCGAACCCCCTGGTATCCTGGCCCCCGCAACCACCTGACGTCGGTTCGT

Sequences

CGGACCCGCTGAGCATGGTCGGTCCGAGCCAGGGAAGGTCCCCGTCCTACGCATCCTGA

Codon optimized nucleotide sequence of *homo sapiens* FGF21-variant 3

(SEQ ID NO: 7)

ATGGATTCCGACGAAACTGGATTTGAACATTCAGGGCTGTGGGTCTCTGTGCTGGCTGGACT

GCTGCTGGGGGCTTGTCAGGCTCACCCCATCCCTGACAGCTCCCCTCTGCTGCAGTTCGGAGGA

CAGGTGCGGCAGAGATACCTGTATACCGACGATGCCCAGCAGACAGAGGCACACCTGGAGATCA

GGGAGGACGGAACCGTGGGAGGAGCAGCCGATCAGTCTCCCGAGAGCCTGCTGCAGCTGAAG

GCCCTGAAGCCTGGCGTGATCCAGATCCTGGGCGTGAAGACATCTCGGTTTCTGTGCCAGCGGC

CCGACGGCGCCCTGTACGGCTCCCTGCACTTCGATCCCGAGGCCTGTTCTTTTAGGGAGCTGCT

GCTGGAGGACGGCTACAACGTGTATCAGAGCGAGGCACACGGCCTGCCACTGCACCTGCCTGG

CAATAAGTCCCCTCACCGCGATCCAGCACCCAGGGGCCCAGCACGCTTCCTGCCTCTGCCAGGC

CTGCCCCCTGCCCTGCCAGAGCCACCCGGCATCCTGGCCCCCCAGCCTCCAGATGTGGGCTCC

AGCGATCCTCTGTCAATGGTGGGGCCAAGTCAGGGGCGGAGTCCTTCATACGCATCATAA

Nucleotide sequence of murine codon-optimized FGF21

(SEQ ID NO: 9)

ATGGAATGGATGAGAAGCAGAGTGGGCACCCTGGGCCTGTGGGTGCGACTGCTGCTGGCTG

TGTTTCTGCTGGGCGTGTACCAGGCCTACCCCATCCCTGACTCTAGCCCCCTGCTGCAGTTTGG

CGGACAAGTGCGGCAGAGATACCTGTACACCGACGACGACCAGGACACCGAGGCCCACCTGGA

AATCCGCGAGGATGGCACAGTCGTGGGCGCTGCTCACAGAAGCCCTGAGAGCCTGCTGGAACT

GAAGGCCCTGAAGCCCGGCGTGATCCAGATCCTGGGCGTGAAGGCCAGCAGATTCCTGTGCCA

GCAGCCTGACGGCGCCCTGTACGGCTCTCCTCACTTCGATCCTGAGGCCTGCAGCTTCAGAGAG

CTGCTGCTGGAGGACGGCTACAACGTGTACCAGTCTGAGGCCCACGGCCTGCCCCCTGAGACTG

CCTCAGAAGGACAGCCCTAACCAGGACGCCACAAGCTGGGGACCTGTGCGGTTCCTGCCTATGC

CTGGACTGCTGCACGAGCCCCAGGATCAGGCTGGCTTTCTGCCTCCTGAGCCTCCAGACGTGG

GCAGCAGCGACCCTCTGAGCATGGTGGAACCTCTGCAGGGCAGAAGCCCCAGCTACGCCTCTT

GA

Nucleotide sequence of CAG promoter (SEQ ID NO: 27)

GACATTGATTATTGACTAGTTATTAATAGTAATCAATTACGGGGTCATTAGTTCATAGCCCATAT

ATGGAGTTCCGCGTTACATAACTTACGGTAAATGGCCCGCCTGGCTGACCGCCCAACGACCCCC

GCCCATTGACGTCAATAATGACGTATGTTCCCATAGTAACGCCAATAGGGACTTTCCATTGACGT

CAATGGGTGGAGTATTTACGGTAAACTGCCCACTTGGCAGTACATCAAGTGTATCATATGCCAAG

TACGCCCCCTATTGACGTCAATGACGGTAAATGGCCCGCCTGGCATTATGCCCAGTACATGACCT

TATGGGACTTTCCTACTTGGCAGTACATCTACGTATTAGTCATCGCTATTACCATGGTCGAGGTGA

GCCCCACGTTCTGCTTCACTCTCCCCATCTCCCCCCCCTCCCCACCCCCAATTTTGTATTTATTTA

TTTTTTAATTATTTTGTGCAGCGATGGGGGCGGGGGGGGGGGGGGGCGCGCGCCAGGCGGG

GCGGGGCGGGGCGAGGGGCGGGGCGGGGCGAGGCGGAGAGGTGCGGCGGCAGCCAATCAG

AGCGGCGCGCTCCGAAAGTTTCCTTTTATGGCGAGGCGGCGGCGGCGGCGGCCCTATAAAAAG

CGAAGCGCGCGGCGGGCGGGAGTCGCTGCGTTGCCTTCGCCCCCGTGCCCCGCTCCGCGCCGC

CTCGCGCCGCCCGCCCCGGCTCTGACTGACCGCGTTACTCCCACAGGTGAGCGGGCGGGACG

GCCCTTCTCCTCCGGGCTGTAATTAGCGCTTGGTTTAATGACGGCTTGTTTCTTTTCTGTGGCTG

Sequences

CGTGAAAGCCTTGAGGGGCTCCGGGAGGGCCCTTTGTGCGGGGGGGAGCGGCTCGGGGGGTGC

GTGCGTGTGTGTGTGCGTGGGGAGCGCCGCGTGCGGCTCCGCGCTGCCCGGCGGCTGTGAGC

GCTGCGGGCGCGGCGCGGGGCTTTGTGCGCTCCGCAGTGTGCGCGAGGGGAGCGCGGCCGG

GGGCGGTGCCCCGCGGTGCGGGGGGCTGCGAGGGGAACAAAGGCTGCGTGCGGGGTGTGTG

CGTGGGGGGGTGAGCAGGGGGTGTGGGCGCGTCGGTCGGGCTGCAACCCCCCCTGCACCCCC

CTCCCCGAGTTGCTGAGCACGGCCCGGCTTCGGGTGCGGGGCTCCGTACGGGCGTGGCGCG

GGGCTCGCCGTGCCGGGCGGGGGGTGGCGGCAGGTGGGGGTGCCGGGCGGGGCGGGGCCG

CCTCGGGCCGGGGAGGGCTCGGGGGAGGGGCGCGGCGGCCCCCGGAGCGCCGGCGGCTGTC

GAGGCGCGGCGAGCCGCAGCCATTGCCTTTTATGGTAATCGTGCGAGAGGGCGCAGGGACTTC

CTTTGTCCCAAATCTGTGCGGAGCCGAAATCTGGGAGGCGCCGCCGCACCCCCTCTAGCGGGC

GCGGGGCGAAGCGGTGCGGCGCCGGCAGGAAGGAAATGGGCGGGGAGGGCCTTCGTGCGTC

GCCGCGCCGCCGTCCCCTTCTCCCTCTCCAGCCTCGGGGCTGTCCGCGGGGGGGACGGCTGCCT

TCGGGGGGGACGGGGCAGGGCGGGGTTCGGCTTCTGGCGTGTGACCGGCGGCTCTAGAGCCT

CTGCTAACCATGTTCATGCCTTCTTCTTTTTCCTACAG

Nucleotide sequence of CMV promoter (SEQ ID NO: 28)
GTGATGCGGTTTTGGCAGTACACCAATGGGCGTGGATAGCGGTTTGACTCACGGGGATTTCC

AAGTCTCCACCCCATTGACGTCAATGGGAGTTTGTTTTGGCACCAAAATCAACGGGACTTTCCAA

AATGTCGTAACAACTGCGATCGCCCGCCCCGTTGACGCAAATGGGCGGTAGGCGTGTACGGTG

GGAGGTCTATATAAGCAGAGCT

Nucleotide sequence of CMV enhancer (SEQ ID NO: 29)
GGCATTGATTATTGACTAGTTATTAATAGTAATCAATTACGGGGTCATTAGTTCATAGCCCATAT

ATGGAGTTCCGCGTTACATAACTTACGGTAAATGGCCCGCCTGGCTGACCGCCCAACGACCCCC

GCCCATTGACGTCAATAATGACGTATGTTCCCATAGTAACGCCAATAGGGACTTTCCATTGACGT

CAATGGGTGGAGTATTTACGGTAAACTGCCCACTTGGCAGTACATCAAGTGTATCATATGCCAAG

TCCGCCCCCTATTGACGTCAATGACGGTAAATGGCCCGCCTGGCATTATGCCCAGTACATGACCT

TACGGGACTTTCCTACTTGGCAGTACATCTACGTATTAGTCATCGCTATTACCATG

CMV promoter and CMV enhancer sequence (SEQ ID NO: 34)
GGCATTGATTATTGACTAGTTATTAATAGTAATCAATTACGGGGTCATTAGTTCATAGCCCATAT

ATGGAGTTCCGCGTTACATAACTTACGGTAAATGGCCCGCCTGGCTGACCGCCCAACGACCCCC

GCCCATTGACGTCAATAATGACGTATGTTCCCATAGTAACGCCAATAGGGACTTTCCATTGACGT

CAATGGGTGGAGTATTTACGGTAAACTGCCCACTTGGCAGTACATCAAGTGTATCATATGCCAAG

TCCGCCCCCTATTGACGTCAATGACGGTAAATGGCCCGCCTGGCATTATGCCCAGTACATGACCT

TACGGGACTTTCCTACTTGGCAGTACATCTACGTATTAGTCATCGCTATTACCATGGTGATGCGGT

TTTGGCAGTACACCAATGGGCGTGGATAGCGGTTTGACTCACGGGGATTTCCAAGTCTCCACCC

CATTGACGTCAATGGGAGTTTGTTTTGGCACCAAAATCAACGGGACTTTCCAAAATGTCGTAACAA

CTGCGATCGCCCGCCCCGTTGACGCAAATGGGCGGTAGGCGTGTACGGTGGGAGGTCTATATA

AGCAGAGCT

AAV2 5' ITR (SEQ ID NO: 30)
GCGCGCTC GCTCGCTCAC TGAGGCCGCC CGGGCAAAGC

-continued

| Sequences |
| --- |

CCGGGCGTCG GGCGACCTTT GGTCGCCCGG CCTCAGTGAG CGAGCGAGCG

CGCAGAGAGG GAGTGGCCAA CTCCATCACT AGGGGTTCCT

AAV2 3' ITR (SEQ ID NO: 31)

AGGAACCCCT AGTGATGGAG TTGGCCACTC CCTCTCTGCG

CGCTCGCTCG CTCACTGAGG CCGGGCGACC AAAGGTCGCC CGACGCCCGG

GCTTTGCCCG GGCGGCCTCA GTGAGCGAGC GAGCGCGC

Rabbit β-globin polyadenylation signal (3' UTR and flanking region of rabbit beta-globin, including polyA signal)

(SEQ ID NO: 33)

GATCTTTTTCCCTCTGCCAAAAATTATGGGGACATCATGAAGCCCCTTGAGCATCTGACTTCTG

GCTAATAAAGGAAATTTATTTTCATTGCAATAGTGTGTTGGAATTTTTTGTGTCTCTCACTCGGAAG

GACATATGGGAGGGCAAATCATTTAAAACATCAGAATGAGTATTTGGTTTAGAGTTTGGCAACATA

TGCCCATATGCTGGCTGCCATGAACAAAGGTTGGCTATAAAGAGGTCATCAGTATATGAAACAGC

CCCCTGCTGTCCATTCCTTATTCCATAGAAAAGCCTTGACTTGAGGTTAGATTTTTTTTATATTTTG

TTTTGTGTTATTTTTTTCTTTAACATCCCTAAAATTTTCCTTACATGTTTTACTAGCCAGATTTTTCCT

CCTCTCCTGACTACTCCCAGTCATAGCTGTCCCTCTTCTCTTATGGAGATC miRT sequences
miRT-122a (SEQ ID NO: 12):
5' CAAACACCATTGTCACACTCCA 3',
target for the microRNA-122a (Accession Number to the miRBase
database MI0000442), which is expressed in the liver.

miRT-152 (SEQ ID NO: 14):
5' CCAAGTTCTGTCATGCACTGA 3',
target for the microRNA-152 (MI0000462), which is expressed in the liver.

miRT-199a-5p (SEQ ID NO: 15):
5' GAACAGGTAGTCTGAACACTGGG 3',
target for the microRNA 199a (MI0000242), which is expressed in the liver.

miRT-199a-3p (SEQ ID NO: 16):
5' TAACCAATGTGCAGACTACTGT 3',
target for the microRNA-199a (MI0000242), which is expressed in the liver.

miRT-215 (SEQ ID NO: 17):
5' GTCTGTCAATTCATAGGTCAT 3',
target for the microRNA-215 (MI0000291), which is expressed in the liver.

miRT-192 (SEQ ID NO: 18):
5' GGCTGTCAATTCATAGGTCAG 3',
target for the microRNA-192 (MI0000234), which is expressed in the liver.

miRT-148a (SEQ ID NO: 19):
5' ACAAAGTTCTGTAGTGCACTGA 3',
target for the microRNA-148a (MI0000253), which is expressed in the liver.

miRT-194 (SEQ ID NO: 20):
5' TCCACATGGAGTTGCTGTTACA 3',
target for the microRNA-194 (MI0000488), which is expressed in the liver.

miRT-133a (SEQ ID NO: 21):
5' CAGCTGGTTGAAGGGGACCAAA 3',
target for the microRNA-133a (MI0000450), which is expressed in the heart.

miRT-206 (SEQ ID NO: 22):
5' CCACACACTTCCTTACATTCCA 3',
target for the microRNA-206 (MI0000490), which is expressed in the heart.

miRT-1 (SEQ ID NO: 13):
5' TTACATACTTCTTTACATTCCA 3',
target for the microRNA-1 (MI0000651), which is expressed in the heart.

Sequences

miRT-208a-5p (SEQ ID NO: 23):
5' GTATAACCCGGGCCAAAAGCTC 3',
target for the microRNA-208a (MI0000251), which is expressed in the heart.

miRT-208a-3p (SEQ ID NO: 24):
5' ACAAGCTTTTTGCTCGTCTTAT 3',
target for the microRNA-208a (MI0000251), which is expressed in the heart.

miRT-499-5p (SEQ ID NO: 25):
5' AAACATCACTGCAAGTCTTAA 3',
target for the microRNA-499 (MI0003183), which is expressed in the heart.

pAAV-CAG-moFGF21-dmiRT (SEQ ID NO: 35)

```
   1     AGTGAGCGAG CGAGCGCGCA GCTGCATTAA TGAATCGGCC AACGCGCGGG

51     GAGAGGCGGT TTGCGTATTG GGCGCTCTTC CGCTTCCTCG CTCACTGACT

101     CGCTGCGCTC GGTCGTTCGG CTGCGGCGAG CGGTATCAGC TCACTCAAAG

151     GCGGTAATAC GGTTATCCAC AGAATCAGGG GATAACGCAG GAAAGAACAT

201     GTGAGCAAAA GGCCAGCAAA AGGCCAGGAA CCGTAAAAAG GCCGCGTTGC

251     TGGCGTTTTT CCATAGGCTC CGCCCCCCTG ACGAGCATCA CAAAAATCGA

301     CGCTCAAGTC AGAGGTGGCG AAACCCGACA GGACTATAAA GATACCAGGC

351     GTTTCCCCCT GGAAGCTCCC TCGTGCGCTC TCCTGTTCCG ACCCTGCCGC

401     TTACCGGATA CCTGTCCGCC TTTCTCCCTT CGGGAAGCGT GGCGCTTTCT

451     CATAGCTCAC GCTGTAGGTA TCTCAGTTCG GTGTAGGTCG TTCGCTCCAA

501     GCTGGGCTGT GTGCACGAAC CCCCCGTTCA GCCCGACCGC TGCGCCTTAT

551     CCGGTAACTA TCGTCTTGAG TCCAACCCGG TAAGACACGA CTTATCGCCA

601     CTGGCAGCAG CCACTGGTAA CAGGATTAGC AGAGCGAGGT ATGTAGGCGG

651     TGCTACAGAG TTCTTGAAGT GGTGGCCTAA CTACGGCTAC ACTAGAAGAA

701     CAGTATTTGG TATCTGCGCT CTGCTGAAGC CAGTTACCTT CGGAAAAAGA

751     GTTGGTAGCT CTTGATCCGG CAAACAAACC ACCGCTGGTA GCGGTGGTTT

801     TTTTGTTTGC AAGCAGCAGA TTACGCGCAG AAAAAAAGGA TCTCAAGAAG

851     ATCCTTTGAT CTTTTCTACG GGGTCTGACG CTCAGTGGAA CGAAAACTCA

901     CGTTAAGGGA TTTTGGTCAT GAGATTATCA AAAAGGATCT TCACCTAGAT

951     CCTTTTAAAT TAAAAATGAA GTTTTAAATC AATCTAAAGT ATATATGAGT

1001     AAACTTGGTC TGACAGTTAC CAATGCTTAA TCAGTGAGGC ACCTATCTCA

1051     GCGATCTGTC TATTTCGTTC ATCCATAGTT GCCTGACTCC CCGTCGTGTA

1101     GATAACTACG ATACGGGAGG GCTTACCATC TGGCCCCAGT GCTGCAATGA

1151     TACCGCGAGA CCCACGCTCA CCGGCTCCAG ATTTATCAGC AATAAACCAG

1201     CCAGCCGGAA GGGCCGAGCG CAGAAGTGGT CCTGCAACTT TATCCGCCTC

1251     CATCCAGTCT ATTAATTGTT GCCGGGAAGC TAGAGTAAGT AGTTCGCCAG

1301     TTAATAGTTT GCGCAACGTT GTTGCCATTG CTACAGGCAT CGTGGTGTCA

1351     CGCTCGTCGT TTGGTATGGC TTCATTCAGC TCCGGTTCCC AACGATCAAG

1401     GCGAGTTACA TGATCCCCCA TGTTGTGCAA AAAAGCGGTT AGCTCCTTCG

1451     GTCCTCCGAT CGTTGTCAGA AGTAAGTTGG CCGCAGTGTT ATCACTCATG

1501     GTTATGGCAG CACTGCATAA TTCTCTTACT GTCATGCCAT CCGTAAGATG
```

-continued

| Sequences |
|---|

```
1551    CTTTTCTGTG ACTGGTGAGT ACTCAACCAA GTCATTCTGA GAATAGTGTA

1601    TGCGGCGACC GAGTTGCTCT TGCCCGGCGT CAATACGGGA TAATACCGCG

1651    CCACATAGCA GAACTTTAAA AGTGCTCATC ATTGGAAAAC GTTCTTCGGG

1701    GCGAAAACTC TCAAGGATCT TACCGCTGTT GAGATCCAGT TCGATGTAAC

1751    CCACTCGTGC ACCCAACTGA TCTTCAGCAT CTTTTACTTT CACCAGCGTT

1801    TCTGGGTGAG CAAAAACAGG AAGGCAAAAT GCCGCAAAAA AGGGAATAAG

1851    GGCGACACGG AAATGTTGAA TACTCATACT CTTCCTTTTT CAATATTATT

1901    GAAGCATTTA TCAGGGTTAT TGTCTCATGA GCGGATACAT ATTTGAATGT

1951    ATTTAGAAAA ATAAACAAAT AGGGGTTCCG CGCACATTTC CCCGAAAAGT

2001    GCCACCTGAC GTCTAAGAAA CCATTATTAT CATGACATTA ACCTATAAAA

2051    ATAGGCGTAT CACGAGGCCC TTTCGTCTCG CGCGTTTCGG TGATGACGGT

2101    GAAAACCTCT GACACATGCA GCTCCCGGAG ACGGTCACAG CTTGTCTGTA

2151    AGCGGATGCC GGGAGCAGAC AAGCCCGTCA GGGCGCGTCA GCGGGTGTTG

2201    GCGGGTGTCG GGGCTGGCTT AACTATGCGG CATCAGAGCA GATTGTACTG

2251    AGAGTGCACC ATATGCGGTG TGAAATACCG CACAGATGCG TAAGGAGAAA

2301    ATACCGCATC AGGCGATTCC AACATCCAAT AAATCATACA GGCAAGGCAA

2351    AGAATTAGCA AAATTAAGCA ATAAAGCCTC AGAGCATAAA GCTAAATCGG

2401    TTGTACCAAA AACATTATGA CCCTGTAATA CTTTTGCGGG AGAAGCCTTT

2451    ATTTCAACGC AAGGATAAAA ATTTTTAGAA CCCTCATATA TTTTAAATGC

2501    AATGCCTGAG TAATGTGTAG GTAAAGATTC AAACGGGTGA GAAAGGCCGG

2551    AGACAGTCAA ATCACCATCA ATATGATATT CAACCGTTCT AGCTGATAAA

2601    TTCATGCCGG AGAGGGTAGC TATTTTTGAG AGGTCTCTAC AAAGGCTATC

2651    AGGTCATTGC CTGAGAGTCT GGAGCAAACA AGAGAATCGA TGAACGGTAA

2701    TCGTAAAACT AGCATGTCAA TCATATGTAC CCCGGTTGAT AATCAGAAAA

2751    GCCCCAAAAA CAGGAAGATT GTATAAGCAA ATATTTAAAT TGTAAGCGTT

2801    AATATTTTGT TAAAATTCGC GTTAAATTTT TGTTAAATCA GCTCATTTTT

2851    TAACCAATAG GCCGAAATCG GCAAAATCCC TTATAAATCA AAAGAATAGA

2901    CCGAGATAGG GTTGAGTGTT GTTCCAGTTT GGAACAAGAG TCCACTATTA

2951    AAGAACGTGG ACTCCAACGT CAAAGGGCGA AAAACCGTCT ATCAGGGCGA

3001    TGGCCCACTA CGTGAACCAT CACCCTAATC AAGTTTTTTG GGGTCGAGGT

3051    GCCGTAAAGC ACTAAATCGG AACCCTAAAG GGAGCCCCCG ATTTAGAGCT

3101    TGACGGGGAA AGCCGGCGAA CGTGGCGAGA AAGGAAGGGA AGAAAGCGAA

3151    AGGAGCGGGC GCTAGGGCGC TGGCAAGTGT AGCGGTCACG CTGCGCGTAA

3201    CCACCACACC CGCCGCGCTT AATGCGCCGC TACAGGGCGC GTACTATGGT

3251    TGCTTTGACG AGCACGTATA ACGTGCTTTC CTCGTTAGAA TCAGAGCGGG

3301    AGCTAAACAG GAGGCCGATT AAAGGGATTT TAGACAGGAA CGGTACGCCA

3351    GAATCCTGAG AAGTGTTTTT ATAATCAGTG AGGCCACCGA GTAAAAGAGT

3401    CTGTCCATCA CGCAAATTAA CCGTTGTCGC AATACTTCTT TGATTAGTAA

3451    TAACATCACT TGCCTGAGTA GAAGAACTCA AACTATCGGC CTTGCTGGTA
```

| Sequences |
| --- |

```
3501    ATATCCAGAA CAATATTACC GCCAGCCATT GCAACGGAAT CGCCATTCGC

3551    CATTCAGGCT GCGCAACTGT TGGGAAGGGC GATCGGTGCG GGCCTCTTCC

3601    ACTGAGGCCC AGCTGCGCGC TCGCTCGCTC ACTGAGGCCG CCCGGGCAAA

3651    GCCCGGGCGT CGGGCGACCT TTGGTCGCCC GGCCTCAGTG AGCGAGCGAG

3701    CGCGCAGAGA GGGAGTGGCC AACTCCATCA CTAGGGGTTC CTTGTAGTTA

3751    ATGATTAACC CGCCATGCTA CTTATCTACT CGACATTGAT TATTGACTAG

3801    TTATTAATAG TAATCAATTA CGGGGTCATT AGTTCATAGC CCATATATGG

3851    AGTTCCGCGT TACATAACTT ACGGTAAATG GCCCGCCTGG CTGACCGCCC

3901    AACGACCCCC GCCCATTGAC GTCAATAATG ACGTATGTTC CCATAGTAAC

3951    GCCAATAGGG ACTTTCCATT GACGTCAATG GGTGGAGTAT TTACGGTAAA

4001    CTGCCCACTT GGCAGTACAT CAAGTGTATC ATATGCCAAG TACGCCCCCT

4051    ATTGACGTCA ATGACGGTAA ATGGCCCGCC TGGCATTATG CCCAGTACAT

4101    GACCTTATGG GACTTTCCTA CTTGGCAGTA CATCTACGTA TTAGTCATCG

4151    CTATTACCAT GGTCGAGGTG AGCCCCACGT TCTGCTTCAC TCTCCCCATC

4201    TCCCCCCCCT CCCCACCCCC AATTTTGTAT TTATTTATTT TTAATTATT

4251    TTGTGCAGCG ATGGGGGCGG GGGGGGGGGG GGGCGCGCG CCAGGCGGGG

4301    CGGGGCGGGG CGAGGGGCGG GGCGGGGCGA GGCGGAGAGG TGCGGCGGCA

4351    GCCAATCAGA GCGGCGCGCT CCGAAAGTTT CCTTTTATGG CGAGGCGGCG

4401    GCGGCGGCGG CCCTATAAAA AGCGAAGCGC GCGGCGGGCG GGAGTCGCTG

4451    CGTTGCCTTC GCCCCGTGCC CCGCTCCGCG CCGCCTCGCG CCGCCCGCCC

4501    CGGCTCTGAC TGACCGCGTT ACTCCCACAG GTGAGCGGGC GGGACGGCCC

4551    TTCTCCTCCG GGCTGTAATT AGCGCTTGGT TTAATGACGG CTTGTTTCTT

4601    TTCTGTGGCT GCGTGAAAGC CTTGAGGGGC TCCGGGAGGG CCCTTTGTGC

4651    GGGGGGAGCG GCTCGGGGGG TGCGTGCGTG TGTGTGTGCG TGGGGAGCGC

4701    CGCGTGCGGC TCCGCGCTGC CCGGCGGCTG TGAGCGCTGC GGGCGCGGCG

4751    CGGGGCTTTG TGCGCTCCGC AGTGTGCGCG AGGGGAGCGC GGCCGGGGGC

4801    GGTGCCCCGC GGTGCGGGGG GCTGCGAGGG GAACAAAGGC TGCGTGCGGG

4851    GTGTGTGCGT GGGGGGGTGA GCAGGGGGTG TGGGCGCGTC GGTCGGGCTG

4901    CAACCCCCCC TGCACCCCCC TCCCCGAGTT GCTGAGCACG GCCCGGCTTC

4951    GGGTGCGGGG CTCCGTACGG GGCGTGGCGC GGGGCTCGCC GTGCCGGGCG

5001    GGGGGTGGCG GCAGGTGGGG GTGCCGGGCG GGGCGGGGCC GCCTCGGGCC

5051    GGGGAGGGCT CGGGGGAGGG GCGCGGCGGC CCCCGGAGCG CCGGCGGCTG

5101    TCGAGGCGCG GCGAGCCGCA GCCATTGCCT TTTATGGTAA TCGTGCGAGA

5151    GGGCGCAGGG ACTTCCTTTG TCCCAAATCT GTGCGGAGCC GAAATCTGGG

5201    AGGCGCCGCC GCACCCCCTC TAGCGGGCGC GGGGCGAAGC GGTGCGGCGC

5251    CGGCAGGAAG GAAATGGGCG GGGAGGGCCT TCGTGCGTCG CCGCGCCGCC

5301    GTCCCCTTCT CCCTCTCCAG CCTCGGGGCT GTCCGCGGGG GGACGGCTGC

5351    CTTCGGGGGG GACGGGGCAG GGCGGGGTTC GGCTTCTGGC GTGTGACCGG
```

-continued

Sequences

| | | | | |
|---|---|---|---|---|
| 5401 | CGGCTCTAGA | GCCTCTGCTA | ACCATGTTCA | TGCCTTCTTC TTTTTCCTAC |
| 5451 | AGCTCCTGGG | CAACGTGCTG | GTTATTGTGC | TGTCTCATCA TTTTGGCAAA |
| 5501 | GAATTGATTA | ATTCGAGCGA | ACGCGTCGAG | TCGCTCGGTA CGATTTAAAT |
| 5551 | TGAATTGGCC | TCGAGCGCAA | GCTTGAGCTA | GCGCCACCAT GGAATGGATG |
| 5601 | AGAAGCAGAG | TGGGCACCCT | GGGCCTGTGG | GTGCGACTGC TGCTGGCTGT |
| 5651 | GTTTCTGCTG | GGCGTGTACC | AGGCCTACCC | CATCCCTGAC TCTAGCCCCC |
| 5701 | TGCTGCAGTT | TGGCGGACAA | GTGCGGCAGA | GATACCTGTA CACCGACGAC |
| 5751 | GACCAGGACA | CCGAGGCCCA | CCTGGAAATC | CGCGAGGATG GCACAGTCGT |
| 5801 | GGGCGCTGCT | CACAGAAGCC | CTGAGAGCCT | GCTGGAACTG AAGGCCCTGA |
| 5851 | AGCCCGGCGT | GATCCAGATC | CTGGGCGTGA | AGGCCAGCAG ATTCCTGTGC |
| 5901 | CAGCAGCCTG | ACGGCGCCCT | GTACGGCTCT | CCTCACTTCG ATCCTGAGGC |
| 5951 | CTGCAGCTTC | AGAGAGCTGC | TGCTGGAGGA | CGGCTACAAC GTGTACCAGT |
| 6001 | CTGAGGCCCA | CGGCCTGCCC | CTGAGACTGC | CTCAGAAGGA CAGCCCTAAC |
| 6051 | CAGGACGCCA | CAAGCTGGGG | ACCTGTGCGG | TTCCTGCCTA TGCCTGGACT |
| 6101 | GCTGCACGAG | CCCCAGGATC | AGGCTGGCTT | TCTGCCTCCT GAGCCTCCAG |
| 6151 | ACGTGGGCAG | CAGCGACCCT | CTGAGCATGG | TGGAACCTCT GCAGGGCAGA |
| 6201 | AGCCCCAGCT | ACGCCTCTTG | AGAATGCGGG | CCCGGTACCC CCGACGCGGC |
| 6251 | CGCTAATTCT | AGATCGCGAA | CAAACACCAT | TGTCACACTC CAGTATACAC |
| 6301 | AAACACCATT | GTCACACTCC | AGATATCACA | AACACCATTG TCACACTCCA |
| 6351 | AGGCGAACAA | ACACCATTGT | CACACTCCAA | GGCTATTCTA GATCGCGAAT |
| 6401 | TACATACTTC | TTTACATTCC | AGTATACATT | ACATACTTCT TTACATTCCA |
| 6451 | GATATCATTA | CATACTTCTT | TACATTCCAA | GGCGAATTAC ATACTTCTTT |
| 6501 | ACATTCCAAG | GCTACCTGAG | GCCCGGGGGT | ACCTCTTAAT TAACTGGCCT |
| 6551 | CATGGGCCTT | CCGCTCACTG | CCCGCTTTCC | AGTCGGGAAA CCTGTCGTGC |
| 6601 | CAGTCAGGTG | CAGGCTGCCT | ATCAGAAGGT | GGTGGCTGGT GTGGCCAATG |
| 6651 | CCCTGGCTCA | CAAATACCAC | TGAGATCTTT | TTCCCTCTGC CAAAAATTAT |
| 6701 | GGGGACATCA | TGAAGCCCCT | TGAGCATCTG | ACTTCTGGCT AATAAAGGAA |
| 6751 | ATTTATTTTC | ATTGCAATAG | TGTGTTGGAA | TTTTTTGTGT CTCTCACTCG |
| 6801 | GAAGGACATA | TGGGAGGGCA | AATCATTTAA | AACATCAGAA TGAGTATTTG |
| 6851 | GTTTAGAGTT | TGGCAACATA | TGCCCATATG | CTGGCTGCCA TGAACAAAGG |
| 6901 | TTGGCTATAA | AGAGGTCATC | AGTATATGAA | ACAGCCCCCT GCTGTCCATT |
| 6951 | CCTTATTCCA | TAGAAAAGCC | TTGACTTGAG | GTTAGATTTT TTTATATTT |
| 7001 | TGTTTTGTGT | TATTTTTTTC | TTTAACATCC | CTAAAATTTT CCTTACATGT |
| 7051 | TTTACTAGCC | AGATTTTTCC | TCCTCTCCTG | ACTACTCCCA GTCATAGCTG |
| 7101 | TCCCTCTTCT | CTTATGGAGA | TCCCTCGACC | TGCAGCCCAA GCTGTAGATA |
| 7151 | AGTAGCATGG | CGGGTTAATC | ATTAACTACA | AGGAACCCCT AGTGATGGAG |
| 7201 | TTGGCCACTC | CCTCTCTGCG | CGCTCGCTCG | CTCACTGAGG CCGGGCGACC |
| 7251 | AAAGGTCGCC | CGACGCCCGG | GCTTTGCCCG | GCGGCCTCA GTGAGCGAGC |
| 7301 | GAGCGCGCAG | CTGGCGTAA | | |

-continued

| Sequences |
| --- |

AAV2 5' ITR: 3615-3742 bp

CAG promoter: 3782-5452 bp

*Mus musculus* codon-optimized FGF21 (moFGF21): 5589-6221 bp dmiRT (4 copies of the miRT-122a and 4 copies of the miRT-1): 6254-6514 bp Rabbit β-globin polyA signal (3' UTR and 3' flanking region of rabbit beta-globin, including polyA signal): 6674-6764 bp AAV2 3' ITR: 7181-7308 bp pAAV-CAG-moFGF21

(SEQ ID NO: 46)

```
   1    AGTGAGCGAG CGAGCGCGCA GCTGCATTAA TGAATCGGCC AACGCGCGGG GAGAGGCGGT

61    TTGCGTATTG GGCGCTCTTC CGCTTCCTCG CTCACTGACT CGCTGCGCTC GGTCGTTCGG

121    CTGCGGCGAG CGGTATCAGC TCACTCAAAG GCGGTAATAC GGTTATCCAC AGAATCAGGG

181    GATAACGCAG GAAAGAACAT GTGAGCAAAA GGCCAGCAAA AGGCCAGGAA CCGTAAAAAG

241    GCCGCGTTGC TGGCGTTTTT CCATAGGCTC CGCCCCCCTG ACGAGCATCA CAAAAATCGA

301    CGCTCAAGTC AGAGGTGGCG AAACCCGACA GGACTATAAA GATACCAGGC GTTTCCCCCT

361    GGAAGCTCCC TCGTGCGCTC TCCTGTTCCG ACCCTGCCGC TTACCGGATA CCTGTCCGCC

421    TTTCTCCCTT CGGGAAGCGT GGCGCTTTCT CATAGCTCAC GCTGTAGGTA TCTCAGTTCG

481    GTGTAGGTCG TTCGCTCCAA GCTGGGCTGT GTGCACGAAC CCCCCGTTCA GCCCGACCGC

541    TGCGCCTTAT CCGGTAACTA TCGTCTTGAG TCCAACCCGG TAAGACACGA CTTATCGCCA

601    CTGGCAGCAG CCACTGGTAA CAGGATTAGC AGAGCGAGGT ATGTAGGCGG TGCTACAGAG

661    TTCTTGAAGT GGTGGCCTAA CTACGGCTAC ACTAGAAGAA CAGTATTTGG TATCTGCGCT

721    CTGCTGAAGC CAGTTACCTT CGGAAAAAGA GTTGGTAGCT CTTGATCCGG CAAACAAACC

781    ACCGCTGGTA GCGGTGGTTT TTTTGTTTGC AAGCAGCAGA TTACGCGCAG AAAAAAAGGA

841    TCTCAAGAAG ATCCTTTGAT CTTTTCTACG GGGTCTGACG CTCAGTGGAA CGAAAACTCA

901    CGTTAAGGGA TTTTGGTCAT GAGATTATCA AAAAGGATCT TCACCTAGAT CCTTTTAAAT

961    TAAAAATGAA GTTTTAAATC AATCTAAAGT ATATATGAGT AAACTTGGTC TGACAGTTAC

1021    CAATGCTTAA TCAGTGAGGC ACCTATCTCA GCGATCTGTC TATTTCGTTC ATCCATAGTT

1081    GCCTGACTCC CCGTCGTGTA GATAACTACG ATACGGGAGG GCTTACCATC TGGCCCCAGT

1141    GCTGCAATGA TACCGCGAGA CCCACGCTCA CCGGCTCCAG ATTTATCAGC AATAAACCAG

1201    CCAGCCGGAA GGGCCGAGCG CAGAAGTGGT CCTGCAACTT TATCCGCCTC CATCCAGTCT

1261    ATTAATTGTT GCCGGGAAGC TAGAGTAAGT AGTTCGCCAG TTAATAGTTT GCGCAACGTT

1321    GTTGCCATTG CTACAGGCAT CGTGGTGTCA CGCTCGTCGT TTGGTATGGC TTCATTCAGC

1381    TCCGGTTCCC AACGATCAAG GCGAGTTACA TGATCCCCCA TGTTGTGCAA AAAAGCGGTT

1441    AGCTCCTTCG GTCCTCCGAT CGTTGTCAGA AGTAAGTTGG CCGCAGTGTT ATCACTCATG

1501    GTTATGGCAG CACTGCATAA TTCTCTTACT GTCATGCCAT CCGTAAGATG CTTTTCTGTG

1561    ACTGGTGAGT ACTCAACCAA GTCATTCTGA GAATAGTGTA TGCGGCGACC GAGTTGCTCT

1621    TGCCCGGCGT CAATACGGGA TAATACCGCG CCACATAGCA GAACTTTAAA AGTGCTCATC

1681    ATTGGAAAAC GTTCTTCGGG GCGAAAACTC TCAAGGATCT TACCGCTGTT GAGATCCAGT

1741    TCGATGTAAC CCACTCGTGC ACCCAACTGA TCTTCAGCAT CTTTTACTTT CACCAGCGTT

1801    TCTGGGTGAG CAAAAACAGG AAGGCAAAAT GCCGCAAAAA AGGGAATAAG GGCGACACGG
```

-continued

| Sequences |
|---|

```
1861   AAATGTTGAA TACTCATACT CTTCCTTTTT CAATATTATT GAAGCATTTA TCAGGGTTAT

1921   TGTCTCATGA GCGGATACAT ATTTGAATGT ATTTAGAAAA ATAAACAAAT AGGGGTTCCG

1981   CGCACATTTC CCCGAAAAGT GCCACCTGAC GTCTAAGAAA CCATTATTAT CATGACATTA

2041   ACCTATAAAA ATAGGCGTAT CACGAGGCCC TTTCGTCTCG CGCGTTTCGG TGATGACGGT

2101   GAAAACCTCT GACACATGCA GCTCCCGGAG ACGGTCACAG CTTGTCTGTA AGCGGATGCC

2161   GGGAGCAGAC AAGCCCGTCA GGGCGCGTCA GCGGGTGTTG GCGGGTGTCG GGGCTGGCTT

2221   AACTATGCGG CATCAGAGCA GATTGTACTG AGAGTGCACC ATATGCGGTG TGAAATACCG

2281   CACAGATGCG TAAGGAGAAA ATACCGCATC AGGCGATTCC AACATCCAAT AAATCATACA

2341   GGCAAGGCAA AGAATTAGCA AAATTAAGCA ATAAAGCCTC AGAGCATAAA GCTAAATCGG

2401   TTGTACCAAA AACATTATGA CCCTGTAATA CTTTTGCGGG AGAAGCCTTT ATTTCAACGC

2461   AAGGATAAAA ATTTTTAGAA CCCTCATATA TTTTAAATGC AATGCCTGAG TAATGTGTAG

2521   GTAAAGATTC AAACGGGTGA GAAAGGCCGG AGACAGTCAA ATCACCATCA ATATGATATT

2581   CAACCGTTCT AGCTGATAAA TTCATGCCGG AGAGGGTAGC TATTTTTGAG AGGTCTCTAC

2641   AAAGGCTATC AGGTCATTGC CTGAGAGTCT GGAGCAAACA AGAGAATCGA TGAACGGTAA

2701   TCGTAAAACT AGCATGTCAA TCATATGTAC CCCGGTTGAT AATCAGAAAA GCCCCAAAAA

2761   CAGGAAGATT GTATAAGCAA ATATTTAAAT TGTAAGCGTT AATATTTTGT TAAAATTCGC

2821   GTTAAATTTT TGTTAAATCA GCTCATTTTT TAACCAATAG GCCGAAATCG GCAAAATCCC

2881   TTATAAATCA AAAGAATAGA CCGAGATAGG GTTGAGTGTT GTTCCAGTTT GGAACAAGAG

2941   TCCACTATTA AAGAACGTGG ACTCCAACGT CAAAGGGCGA AAAACCGTCT ATCAGGGCGA

3001   TGGCCCACTA CGTGAACCAT CACCCTAATC AAGTTTTTTG GGGTCGAGGT GCCGTAAAGC

3061   ACTAAATCGG AACCCTAAAG GGAGCCCCCG ATTTAGAGCT TGACGGGGAA AGCCGGCGAA

3121   CGTGGCGAGA AAGGAAGGGA AGAAAGCGAA AGGAGCGGGC GCTAGGGCGC TGGCAAGTGT

3181   AGCGGTCACG CTGCGCGTAA CCACCACACC CGCCGCGCTT AATGCGCCGC TACAGGGCGC

3241   GTACTATGGT TGCTTTGACG AGCACGTATA ACGTGCTTTC CTCGTTAGAA TCAGAGCGGG

3301   AGCTAAACAG GAGGCCGATT AAAGGGATTT TAGACAGGAA CGGTACGCCA GAATCCTGAG

3361   AAGTGTTTTT ATAATCAGTG AGGCCACCGA GTAAAGAGT CTGTCCATCA CGCAAATTAA

3421   CCGTTGTCGC AATACTTCTT TGATTAGTAA TAACATCACT TGCCTGAGTA GAAGAACTCA

3481   AACTATCGGC CTTGCTGGTA ATATCCAGAA CAATATTACC GCCAGCCATT GCAACGGAAT

3541   CGCCATTCGC CATTCAGGCT GCGCAACTGT TGGGAAGGGC GATCGGTGCG GGCCTCTTCC

3601   ACTGAGGCCC AGCTGCGCGC TCGCTCGCTC ACTGAGGCCG CCCGGGCAAA GCCCGGGCGT

3661   CGGGCGACCT TTGGTCGCCC GGCCTCAGTG AGCGAGCGAG CGCGCAGAGA GGGAGTGGCC

3721   AACTCCATCA CTAGGGGTTC CTTGTAGTTA ATGATTAACC CGCCATGCTA CTTATCTACT

3781   CGACATTGAT TATTGACTAG TTATTAATAG TAATCAATTA CGGGGTCATT AGTTCATAGC

3841   CCATATATGG AGTTCCGCGT TACATAACTT ACGGTAAATG GCCCGCCTGG CTGACCGCCC

3901   AACGACCCCC GCCCATTGAC GTCAATAATG ACGTATGTTC CCATAGTAAC GCCAATAGGG

3961   ACTTTCCATT GACGTCAATG GGTGGAGTAT TTACGGTAAA CTGCCCACTT GGCAGTACAT

4021   CAAGTGTATC ATATGCCAAG TACGCCCCCT ATTGACGTCA ATGACGGTAA ATGGCCCGCC

4081   TGGCATTATG CCCAGTACAT GACCTTATGG GACTTTCCTA CTTGGCAGTA CATCTACGTA
```

-continued

| Sequences |
| --- |

```
4141    TTAGTCATCG CTATTACCAT GGTCGAGGTG AGCCCCACGT TCTGCTTCAC TCTCCCCATC

4201    TCCCCCCCCT CCCCACCCCC AATTTTGTAT TTATTTATTT TTTAATTATT TTGTGCAGCG

4261    ATGGGGGCGG GGGGGGGGGG GGGGCGCGCG CCAGGCGGGG CGGGGCGGGG CGAGGGGCGG

4321    GGCGGGGCGA GGCGGAGAGG TGCGGCGGCA GCCAATCAGA GCGGCGCGCT CCGAAAGTTT

4381    CCTTTTATGG CGAGGCGGCG GCGGCGGCGG CCCTATAAAA AGCGAAGCGC GCGGCGGGCG

4441    GGAGTCGCTG CGTTGCCTTC GCCCCGTGCC CCGCTCCGCG CCGCCTCGCG CCGCCCGCCC

4501    CGGCTCTGAC TGACCGCGTT ACTCCCACAG GTGAGCGGGC GGGACGGCCC TTCTCCTCCG

4561    GGCTGTAATT AGCGCTTGGT TTAATGACGG CTTGTTTCTT TTCTGTGGCT GCGTGAAAGC

4621    CTTGAGGGGC TCCGGGAGGG CCCTTTGTGC GGGGGGAGCG GCTCGGGGGG TGCGTGCGTG

4681    TGTGTGTGCG TGGGGAGCGC CGCGTGCGGC TCCGCGCTGC CCGGCGGCTG TGAGCGCTGC

4741    GGGCGCGGCG CGGGGCTTTG TGCGCTCCGC AGTGTGCGCG AGGGGAGCGC GGCCGGGGGC

4801    GGTGCCCCGC GGTGCGGGGG GCTGCGAGGG GAACAAAGGC TGCGTGCGGG GTGTGTGCGT

4861    GGGGGGGTGA GCAGGGGGTG TGGGCGCGTC GGTCGGGCTG CAACCCCCCC TGCACCCCCC

4921    TCCCCGAGTT GCTGAGCACG GCCCGGCTTC GGGTGCGGGG CTCCGTACGG GGCGTGGCGC

4981    GGGGCTCGCC GTGCCGGGCG GGGGGTGGCG GCAGGTGGGG GTGCCGGGCG GGGCGGGGCC

5041    GCCTCGGGCC GGGGAGGGCT CGGGGGAGGG GCGCGGCGGC CCCCGGAGCG CCGGCGGCTG

5101    TCGAGGCGCG GCGAGCCGCA GCCATTGCCT TTTATGGTAA TCGTGCGAGA GGGCGCAGGG

5161    ACTTCCTTTG TCCCAAATCT GTGCGGAGCC GAAATCTGGG AGGCGCCGCC GCACCCCCTC

5221    TAGCGGGCGC GGGGCGAAGC GGTGCGGCGC CGGCAGGAAG GAAATGGGCG GGGAGGGCCT

5281    TCGTGCGTCG CCGCGCCGCC GTCCCCTTCT CCCTCTCCAG CCTCGGGGCT GTCCGCGGGG

5341    GGACGGCTGC CTTCGGGGGG GACGGGGCAG GGCGGGGTTC GGCTTCTGGC GTGTGACCGG

5401    CGGCTCTAGA GCCTCTGCTA ACCATGTTCA TGCCTTCTTC TTTTTCCTAC AGCTCCTGGG

5461    CAACGTGCTG GTTATTGTGC TGTCTCATCA TTTTGGCAAA GAATTGATTA ATTCGAGCGA

5521    ACGCGTCGAG TCGCTCGGTA CGATTTAAAT TGAATTGGCC TCGAGCGCAA GCTTGAGCTA

5581    GCGCCACCAT GGAATGGATG AGAAGCAGAG TGGGCACCCT GGGCCTGTGG GTGCGACTGC

5641    TGCTGGCTGT GTTTCTGCTG GGCGTGTACC AGGCCTACCC CATCCCTGAC TCTAGCCCCC

5701    TGCTGCAGTT TGGCGGACAA GTGCGGCAGA GATACCTGTA CACCGACGAC GACCAGGACA

5761    CCGAGGCCCA CCTGGAAATC CGCGAGGATG GCACAGTCGT GGGCGCTGCT CACAGAAGCC

5821    CTGAGAGCCT GCTGGAACTG AAGGCCCTGA AGCCCGGCGT GATCCAGATC CTGGGCGTGA

5881    AGGCCAGCAG ATTCCTGTGC CAGCAGCCTG ACGGCGCCCT GTACGGCTCT CCTCACTTCG

5941    ATCCTGAGGC CTGCAGCTTC AGAGAGCTGC TGCTGGAGGA CGGCTACAAC GTGTACCAGT

6001    CTGAGGCCCA CGGCCTGCCC CTGAGACTGC CTCAGAAGGA CAGCCCTAAC CAGGACGCCA

6061    CAAGCTGGGG ACCTGTGCGG TTCCTGCCTA TGCCTGGACT GCTGCACGAG CCCCAGGATC

6121    AGGCTGGCTT TCTGCCTCCT GAGCCTCCAG ACGTGGGCAG CAGCGACCCT CTGAGCATGG

6181    TGGAACCTCT GCAGGGCAGA AGCCCCAGCT ACGCCTCTTG AGAATGCGGG CCCGGTACCC

6241    CCGACGCGGC CTAACTGGCC TCATGGGCCT TCCGCTCACT GCCCGCTTTC CAGTCGGGAA

6301    ACCTGTCGTG CCAGTCAGGT GCAGGCTGCC TATCAGAAGG TGGTGGCTGG TGTGGCCAAT

6361    GCCCTGGCTC ACAAATACCA CTGAGATCTT TTTCCCTCTG CCAAAAATTA TGGGGACATC

6421    ATGAAGCCCC TTGAGCATCT GACTTCTGGC TAATAAAGGA AATTTATTTT CATTGCAATA
```

| Sequences |
| --- |

6481          GTGTGTTGGA ATTTTTTGTG TCTCTCACTC GGAAGGACAT ATGGGAGGGC AAATCATTTA

6541          AAACATCAGA ATGAGTATTT GGTTTAGAGT TTGGCAACAT ATGCCCATAT GCTGGCTGCC

6601          ATGAACAAAG GTTGGCTATA AAGAGGTCAT CAGTATATGA AACAGCCCCC TGCTGTCCAT

6661          TCCTTATTCC ATAGAAAAGC CTTGACTTGA GGTTAGATTT TTTTTATATT TTGTTTTGTG

6721          TTATTTTTTT CTTTAACATC CCTAAAATTT TCCTTACATG TTTTACTAGC CAGATTTTTC

6781          CTCCTCTCCT GACTACTCCC AGTCATAGCT GTCCCTCTTC TCTTATGGAG ATCCCTCGAC

6841          CTGCAGCCCA AGCTGTAGAT AAGTAGCATG GCGGGTTAAT CATTAACTAC AAGGAACCCC

6901          TAGTGATGGA GTTGGCCACT CCCTCTCTGC GCGCTCGCTC GCTCACTGAG GCCGGGCGAC

6961          CAAAGGTCGC CCGACGCCCG GGCTTTGCCC GGGCGGCCTC AGTGAGCGAG CGAGCGCGCA

7021          GCTGGCGTAA

AAV2 5' ITR: 3601-3742 bp

CAG promoter: 3779-5423 bp

*Mus musculus* codon-optimized FGF21 (moFGF21): 5588-6221 bp

Rabbit β-globin polyA signal (3' UTR and 3' flanking region of rabbit beta-globin, including polyA signal): 6315-6833 bp AAV2 3' ITR: 6892-7024 bp Mini-CMV: cmv intermediate early promoter (SEQ ID NO: 36)

TATGCCAAGTACGCCCCCTATTGACGTCAATGACGGTAAATGGCCCGCCTGGCATTATGCCCA

GTACATGACCTTATGGGACTTTCCTACTTGGCAGTACATCTACGTATTAGTCATCGCTATTACCAT

GGTGATGCGGTTTTGGCAGTACATCAATGGGCGTGGATAGCGGTTTGACTCACGGGGATTTCCA

AGTCTCCACCCCATTGACGTCAATGGGAGTTTGTTTTGGCACCAAAATCAACGGGACTTTCCAAA

ATGTCGTAACAACTCCGCCCCATTGACGCAAATGGGCGGTAGGCGTGTACGGTGGGAGGTCTAT

ATAAGCAGAGCTCTCTGGCTAACTAGAGAACCCACTGCTTAACTGGCTTATCGAAATTAATACGAC

TCACTATAGGGAGACCCAAGCTT

Nucleotide sequence of EF1α promoter (SEQ ID NO: 37)

GGCTCCGGTGCCCGTCAGTGGGCAGAGCGCACATCGCCCACAGTCCCCGAGAAGTTGGGGG

GAGGGGTCGGCAATTGAACCGGTGCCTAGAGAAGGTGGCGCGGGGTAAACTGGGAAAGTGATG

TCGTGTACTGGCTCCGCCTTTTTCCCGAGGGTGGGGGAGAACCGTATATAAGTGCAGTAGTCGC

CGTGAACGTTCTTTTTCGCAACGGGTTTGCCGCCAGAACACAGGTAAGTGCCGTGTGTGGTTCC

CGCGGGCCTGGCCTCTTTACGGGTTATGGCCCTTGCGTGCCTTGAATTACTTCCACTGGCTGCA

GTACGTGATTCTTGATCCCGAGCTTCGGGTTGGAAGTGGGTGGGAGAGTTCGAGGCCTTGCGCT

TAAGGAGCCCCTTCGCCTCGTGCTTGAGTTGAGGCCTGGCCTGGGCGCTGGGGCCGCCGCGTG

CGAATCTGGTGGCACCTTCGCGCCTGTCTCGCTGCTTTCGATAAGTCTCTAGCCATTTAAAATTTT

TGATGACCTGCTGCGACGCTTTTTTTCTGGCAAGATAGTCTTGTAAATGCGGGCCAAGATCTGCA

CACTGGTATTTCGGTTTTTGGGGCCGCGGGCGGCGACGGGGCCCGTGCGTCCCAGCGCACATG

TTCGGCGAGGCGGGGCCTGCGAGCGCGGCCACCGAGAATCGGACGGGGGTAGTCTCAAGCTG

GCCGGCCTGCTCTGGTGCCTGGCCTCGCGCCGCCGTGTATCGCCCCGCCCTGGGCGGCAAGG

CTGGCCCGGTCGGCACCAGTTGCGTGAGCGGAAAGATGGCCGCTTCCCGGCCCTGCTGCAGGG

AGCTCAAAATGGAGGACGCGGCGCTCGGGAGAGCGGGCGGGTGAGTCACCCACACAAAGGAAA

-continued

Sequences

AGGGCCTTTCCGTCCTCAGCCGTCGCTTCATGTGACTCCACGGAGTACCGGGCGCCGTCCAGG

CACCTCGATTAGTTCTCGAGCTTTTGGAGTACGTCGTCTTTAGGTTGGGGGGAGGGGTTTTATGC

GATGGAGTTTCCCCACACTGAGTGGGTGGAGACTGAAGTTAGGCCAGCTTGGCACTTGATGTAA

TTCTCCTTGGAATTTGCCCTTTTTGAGTTTGGATCTTGGTTCATTCTCAAGCCTCAGACAGTGGTT

CAAAGTTTTTTTCTTCCATTTCAGGTGTCGTGA

Nucleotide sequence of RSV promoter (SEQ ID NO: 38)

CATGTTTGACAGCTTATCATCGCAGATCCGTATGGTGCACTCTCAGTACAATCTGCTCTGATG

CCGCATAGTTAAGCCAGTATCTGCTCCCTGCTTGTGTGTTGGAGGTCGCTGAGTAGTGCGCGAG

CAAAATTTAAGCTACAACAAGGCAAGGCTTGACCGACAATTGCATGAAGAATCTGCTTAGGGTTA

GGCGTTTTGCGCTGCTTCGCGATGTACGGGCCAGATATTCGCGTATCTGAGGGGACTAGGGTGT

GTTTAGGCGAAAAGCGGGGCTTCGGTTGTACGCGGTTAGGAGTCCCCTCAGGATATAGTAGTTT

CGCTTTTGCATAGGGAGGGGGAAATGTAGTCTTATGCAATACTCTTGTAGTCTTGCAACATGGTA

ACGATGAGTTAGCAACATGCCTTACAAGGAGAGAAAAAGCACCGTGCATGCCGATTGGTGGAAG

TAAGGTGGTACGATCGTGCCTTATTAGGAAGGCAACAGACGGGTCTGACATGGATTGGACGAAC

CACTAAATTCCGCATTGCAGAGATATTGTATTTAAGTGCCTAGCTCGATACAATAAACGCCATTTG

ACCATTCACCACATTGGTGTGCACCTCCAAGCTGGGTACCAGCT

Synapsin 1 promoter (SEQ ID NO: 39)

ctgcgctctcaggcacgacacgactcctccgctgcccaccgcagactgaggcagcgctgagtcgccggcgccgcagcgcagatggtcg cgcccgtgccccctatctcgcgcctcgcgtggtgcggtccggctgggccggcggcggcgcggacgcgaccaaggtggccgggaagggg agtttgcgggggaccggcgagtgacgtcagcgcgccttcagtgctgaggcggcggtggcgcgcgccgccaggcgggggcgaaggcactgt ccgcggtgctgaagctggcagtgcgcacgcgcctcgccgcatcctgtttcccctcccctctctgataggggatgcgcaatttggggaatgggg gttgggtgcttgtccagtgggtcggggtcggtcgtcaggtaggcaccccacccccgcctcatcctggtcctaaaacccacttgcact Calcium/calmodulin-dependent protein kinase II (CaMKII) promoter (SEQ ID NO: 40)

taacattatggccttaggtcacttcatctccatggggttcttcttctgattttctagaaaatgagatggggggtgcagagagcttcctcagtgacctg cccagggtcacatcagaaatgtcagagctagaacttgaactcagattactaatcttaaattccatgccttgggggcatgcaagtacgatatacag aaggagtgaactcattagggcagatgaccaatgagtttaggaaagaagagtccagggcagggtacatctacaccacccgcccagccctgg gtgagtccagccacgttcacctcattatagttgcctctctccagtcctaccttgacgggaagcacaagcagaaactgggacaggagccccagg agaccaaatcttcatggtccctctgggaggatgggtggggagagctgtggcagaggcctcaggaggggccctgctgctcagtggtgacagat aggggtgagaaagcagacagagtcattccgtcagcattctgggtctgtttggtacttcttctcacgctaaggtggcggtgtgatatgcacaatggc taaaaagcagggagagctggaaagaaacaaggacagagacagaggccaagtcaaccagaccaattcccagaggaagcaaagaaac cattacagagactacaaggggggaagggaaggagagatgaattagcttcccctgtaaaccttagaacccagctgttgccagggcaacggggc aatacctgtctcttcagaggagatgaagttgccagggtaactacatcctgtctttctcaaggaccatcccagaatgtggcacccactagccgttac catagcaactgcctctttgccccacttaatcccatccgtctgttaaaaagggccctatagttggaggtggggaggtaggaagagagcgatgatca cttgtggactaagtttgttcgcatcccccttctccaacccctcagtacatcaccctgggggaacagggtccacttgctcctgggcccacacagtcct gcagtattgtgtatataaggccagggcaaagaggagcaggtttttaaagtgaaaggcaggcaggtgttggggaggcagttaccggggcaacg ggaacagggcgtttcggaggtggttgccatggggacctggatgctgacgaaggctcgcgaggctgtgagcagccacagtgccctgctcaga agccccaagctcgtcagtcaagccggttctccgtttgcactcaggagcacgggcaggcgagtggcccctagttctgggggcagcgggg -continued Sequences Glial fibrillary acidic protein (GFAP) promoter (SEQ ID NO: 41)

cgcgtgatctaacatatcctggtgtggagtaggggacgctgctctgacagaggctcgggggcctgagctggctctgtgagctggggagga ggcagacagccaggccttgtctgcaagcagacctggcagcattgggctggccgcccccagggcctcctcttcatgcccagtgaatgactca ccttggcacagacacaatgttcggggtgggcacagtgcctgcttcccgccgcaccccagcccccctcaaatgccttccgagaagcccattgag caggggcttgcattgcaccccagcctgacagcctggcatcttgggataaaagcagcacagcccctaggggctgcccttgctgtgtggcgcc accggcggtggagaacaaggctctattcagcctgtgcccaggaaaggggatcaggggatgcccaggcatggacagtgggtggcaggggg ggagaggagggctgtctgcttcccagaagtccaaggacacaaatgggtgaggggagagctctccccatagctgggctgcggcccaacccc acccctcaggctatgccagggggtgttgccaggggcacccgggcatcgccagtctagcccactccttcataaagccctcgcatcccaggag cgagcagagccagagcaggttggagaggagacgcatcacctccgctgctcgcggggtctagagtcga Nestin promoter (SEQ ID NO: 42)

gaaggcagcccccggaggtcaaaggctgggcacgcgggaggagaggccagagtcagaggctgcgggtatctcagatatgaaggaa agatgagagaggctcaggaagaggtaagaaaagacacaagagaccagagaagggagaagaattagagagggaggcagaggaccgc tgtctctacagacatagctggtagagactgggaggaagggatgaaccctgagcgcatgaaggggaaggaggtggctggtggtatatggagga tgtagctgggccagggaaaagatcctgcactaaaaatctgaagctaaaaataacaggacacggggtggagaggcgaaaggagggcaga ttgaggcagagagactgagaggcctggggatgtgggcattccggtagggcacacagttcacttgtcttctctctttttccaggaggccaaagatgct gacctcaagaactcataataccccagtggggaccaccgcattcatagccctgttacaagaagtgggagatgttccttttttgtcccagactggaaa tccattacatcccgaggctcaggttctgtggtggtcatctctgtgtggcttgttctgtgggcctacctaaagtcctaagcacagctctcaagcagatc cgaggcgactaagatgctagtaggggttgtctggagagaagagccgaggaggtgggctgtgatggatcagttcagctttcaaataaaaaggc gtttttatattctgtgtcgagttcgtgaacccctgtggtgggcttctccatctgtctgggttagtacctgccactatactggaataaggagacgcctgctt ccctcgagttggctggacaaggttatgagcatccgtgtacttatggggttgccagcttggtcctggatcgcccgggcccttcccccacccgttcggt tccccaccaccaccgcgctcgtacgtgcgtctccgcctgcagctcttgactcatcggggcccccgggtcacatgcgctcgctcggctctatagg cgccgcccctgcccacccccgcccgcgctgggagccgcagccgccgcactcctgctctctctgcgccgccgccgtcaccaccgccacc gccaccggctgagtctgcagtcctccgaaacgggccctct Homeobox Protein 9 promoter (HB9) promoter (SEQ ID NO: 43)

tgaataaatttaagcaggctaattaatatataaactagctcaatttgtcaagttgatttgtattttagttaattgtgaaagtaattaccacatggtca aattaacagctttctggaaatgaccaagcctgaggtttttatttccttcctgggtgaagaaaattcatttttccaagctcttgatgtgatgaataaaagtc ataaatctgggtgattggtgcaggcagagtctaaatggcttcatatttcattttaggtttaatagaaatattcatgctctgttttaatgaaattaaattgaa gggggatggggctagatggtggttagctgatgaattgacaaaaactaatcagctttattgggaaacaggtttaagggcacggacgtgtcaataac gctcagcctgacccctcttccattagctaggcaggctgattaga Tyrosine hydroxylase (TH) promoter (SEQ ID NO: 44)

CTGCTAGGGGCTGCTTCCCAGCTACTCCTCTTGGCTCCGTGGCTTGCCTTCCAGCCTGTGTG

CTGTCTGGAGAGCCTTTAAAGCCTCACTTCCACCAACTAGAAGTCTCTCCCCAACCCTGCCCTGA

CCTCAAGTGCACCTCTTCAAAGTCAGGTTTAGCAGCTGCAGCTGGGGGCCCTGAATCCCACCCC

TGCTGTCTTCCTTGAAGACAGAAGTGTTGGGAGCTGAGGATCTGGGCTAGAGACTGGCTGTATG

ATCCAGAGAAGTAGTGTGCTTCTGGGCCTCAGATTTCCCTTCTGTAGAACAGGTTTGTCTGAAAT

GGAGAGGTTGGTGCTCCTCTGCAGGGCCTAGTGGGAGTCACCATGAGTGGTTAAAAGATCCAGC

TTGTCTTTTGGTGAGCTTTGAGAGGAGGTAACAGGGCTGAGTTCTGGAAGCCTGACCAAGGGCA

GACTTAAGGGGCCTCTTGGAGTTGTTCTCATCAAATGGGGATGGGACACAGCTAAAGTGCCCAG

-continued

Sequences

GGCTTCTCTGTGCCCACAGATGCTTTAGATCTTGGCACAGTGTGGTCTACCAGCTGTCTCTCTCT

GTGTATATATATGTATTTCATAGACAGTGTACAGTGGCCTGGTTTGTGCTATCAGGCTGGATATGG

ACAGAGGCAAGAGTTTGTGGCAGCAGTTATCTCCCAAGAGAGTCCAAAGACATCATGTTTTCAAG

TTTAGGCCAGGTGCTACTTGAGAGAGCTCAGACACAGACAAAGGTCTGGAGAGCACATGTCCTC

CACCCCCACCTAGCTTCTGTTGCAAGCACCTCCAGCCGAGACAAGAGAACGAATTAAAAAGCAAT

ATTTGTGTCAGTGTAAGACATTTGCCGAAAGGTTAAATCCACATTCGTGTTGCTGCAGAGCAGCC

CCCTATGCAGGATTTGTTAGATACAGCTCCGTCCTACCCTGTGCCAGCTGAGCAAACGCCAGGCT

GGGTGGGGTGGAACCCAGCCTGGGTTTGCCTCACCCTGCAATCCCCCCAGCACCCTCTAAAGGA

GGACCCTGTGGTGGGCATGCAGACCTAGGGACTGGGCATAGATAACCTTTGGGTTTGGGCAACA

GCCCCCACTCCTCAGGATTGAAGGCTAAGGTGCAGCCAGCTCTGCCTTCATGGTGGGAATGTCT

CCACGTGACCCCTTTCTGGGCTGTGGAGAACACTCAGAGAAGAGTCCTGGGATGCCAGGCAGG

CCAGGGATGTGCTGGGCATGTTGAGACAGGAGTGGGCTAAGCCAGCAGAGTTGCTGACCCAGG

AAGAGTTCAGAAAGGGGCATGGAACATGGGGAGGGGTCCATAGTGAGAGAGAGCAGGCAGTGC

AGAGTAAATAGTCCCTGAGCTGGGGGTTATGGGATTTGCAGGAGCTTGCTCAGAGAAGGCAGAG

GAGAGATGCTGCGCCAAGCTGGGTATCACAGAGCCTCAGACTCCTGGAACAGGAACTGTGGGG

GTCAGGTCAGCAGGGGAGGTTAGGGAGTGTTCCCTTTGTACTGACTTAGCATTTATCCTGCTTCT

AGGGGGGAAGGGGGGCCAGTGGGGGATGCACAGCAAGGCAGTGATGTGGCAGGCAGCCTGCG

GGAGCTCCTGGTTCCTGGTGTGAAAAAGCTGGGAAGGAAGAGGGCTGGGTCTGGTAAGTACAG

CAGGCAGTTGGCTCCTGAGAGTCCAAGCCCTGTCTAGAGGGTGGAGTGAGATTTCAGAGGGAGA

GCTAAACGGGGTGGGGGCTGGGGAGTCCAGGCTTCTGGCTCCTGCTAATACTCAGTGTGCTGG

GTCCTCAGAACCTCAGGGTGGCCATTTTCAGGGTGAGAGCTCTGTCCTTTGGCACTTCTGCAGAC

TCCAGTATCCAGAGGAATAAAGATGGTACTCTTCCTCAGTTCCCTTAGTGAGAGGACACCTTTCTC

TGAAGGGCTTGGGCAGTTGTCCTGAACCATTGCCTGAAGGAAGGACTTGACTCCAGGGACATAG

AATGGGCTCAGCATAAGTCCCCTGTAGTAGAGAAAGGTCCCCTCTCTGGTCTCCTTAGAGATCCT

GTTTCCTTGGCTGAGGAAGCTAGGGTGGATCTTTGTGTAAGTGGGTGTGGATGCTCACTGGAAAT

CAAAAGGCCCCTTGGTGTTAGACCTTGGGGTGCCATGGGAGAGTTGATCACTGAGTGCGCCCTT

ACATGGGGGCCAGCTGAGAATGGGGCTGCCTCTAGCTCGAGACCATGATGCAGGGAGTGAGTG

GGGGAGTTCAGGATACTCTTAACTAAAGCAGAGGTCTGTCCCCCCAGGGAGGGGAGGTCAGAAG

ACCCTAGGGAGATGCCAAAGGCTAGGGTTGGCACCATGTTGCAGGCTGTGTCTTCAAGGAGATG

ATAATCAGAGGAATCGAACCTGCAAAAGTGGGCCAGTCTTAGATACACTATAGAGGAATAATCTT

CTGAAACATTCTGTGTCTCATAGGACCTGCCTGAGGACCCAGCCCCAGTGCCAGCACATACACT

GGGGCAGTGAGTAGATAGTATACTTTGTTACATGGGCTGGGGGGACATGGCCTGTGCCCTGGAG

GGGACTTGAAGACATCCAAAAAGCTAGTGAGAGGGCTCCTAGATTTATTTGTCTCCAAGGGCTAT

ATATAGCCTTCCTAACATGAACCCTTGGGTAATCCAGCATGGGCGCTCCCATATGCCCTGGTTTG

ATTAGAGAGCTCTAGATGTCTCCTGTCCCAGAACACCAGCCAGCCCCTGTCTTCATGTCGTGTCT

AGGGCGGAGGGTGATTCAGAGGCAGGTGCCTGCGACAGTGGATGCAATTAGATCTAATGGGAC

GGAGGCCTCTCTCGTCCGTCGCCCTCGCTCTGTGCCCACCCCCGCCTCCCTCAGGCACAGCAG

GCGTGGAGAGGATGCGCAGGAGGTAGGAGGTGGGGGACCCAGAGGGGCTTTGACGTCAGCCT

| Sequences |
| --- |

GGCCTTTAAGAGGCCGCCTGCCTGGCAAGGGCCGTGGAGACAGAACTCGGGACCACCAGCTTG

CACT

Myelin basic protein (MBP) promoter (SEQ ID NO: 45)

caccgtggcttttaacacttagagaaaatgcatccctctaatcaataagtcatcgacagtgggtagatggaggaacggcagtgcgtagta ggatgcgtgcaagcatagtctcgtgcatgggtgcatagatcgctgggcaggtggacaaggtgggggtggataaagaagtgggtagatgattg atgttaggtaaatatcactgggtggacagatgggtggtaggtggatggatggttagaatagtcagaagagggatggattgataaggtgaacag atgataaatgggtgatagactggaaggggttgtcaaaagaggataaggggaagtgtgagctagccgtatttctaaggtcagtaatagagttggga gaagaggttaagttacatccatttaaacctcacacgaagctgagagggaatggacttgctgccgttggtgaggaaagcgttgcatttcccgtgtg cttggttgtgaagtgctcaggtcccacatgaagcagtcaggttactgcggcttacagaggagccagatccaaatgccccgagtaagcacgtcc ccgagccagaggcctccagcggaatccgggagagggattgctcagtgccctgcttccctggactgtaagctgcagaaagatgtgggaagtcc tgttctccactgagaacactaaaagcaccttttgtcaaacgaccgcttcacatctgggcttgtgcactggtggcctttaaaccagagacaaccc acaagatacctaacctgcggggctctctggtacagtgagcaactcaggaaatgctttggcttgattgctgtgggctctcaggccatcgccctctgg agtggttcttttaatgagaacctgaagattggcccctgagccatgtataccaagcaagctcaatccaggnagctccctctggttggggcaagcta acgtgctccttgggccccgcgcgtaactgtgcgttttataggagacagctagttcaagaccccaggaagaaagcggctttgtcccctctaggc ctcgtacaggcccacattcatatctcattgttgttgcaggggaggcagatgcgatccagaacaatgggacctcggctgaggacacggcggtga cagactccaagcacacagcagacccaaagaataactggcaaggcgcccacccagctgacccagggaaccgcccccacttgatccgcctc ttttcccgagatgccccgggaagggaggacaacaccttcaaagacaggccctcagagtccgacgagcttcagaccatccaagaagatccc acagcagcttccgaagaattctgcagtcgacggtaccgcgggcccgggatc

---

The invention claimed is:

1. A method for treating diabetes and/or obesity, the method comprising administering to the intra-cerebrospinal fluid (CSF) of a subject in need thereof a recombinant adeno-associated virus (rAAV) vector comprising (i) an AAV capsid protein, wherein the AAV capsid protein is or is derived from AAV1, AAV2, or AAV9, and (ii) a gene construct comprising a nucleotide sequence encoding a fibroblast growth factor 21 (FGF21) operably linked to a promoter, wherein the treatment comprises expression of the encoded FGF21 in the central nervous system (CNS).

2. The method of claim 1, wherein the promoter is a ubiquitous promoter.

3. The method of claim 2, wherein the ubiquitous promoter is selected from a CAG promoter and a CMV promoter.

4. The method of claim 1, wherein the gene construct comprises at least one target sequence of a microRNA.

5. The method of claim 4, wherein the at least one target sequence of a microRNA is selected from a target sequence that bind to microRNAs expressed in the heart and/or a target sequence that binds to microRNAs expressed in the liver of a mammal.

6. The method of claim 5, wherein the gene construct comprises a target sequence of microRNA-122a and a target sequence of microRNA-1.

7. The method of claim 1, wherein the nucleotide sequence encoding FGF21 is operably linked to a ubiquitous promoter and at least one target sequence of a microRNA expressed in the liver and at least one target sequence of a microRNA expressed in the heart.

8. The method of claim 7, wherein the at least one target sequence of a microRNA expressed in the heart is selected from any of SEQ ID NO: 13 and 21-25 and the at least one target sequence of a microRNA expressed in the liver is selected from any of SEQ ID NO: 12 and 14-20.

9. The method of claim 1, wherein the nucleotide sequence encoding FGF21 is selected from:
   (a) a nucleotide sequence encoding a polypeptide comprising an amino acid sequence that has at least 95% sequence identity with the amino acid sequence of SEQ ID NO: 1, 2 or 3; or
   (b) a nucleotide sequence that has at least 95% sequence identity with the nucleotide sequence of SEQ ID NO: 4, 5, 6, 7, 10 or 11.

10. The method of claim 1, wherein the AAV capsid protein is or is derived from serotype 1 (AAV1).

11. The method of claim 1, wherein the rAAV vector is comprised in a pharmaceutical composition, together with one or more pharmaceutically acceptable ingredients.

12. The method of claim 1, wherein the treatment comprises expression of the encoded FGF21 in the brain of the subject.

13. The method of claim 1, wherein the treatment comprises expression of the encoded FGF21 in the hypothalamus, the cortex, the hippocampus, the cerebellum, the olfactory bulb, or any combination thereof of the subject.

14. The method of claim 1, wherein the rAAV vector comprises inverted terminal repeats (ITRs) flanking the gene construct.

15. The method of claim 1, wherein the AAV capsid protein is or is derived from AAV9.

16. The method of claim 1, wherein the rAAV vector is administered by intra-CSF administration via the cisterna magna.

17. The method of claim 1, wherein the AAV capsid protein is or is derived from AAV2.

18. The method of claim 1, wherein the rAAV vector is administered in a single dose.

\* \* \* \* \*

SEQUENCE LISTING

<160> NUMBER OF SEQ ID NOS: 70

<210> SEQ ID NO 1
<211> LENGTH: 209
<212> TYPE: PRT
<213> ORGANISM: Homo sapiens

<400> SEQUENCE: 1

```
Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
                20                  25                  30

Asp Ser Ser Pro Leu Leu Gln Phe Gly Gly Gln Val Arg Gln Arg Tyr
            35                  40                  45

Leu Tyr Thr Asp Asp Ala Gln Gln Thr Glu Ala His Leu Glu Ile Arg
        50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
                100                 105                 110

Ser Leu His Phe Asp Pro Glu Ala Cys Ser Phe Arg Glu Leu Leu Leu
            115                 120                 125

Glu Asp Gly Tyr Asn Val Tyr Gln Ser Glu Ala His Gly Leu Pro Leu
```

```
     130               135               140

His Leu Pro Gly Asn Lys Ser Pro His Arg Asp Pro Ala Pro Arg Gly
145               150               155               160

Pro Ala Arg Phe Leu Pro Leu Pro Gly Leu Pro Pro Ala Leu Pro Glu
                  165               170               175

Pro Pro Gly Ile Leu Ala Pro Gln Pro Pro Asp Val Gly Ser Ser Asp
                  180               185               190

Pro Leu Ser Met Val Gly Pro Ser Gln Gly Arg Ser Pro Ser Tyr Ala
                  195               200               205

Ser
```

<210> SEQ ID NO 2
<211> LENGTH: 210
<212> TYPE: PRT
<213> ORGANISM: Mus musculus

<400> SEQUENCE: 2

```
Met Glu Trp Met Arg Ser Arg Val Gly Thr Leu Gly Leu Trp Val Arg
1               5               10               15

Leu Leu Leu Ala Val Phe Leu Leu Gly Val Tyr Gln Ala Tyr Pro Ile
                  20               25               30

Pro Asp Ser Ser Pro Leu Leu Gln Phe Gly Gly Gln Val Arg Gln Arg
                  35               40               45

Tyr Leu Tyr Thr Asp Asp Asp Gln Asp Thr Glu Ala His Leu Glu Ile
     50               55               60

Arg Glu Asp Gly Thr Val Val Gly Ala Ala His Arg Ser Pro Glu Ser
65               70               75               80

Leu Leu Glu Leu Lys Ala Leu Lys Pro Gly Val Ile Gln Ile Leu Gly
                  85               90               95

Val Lys Ala Ser Arg Phe Leu Cys Gln Gln Pro Asp Gly Ala Leu Tyr
                  100               105               110

Gly Ser Pro His Phe Asp Pro Glu Ala Cys Ser Phe Arg Glu Leu Leu
                  115               120               125

Leu Glu Asp Gly Tyr Asn Val Tyr Gln Ser Glu Ala His Gly Leu Pro
     130               135               140

Leu Arg Leu Pro Gln Lys Asp Ser Pro Asn Gln Asp Ala Thr Ser Trp
145               150               155               160

Gly Pro Val Arg Phe Leu Pro Met Pro Gly Leu Leu His Glu Pro Gln
                  165               170               175

Asp Gln Ala Gly Phe Leu Pro Pro Glu Pro Pro Asp Val Gly Ser Ser
                  180               185               190

Asp Pro Leu Ser Met Val Glu Pro Leu Gln Gly Arg Ser Pro Ser Tyr
                  195               200               205

Ala Ser
     210
```

<210> SEQ ID NO 3
<211> LENGTH: 209
<212> TYPE: PRT
<213> ORGANISM: Canis lupus familiaris

<400> SEQUENCE: 3

```
Met Gly Trp Ala Glu Ala Gly Phe Glu His Leu Gly Leu Trp Val Pro
1               5               10               15

Val Leu Ala Val Leu Leu Leu Glu Ala Cys Arg Ala His Pro Ile Pro
                  20               25               30
```

```
Asp Ser Ser Pro Leu Leu Gln Phe Gly Gly Gln Val Arg Gln Arg Tyr
        35              40              45

Leu Tyr Thr Asp Asp Ala Gln Glu Thr Glu Ala His Leu Glu Ile Arg
    50              55              60

Ala Asp Gly Thr Val Val Gly Ala Ala Arg Gln Ser Pro Glu Ser Leu
65              70              75              80

Leu Glu Leu Lys Ala Leu Lys Pro Gly Val Ile Gln Ile Leu Gly Val
                85              90              95

Lys Thr Ser Arg Phe Leu Cys Gln Gly Pro Asp Gly Thr Leu Tyr Gly
            100             105             110

Ser Leu His Phe Asp Pro Val Ala Cys Ser Phe Arg Glu Leu Leu Leu
        115             120             125

Glu Asp Gly Tyr Asn Ile Tyr His Ser Glu Thr Leu Gly Leu Pro Leu
    130             135             140

Arg Leu Arg Pro His Asn Ser Ala Tyr Arg Asp Leu Ala Pro Arg Gly
145             150             155             160

Pro Ala Arg Phe Leu Pro Leu Pro Gly Leu Leu Pro Ala Pro Pro Glu
                165             170             175

Pro Pro Gly Ile Leu Ala Pro Glu Pro Pro Asp Val Gly Ser Ser Asp
            180             185             190

Pro Leu Ser Met Val Gly Pro Ser Gln Gly Arg Ser Pro Ser Tyr Ala
        195             200             205

Ser
```

```
<210> SEQ ID NO 4
<211> LENGTH: 630
<212> TYPE: DNA
<213> ORGANISM: Homo sapiens

<400> SEQUENCE: 4
atggactcgg acgagaccgg gttcgagcac tcaggactgt gggtttctgt gctggctggt      60
cttctgctgg gagcctgcca ggcacacccc atccctgact ccagtcctct cctgcaattc     120
gggggccaag tccggcagcg gtacctctac acagatgatg cccagcagac agaagcccac     180
ctggagatca gggaggatgg gacggtgggg ggcgctgctg accagagccc cgaaagtctc     240
ctgcagctga aagccttgaa gccgggagtt attcaaatct ggggagtcaa gacatccagg     300
ttcctgtgcc agcggccaga tggggccctg tatggatcgc tccactttga ccctgaggcc     360
tgcagcttcc gggagctgct tcttgaggac ggatacaatg tttaccagtc cgaagcccac     420
ggcctcccgc tgcacctgcc agggaacaag tccccacacc gggaccctgc accccgagga     480
ccagctcgct tcctgccact accaggcctg cccccccgcac tcccggagcc acccggaatc     540
ctggcccccc agcccccccga tgtgggctcc tcggaccctc tgagcatggt gggaccttcc     600
cagggccgaa gccccagcta cgcttcctga                                       630
```

```
<210> SEQ ID NO 5
<211> LENGTH: 630
<212> TYPE: DNA
<213> ORGANISM: Artificial sequence
<220> FEATURE:
<223> OTHER INFORMATION: Codon optimized Homo sapiens FGF21 - variant 1

<400> SEQUENCE: 5
atggattctg atgagacagg cttcgagcac agcggcctgt gggtttcagt tctggctgga      60
ctgctgctgg gagcctgtca ggcacaccct attccagata gcagccctct gctgcagttc     120
```

-continued

```
ggcggacaag tgcggcagag atacctgtac accgacgacg cccagcagac agaagcccac       180
ctggaaatca gagaggatgg cacagttggc ggagccgccg atcagtctcc tgaatctctg       240
ctccagctga aggccctgaa gcctggcgtg atccagatcc tgggcgtgaa aaccagccgg       300
ttcctgtgcc aaagacctga cggcgccctg tatggcagcc tgcactttga tcctgaggcc       360
tgcagcttca gagagctgct gcttgaggac ggctacaacg tgtaccagtc tgaggcccat       420
ggcctgcctc tgcatctgcc tggaaacaag agccctcaca gagatcccgc tcctagaggc       480
cctgccagat ttctgcctct tcctggattg cctcctgctc tgccagagcc tcctggaatt       540
ctggctcctc agcctcctga tgtgggcagc tctgatcctc tgagcatggt cggacctagc       600
cagggcagat ctcctagcta cgcctcttga                                        630
```

```
<210> SEQ ID NO 6
<211> LENGTH: 630
<212> TYPE: DNA
<213> ORGANISM: Artificial sequence
<220> FEATURE:
<223> OTHER INFORMATION: Codon optimized Homo sapiens FGF21 - variant 2

<400> SEQUENCE: 6
atggacagcg atgaaaccgg gttcgagcac agcggtctgt gggtgtccgt gctggccgga        60
ctgctcctgg gagcctgtca ggcgcacccc atccctgact cctcgccgct gctgcaattc       120
ggcggacaag tccgccagag atacctgtac accgacgacg cccagcagac cgaagcccac       180
ctggaaattc gggaggacgg gactgtggga ggcgctgcag atcagtcacc cgagtccctc       240
ctccaactga aggccttgaa gcccggcgtg attcagatcc tgggcgtgaa aacttcccgc       300
ttcctttgcc aacggccgga tggagctctg tacggatccc tgcacttcga ccccgaagcc       360
tgctcattcc gcgagctgct ccttgaggac ggctataacg tgtaccagtc tgaggcccat       420
ggactccccc tgcatctgcc cggcaacaag tcccctcacc gggatcctgc cccaagaggc       480
ccagctcggt ttctgcctct gccgggactg cctccagcgt tgcccgaacc ccctggtatc       540
ctggccccgc aaccacctga cgtcggttcg tcggacccgc tgagcatggt cggtccgagc       600
cagggaaggt ccccgtccta cgcatcctga                                        630
```

```
<210> SEQ ID NO 7
<211> LENGTH: 630
<212> TYPE: DNA
<213> ORGANISM: Artificial sequence
<220> FEATURE:
<223> OTHER INFORMATION: Codon optimized Homo sapiens FGF21 - variant 3

<400> SEQUENCE: 7
atggattccg acgaaactgg atttgaacat tcagggctgt gggtctctgt gctggctgga        60
ctgctgctgg gggcttgtca ggctcacccc atccctgaca gctcccctct gctgcagttc       120
ggaggacagg tgcggcagag atacctgtat accgacgatg cccagcagac agaggcacac       180
ctggagatca gggaggacgg aaccgtggga ggagcagccg atcagtctcc cgagagcctg       240
ctgcagctga aggccctgaa gcctggcgtg atccagatcc tgggcgtgaa gacatctcgg       300
tttctgtgcc agcggcccga cggcgccctg tacggctccc tgcacttcga tcccgaggcc       360
tgttctttta gggagctgct gctggaggac ggctacaacg tgtatcagag cgaggcacac       420
ggcctgccac tgcacctgcc tggcaataag tcccctcacc gcgatccagc acccaggggc       480
ccagcacgct tcctgcctct gccaggcctg cccccctgccc tgccagagcc acccggcatc       540
```

```
ctggcccccc agcctccaga tgtgggctcc agcgatcctc tgtcaatggt ggggccaagt      600
caggggcgga gtccttcata cgcatcataa                                       630

<210> SEQ ID NO 8
<211> LENGTH: 633
<212> TYPE: DNA
<213> ORGANISM: Mus musculus

<400> SEQUENCE: 8
atggaatgga tgagatctag agttgggacc ctgggactgt gggtccgact gctgctggct       60
gtcttcctgc tgggggtcta ccaagcatac cccatccctg actccagccc cctcctccag      120
tttgggggtc aagtccggca gaggtacctc tacacagatg acgaccaaga cactgaagcc      180
cacctggaga tcagggagga tggaacagtg gtaggcgcag cacaccgcag tccagaaagt      240
ctcctggagc tcaaagcctt gaagccaggg gtcattcaaa tcctgggtgt caaagcctct      300
aggtttcttt gccaacagcc agatggagct ctctatggat cgcctcactt tgatcctgag      360
gcctgcagct tcagagaact gctgctggag gacggttaca atgtgtacca gtctgaagcc      420
catggcctgc ccctgcgtct gcctcagaag gactccccaa accaggatgc aacatcctgg      480
ggacctgtgc gcttcctgcc catgccaggc ctgctccacg agcccaaga ccaagcagga      540 ttcctgcccc cagagccccc agatgtgggc tcctctgacc ccctgagcat ggtagagcct      600
ttacagggcc gaagccccag ctatgcgtcc tga                                   633

<210> SEQ ID NO 9
<211> LENGTH: 633
<212> TYPE: DNA
<213> ORGANISM: Artificial sequence
<220> FEATURE:
<223> OTHER INFORMATION: Codon optimized Mus musculus FGF21

<400> SEQUENCE: 9
atggaatgga tgagaagcag agtgggcacc ctgggcctgt gggtgcgact gctgctggct       60
gtgtttctgc tgggcgtgta ccaggcctac cccatccctg actctagccc cctgctgcag      120
tttggcggac aagtgcggca gagatacctg tacaccgacg acgaccagga caccgaggcc      180
cacctggaaa tccgcgagga tggcacagtc gtgggcgctg ctcacagaag ccctgagagc      240
ctgctggaac tgaaggccct gaagcccggc gtgatccaga tcctgggcgt gaaggccagc      300
agattcctgt gccagcagcc tgacggcgcc ctgtacggct ctcctcactt cgatcctgag      360
gcctgcagct tcagagagct gctgctggag gacggctaca cgtgtacca gtctgaggcc       420 cacggcctgc ccctgagact gcctcagaag gacagcccta accaggacgc cacaagctgg      480
ggacctgtgc ggttcctgcc tatgcctgga ctgctgcacg agccccagga tcaggctggc      540
tttctgcctc ctgagcctcc agacgtgggc agcagcgacc ctctgagcat ggtggaacct      600
ctgcagggca gaagccccag ctacgcctct tga                                   633

<210> SEQ ID NO 10
<211> LENGTH: 629
<212> TYPE: DNA
<213> ORGANISM: Canis lupus familiaris

<400> SEQUENCE: 10
atgggctggg ccgaggccgg gttcgagcac ctgggactgt gggtccctgt gctggctgtg       60
cttttgctaa agcctgccg ggcacatccg atccctgact ccagcccccT cctacaattt       120
ggaggtcaag ttcgacagcg gtacctctac accgacgatg cccaggagac agaggcccac      180
```

-continued

```
ctagagatca gggccgatgg cacagggtgg gggctgcccg ccagagccct gaaagtctcc     240
tggagctgaa agccctaaag ccaggggtca ttcaaatctt gggagtcaaa acatccaggt     300
tcctgtgcca gggcccagat gggacactat atggctcgct ccatttcgac cctgtggcct     360
gcagtttccg agaactgctt cttgaggatg ggtacaacat ctaccactcc gagacccttg     420
gtctcccgct tcgcctgcgc ccccacaact ccgcataccg ggacttggca ccccgcgggc     480
ctgcccgctt cctgccactg ccaggcctgc ttccagcacc cccagagcct ccagggatcc     540
tggccccgga gcctcctgac gtgggctcct cggaccctct gagcatggtg gggccttcac     600
agggccggag tcccagctat gcttcctaa                                        629
```

<210> SEQ ID NO 11
<211> LENGTH: 630
<212> TYPE: DNA
<213> ORGANISM: Artificial sequence
<220> FEATURE:
<223> OTHER INFORMATION: Codon optimized Canis lupus familiaris FGF21

<400> SEQUENCE: 11

```
atgggatggg ctgaggctgg attcgaacac ctgggactct gggtgcccgt cctggccgtg      60
ctgctcctgg aggcttgcag ggctcatccc atccctgaca gctccccact cctgcagttt     120
ggaggacagg tgaggcagcg gtacctgtat accgacgatg cccaggagac agaagctcac     180
ctggaaattc gggctgatgg aacagtggtc ggagctgccc gacagtcccc agagtctctc     240
ctggaactga aggccctcaa acccggagtg atccagattc tgggcgtcaa gacttctaga     300
ttcctgtgcc agggaccaga cggcaccctg tacggcagcc tgcatttcga tcctgtggcc     360
tgttcctttc gagagctcct gctcgaagac ggctacaaca tctatcactc tgagaccctg     420
ggactcccac tgcgactcag acctcataat agtgcctatc gagatctggc tcccaggggc     480
ccagctaggt ttctgccact ccccggactg ctccctgctc cacctgagcc accggcatt     540 ctggctccag aacctccaga cgtgggctct agtgatccac tgagtatggt cggcccctca     600 cagggggaggt cacctagcta cgccagctga                                       630
```

<210> SEQ ID NO 12
<211> LENGTH: 22
<212> TYPE: DNA
<213> ORGANISM: Artificial sequence
<220> FEATURE:
<223> OTHER INFORMATION: miRT-122a

<400> SEQUENCE: 12

```
caaacaccat tgtcacactc ca                                                22
```

<210> SEQ ID NO 13
<211> LENGTH: 22
<212> TYPE: DNA
<213> ORGANISM: Artificial sequence
<220> FEATURE:
<223> OTHER INFORMATION: miRT-1

<400> SEQUENCE: 13

```
ttacatactt ctttacattc ca                                                22
```

<210> SEQ ID NO 14
<211> LENGTH: 21
<212> TYPE: DNA
<213> ORGANISM: Artificial sequence
<220> FEATURE:

-continued

```
<223> OTHER INFORMATION: miRT-152

<400> SEQUENCE: 14
ccaagttctg tcatgcactg a                                            21

<210> SEQ ID NO 15
<211> LENGTH: 23
<212> TYPE: DNA
<213> ORGANISM: Artificial sequence
<220> FEATURE:
<223> OTHER INFORMATION: miRT-199a-5p

<400> SEQUENCE: 15
gaacaggtag tctgaacact ggg                                          23

<210> SEQ ID NO 16
<211> LENGTH: 22
<212> TYPE: DNA
<213> ORGANISM: Artificial sequence
<220> FEATURE:
<223> OTHER INFORMATION: miRT-199a-3p

<400> SEQUENCE: 16
taaccaatgt gcagactact gt                                           22

<210> SEQ ID NO 17
<211> LENGTH: 21
<212> TYPE: DNA
<213> ORGANISM: Artificial sequence
<220> FEATURE:
<223> OTHER INFORMATION: miRT-215

<400> SEQUENCE: 17
gtctgtcaat tcataggtca t                                            21

<210> SEQ ID NO 18
<211> LENGTH: 21
<212> TYPE: DNA
<213> ORGANISM: Artificial sequence
<220> FEATURE:
<223> OTHER INFORMATION: miRT-192

<400> SEQUENCE: 18
ggctgtcaat tcataggtca g                                            21

<210> SEQ ID NO 19
<211> LENGTH: 22
<212> TYPE: DNA
<213> ORGANISM: Artificial sequence
<220> FEATURE:
<223> OTHER INFORMATION: miRT-148a

<400> SEQUENCE: 19
acaaagttct gtagtgcact ga                                           22

<210> SEQ ID NO 20
<211> LENGTH: 22
<212> TYPE: DNA
<213> ORGANISM: Artificial sequence
<220> FEATURE:
<223> OTHER INFORMATION: miRT-194

<400> SEQUENCE: 20
tccacatgga gttgctgtta ca                                           22
```

-continued

<210> SEQ ID NO 21
<211> LENGTH: 22
<212> TYPE: DNA
<213> ORGANISM: Artificial sequence
<220> FEATURE:
<223> OTHER INFORMATION: miRT-133a

<400> SEQUENCE: 21
cagctggttg aaggggacca aa                                          22

<210> SEQ ID NO 22
<211> LENGTH: 22
<212> TYPE: DNA
<213> ORGANISM: Artificial sequence
<220> FEATURE:
<223> OTHER INFORMATION: miRT-206

<400> SEQUENCE: 22
ccacacactt ccttacattc ca                                          22

<210> SEQ ID NO 23
<211> LENGTH: 22
<212> TYPE: DNA
<213> ORGANISM: Artificial sequence
<220> FEATURE:
<223> OTHER INFORMATION: miRT-208a-5p

<400> SEQUENCE: 23
gtataacccg ggccaaaagc tc                                          22

<210> SEQ ID NO 24
<211> LENGTH: 22
<212> TYPE: DNA
<213> ORGANISM: Artificial sequence
<220> FEATURE:
<223> OTHER INFORMATION: miRT-208a-3p

<400> SEQUENCE: 24
acaagctttt tgctcgtctt at                                          22

<210> SEQ ID NO 25
<211> LENGTH: 21
<212> TYPE: DNA
<213> ORGANISM: Artificial sequence
<220> FEATURE:
<223> OTHER INFORMATION: miRT-499-5p

<400> SEQUENCE: 25
aaacatcact gcaagtctta a                                           21

<210> SEQ ID NO 26
<211> LENGTH: 133
<212> TYPE: DNA
<213> ORGANISM: Artificial sequence
<220> FEATURE:
<223> OTHER INFORMATION: chimeric intron composed of introns from human
      beta-globin and immunoglobulin heavy chain genes

<400> SEQUENCE: 26
gtaagtatca aggttacaag acaggtttaa ggagaccaat agaaactggg cttgtcgaga     60
cagagaagac tcttgcgttt ctgataggca cctattggtc ttactgacat ccactttgcc    120
tttctctcca cag                                                      133

<210> SEQ ID NO 27
<211> LENGTH: 1671

<212> TYPE: DNA
<213> ORGANISM: Artificial sequence
<220> FEATURE:
<223> OTHER INFORMATION: CAG promoter

<400> SEQUENCE: 27

```
gacattgatt attgactagt tattaatagt aatcaattac ggggtcatta gttcatagcc      60
catatatgga gttccgcgtt acataactta cggtaaatgg cccgcctggc tgaccgccca     120 acgaccccg  cccattgacg tcaataatga cgtatgttcc catagtaacg ccaatagga     180 ctttccattg acgtcaatgg gtggagtatt tacggtaaac tgcccacttg gcagtacatc     240
aagtgtatca tatgccaagt acgccccta ttgacgtcaa tgacggtaaa tggcccgcct     300
ggcattatgc ccagtacatg accttatggg actttcctac ttggcagtac atctacgtat     360
tagtcatcgc tattaccatg gtcgaggtga gccccacgtt ctgcttcact ctccccatct     420
cccccccctc cccaccccca attttgtatt tatttatttt ttaattattt tgtgcagcga     480 tggggcggg  ggggggggg  gggcgcgcgc caggcggggc ggggcggggc gaggggcggg     540
gcggggcgag gcggagaggt gcggcggcag ccaatcagag cggcgcgctc cgaaagtttc     600
cttttatggc gaggcggcgg cggcggcggc cctataaaaa gcgaagcgcg cggcgggcgg     660
gagtcgctgc gttgccttcg ccccgtgccc cgctccgcgc cgcctcgcgc cgcccgcccc     720
ggctctgact accgcgtta  ctcccacagg tgagcgggcg ggacggcccct tctcctccgg     780 gctgtaatta gcgcttggtt taatgacggc ttgtttcttt tctgtggctg cgtgaaagcc     840
ttgaggggct ccgggagggc cctttgtgcg ggggagcgg  ctcggggggt gcgtgcgtgt     900
gtgtgtgcgt ggggagcgcc gcgtgcggct ccgcgctgcc cggcggctgt gagcgctgcg     960
ggcgcggcgc ggggctttgt gcgctccgca gtgtgcgcga ggggagcgcg gccggggggcg    1020 gtgccccgcg gtgcggggggg ctgcgagggg aacaaaggct gcgtgcgggg tgtgtgcgtg    1080
ggggggtgag caggggggtgt gggcgcgtcg gtcgggctgc aacccccct  gcaccccct     1140 ccccgagttg ctgagcacgg cccggcttcg ggtgcggggc tccgtacggg gcgtggcgcg    1200
gggctcgccg tgccgggcgg ggggtggcgg caggtggggg tgccgggcgg ggcggggccg    1260
cctcgggccg gggagggctc gggggagggg cgcggcggcc cccggagcgc cggcggctgt    1320
cgaggcgcgg cgagccgcag ccattgcctt ttatggtaat cgtgcgagag ggcgcaggga    1380
cttcctttgt cccaaatctg tgcggagccg aaatctggga ggcgccgccg caccccctct    1440
agcgggcgcg gggcgaagcg gtgcggcgcc ggcaggaagg aaatgggcgg ggagggcctt    1500
cgtgcgtcgc cgcgccgccg tcccttctc  cctctccagc ctcggggctg tccgcggggg    1560
gacggctgcc ttcggggggg acggggcagg gcggggttcg gcttctggcg tgtgaccggc    1620
ggctctagag cctctgctaa ccatgttcat gccttcttct ttttcctaca g            1671
```

<210> SEQ ID NO 28
<211> LENGTH: 212
<212> TYPE: DNA
<213> ORGANISM: Artificial sequence
<220> FEATURE:
<223> OTHER INFORMATION: CMV promoter

<400> SEQUENCE: 28

```
gtgatgcggt tttggcagta caccaatggg cgtggatagc ggtttgactc acggggattt      60
ccaagtctcc accccattga cgtcaatggg agtttgtttt ggcaccaaaa tcaacgggac     120
tttccaaaat gtcgtaacaa ctgcgatcgc ccgccccgtt gacgcaaatg ggcggtaggc     180
```

-continued

```
gtgtacggtg ggaggtctat ataagcagag ct                              212

<210> SEQ ID NO 29
<211> LENGTH: 380
<212> TYPE: DNA
<213> ORGANISM: Artificial sequence
<220> FEATURE:
<223> OTHER INFORMATION: CMV enhancer

<400> SEQUENCE: 29
ggcattgatt attgactagt tattaatagt aatcaattac ggggtcatta gttcatagcc      60
catatatgga gttccgcgtt acataactta cggtaaatgg cccgcctggc tgaccgccca     120
acgacccccg cccattgacg tcaataatga cgtatgttcc catagtaacg ccaataggga     180
ctttccattg acgtcaatgg gtggagtatt tacggtaaac tgcccacttg gcagtacatc     240
aagtgtatca tatgccaagt ccgcccccta ttgacgtcaa tgacggtaaa tggcccgcct     300
ggcattatgc ccagtacatg accttacggg actttcctac ttggcagtac atctacgtat     360
tagtcatcgc tattaccatg                                               380

<210> SEQ ID NO 30
<211> LENGTH: 128
<212> TYPE: DNA
<213> ORGANISM: Artificial sequence
<220> FEATURE:
<223> OTHER INFORMATION: Truncated AAV2 5' ITR

<400> SEQUENCE: 30
gcgcgctcgc tcgctcactg aggccgcccg ggcaaagccc gggcgtcggg cgacctttgg      60
tcgcccggcc tcagtgagcg agcgagcgcg cagagaggga gtggccaact ccatcactag     120
gggttcct                                                            128

<210> SEQ ID NO 31
<211> LENGTH: 128
<212> TYPE: DNA
<213> ORGANISM: Artificial sequence
<220> FEATURE:
<223> OTHER INFORMATION: Truncated AAV2 3' ITR

<400> SEQUENCE: 31
aggaacccct agtgatggag ttggccactc cctctctgcg cgctcgctcg ctcactgagg      60
ccgggcgacc aaaggtcgcc cgacgcccgg gctttgcccg ggcggcctca gtgagcgagc     120
gagcgcgc                                                            128

<210> SEQ ID NO 32
<211> LENGTH: 122
<212> TYPE: DNA
<213> ORGANISM: Artificial sequence
<220> FEATURE:
<223> OTHER INFORMATION: SV40 polyadenylation signal

<400> SEQUENCE: 32
taagatacat tgatgagttt ggacaaacca caactagaat gcagtgaaaa aaatgcttta      60
tttgtgaaat ttgtgatgct attgctttat ttgtaaccat tataagctgc aataaacaag     120
tt                                                                  122

<210> SEQ ID NO 33
<211> LENGTH: 449
<212> TYPE: DNA
<213> ORGANISM: Artificial sequence
```

```
<220> FEATURE:
<223> OTHER INFORMATION: Rabbit beta-globin polyadenylation signal

<400> SEQUENCE: 33
gatctttttc cctctgccaa aaattatggg gacatcatga agccccttga gcatctgact       60
tctggctaat aaaggaaatt tattttcatt gcaatagtgt gttggaattt tttgtgtctc      120
tcactcggaa ggacatatgg gagggcaaat catttaaaac atcagaatga gtatttggtt      180
tagagtttgg caacatatgc ccatatgctg gctgccatga caaaggttg gctataaaga      240 ggtcatcagt atatgaaaca gccccctgct gtccattcct tattccatag aaaagccttg      300
acttgaggtt agattttttt tatattttgt tttgtgttat tttttttcttt aacatcccta     360 aaattttcct tacatgtttt actagccaga ttttttcctcc tctcctgact actcccagtc     420
atagctgtcc ctcttctctt atggagatc                                        449

<210> SEQ ID NO 34
<211> LENGTH: 592
<212> TYPE: DNA
<213> ORGANISM: Artificial sequence
<220> FEATURE:
<223> OTHER INFORMATION: CMV promoter and CMV enhancer sequence

<400> SEQUENCE: 34
ggcattgatt attgactagt tattaatagt aatcaattac ggggtcatta gttcatagcc       60
catatatgga gttccgcgtt acataactta cggtaaatgg cccgcctggc tgaccgccca      120
acgacccccg cccattgacg tcaataatga cgtatgttcc catagtaacg ccaatagggga      180 ctttccattg acgtcaatgg gtggagtatt tacggtaaac tgcccacttg gcagtacatc      240
aagtgtatca tatgccaagt ccgcccccta ttgacgtcaa tgacggtaaa tggcccgcct      300
ggcattatgc ccagtacatg accttacggg actttcctac ttggcagtac atctacgtat      360
tagtcatcgc tattaccatg gtgatgcggt tttggcagta caccaatggg cgtggatagc      420
ggtttgactc acggggattt ccaagtctcc accccattga cgtcaatggg agtttgtttt      480
ggcaccaaaa tcaacgggac tttccaaaat gtcgtaacaa ctgcgatcgc ccgcccgtt      540 gacgcaaatg ggcggtaggc gtgtacggtg ggaggtctat ataagcagag ct            592

<210> SEQ ID NO 35
<211> LENGTH: 7319
<212> TYPE: DNA
<213> ORGANISM: Artificial sequence
<220> FEATURE:
<223> OTHER INFORMATION: pAAV-CAG-moFGF21-dmiRT

<400> SEQUENCE: 35
agtgagcgag cgagcgcgca gctgcattaa tgaatcggcc aacgcgcggg gagaggcggt       60
ttgcgtattg ggcgctcttc cgcttcctcg ctcactgact cgctgcgctc ggtcgttcgg      120
ctgcggcgag cggtatcagc tcactcaaag gcggtaatac ggttatccac agaatcaggg      180
gataacgcag gaaagaacat gtgagcaaaa ggccagcaaa aggccaggaa ccgtaaaaag      240
gccgcgttgc tggcgttttt ccataggctc cgcccccctg acgagcatca caaaaatcga      300
cgctcaagtc agaggtggcg aaacccgaca ggactataaa gataccaggc gtttccccct      360
ggaagctccc tcgtgcgctc tcctgttccg accctgccgc ttaccggata cctgtccgcc      420
tttctccctt cgggaagcgt ggcgctttct catagctcac gctgtaggta tctcagttcg      480
gtgtaggtcg ttcgctccaa gctgggctgt gtgcacgaac cccccgttca gcccgaccgc      540
```

-continued

```
tgcgccttat ccggtaacta tcgtcttgag tccaacccgg taagacacga cttatcgcca        600
ctggcagcag ccactggtaa caggattagc agagcgaggt atgtaggcgg tgctacagag        660
ttcttgaagt ggtggcctaa ctacggctac actagaagaa cagtatttgg tatctgcgct        720
ctgctgaagc cagttacctt cggaaaaaga gttggtagct cttgatccgg caaacaaacc        780
accgctggta gcggtggttt ttttgtttgc aagcagcaga ttacgcgcag aaaaaaagga        840
tctcaagaag atcctttgat cttttctacg gggtctgacg ctcagtggaa cgaaaactca        900
cgttaaggga ttttggtcat gagattatca aaaaggatct tcacctagat ccttttaaat        960
taaaaatgaa gttttaaatc aatctaaagt atatatgagt aaacttggtc tgacagttac       1020
caatgcttaa tcagtgaggc acctatctca gcgatctgtc tatttcgttc atccatagtt       1080
gcctgactcc ccgtcgtgta gataactacg atacgggagg gcttaccatc tggccccagt       1140
gctgcaatga taccgcgaga cccacgctca ccggctccag atttatcagc aataaaccag       1200
ccagccggaa gggccgagcg cagaagtggt cctgcaactt tatccgcctc catccagtct       1260
attaattgtt gccgggaagc tagagtaagt agttcgccag ttaatagttt gcgcaacgtt       1320
gttgccattg ctacaggcat cgtggtgtca cgctcgtcgt ttggtatggc ttcattcagc       1380
tccggttccc aacgatcaag gcgagttaca tgatccccca tgttgtgcaa aaaagcggtt       1440
agctccttcg gtcctccgat cgttgtcaga agtaagttgg ccgcagtgtt atcactcatg       1500
gttatggcag cactgcataa ttctcttact gtcatgccat ccgtaagatg cttttctgtg       1560
actggtgagt actcaaccaa gtcattctga aatagtgta tgcggcgacc gagttgctct       1620
tgcccggcgt caatacggga taataccgcg ccacatagca gaactttaaa agtgctcatc       1680
attggaaaac gttcttcggg gcgaaaactc tcaaggatct taccgctgtt gagatccagt       1740
tcgatgtaac ccactcgtgc acccaactga tcttcagcat cttttacttt caccagcgtt       1800
tctgggtgag caaaaacagg aaggcaaaat gccgcaaaaa agggaataag ggcgacacgg       1860
aaatgttgaa tactcatact cttcctttt caatattatt gaagcattta tcagggttat       1920
tgtctcatga gcggatacat atttgaatgt atttagaaaa ataaacaaat aggggttccg       1980
cgcacatttc cccgaaaagt gccacctgac gtctaagaaa ccattattat catgacatta       2040
acctataaaa ataggcgtat cacgaggccc tttcgtctcg cgcgtttcgg tgatgacggt       2100
gaaaacctct gacacatgca gctcccggag acggtcacag cttgtctgta agcggatgcc       2160
gggagcagac aagcccgtca gggcgcgtca gcgggtgttg gcgggtgtcg gggctggctt       2220
aactatgcgg catcagagca gattgtactg agagtgcacc atatgcggtg tgaaataccg       2280
cacagatgcg taaggagaaa ataccgcatc aggcgattcc aacatccaat aaatcataca       2340
ggcaaggcaa agaattagca aaattaagca ataaagcctc agagcataaa gctaaatcgg       2400
ttgtaccaaa aacattatga ccctgtaata cttttgcggg agaagccttt atttcaacgc       2460
aaggataaaa attttttagaa ccctcatata tttttaaatgc aatgcctgag taatgtgtag       2520
gtaaagattc aaacgggtga aaaggccgg agacagtcaa atcaccatca atatgatatt       2580
caaccgttct agctgataaa ttcatgccgg agagggtagc tattttttgag aggtctctac       2640 aaaggctatc aggtcattgc ctgagagtct ggagcaaaca agagaatcga tgaacggtaa       2700
tcgtaaaact agcatgtcaa tcatatgtac cccggttgat aatcagaaaa gccccaaaaa       2760
caggaagatt gtataagcaa atatttaaat tgtaagcgtt aatattttgt taaaattcgc       2820
gttaaatttt tgttaaatca gctcattttt taaccaatag gccgaaatcg gcaaaatccc       2880
ttataaatca aaagaataga ccgagatagg gttgagtgtt gttccagttt ggaacaagag       2940
```

-continued

```
tccactatta aagaacgtgg actccaacgt caaagggcga aaaaccgtct atcagggcga   3000
tggcccacta cgtgaaccat caccctaatc aagttttttg gggtcgaggt gccgtaaagc   3060
actaaatcgg aaccctaaag ggagcccccg atttagagct tgacggggaa agccggcgaa   3120
cgtggcgaga aaggaaggga agaaagcgaa aggagcgggc gctagggcgc tggcaagtgt   3180
agcggtcacg ctgcgcgtaa ccaccacacc cgccgcgctt aatgcgccgc tacagggcgc   3240
gtactatggt tgctttgacg agcacgtata acgtgctttc ctcgttagaa tcagagcggg   3300
agctaaacag gaggccgatt aaagggattt tagacaggaa cggtacgcca gaatcctgag   3360
aagtgttttt ataatcagtg aggccaccga gtaaaagagt ctgtccatca cgcaaattaa   3420
ccgttgtcgc aatacttctt tgattagtaa taacatcact tgcctgagta gaagaactca   3480
aactatcggc cttgctggta atatccagaa caatattacc gccagccatt gcaacggaat   3540
cgccattcgc cattcaggct gcgcaactgt tgggaagggc gatcggtgcg ggcctcttcc   3600
actgaggccc agctgcgcgc tcgctcgctc actgaggccg cccgggcaaa gcccgggcgt   3660
cgggcgacct ttggtcgccc ggcctcagtg agcgagcgag cgcgcagaga gggagtggcc   3720
aactccatca ctaggggttc cttgtagtta atgattaacc cgccatgcta cttatctact   3780
cgacattgat tattgactag ttattaatag taatcaatta cggggtcatt agttcatagc   3840
ccatatatgg agttccgcgt tacataactt acggtaaatg gcccgcctgg ctgaccgccc   3900
aacgaccccc gcccattgac gtcaataatg acgtatgttc ccatagtaac gccaataggg   3960
actttccatt gacgtcaatg ggtggagtat ttacggtaaa ctgcccactt ggcagtacat   4020
caagtgtatc atatgccaag tacgccccct attgacgtca atgacggtaa atggcccgcc   4080
tggcattatg cccagtacat gaccttatgg gactttccta cttggcagta catctacgta   4140
ttagtcatcg ctattaccat ggtcgaggtg agccccacgt tctgcttcac tctccccatc   4200
tcccccccct ccccaccccc aattttgtat ttatttattt tttaattatt ttgtgcagcg   4260 atggggggcgg gggggggggg ggggcgcgcg ccaggcgggg cggggcgggg cgaggggcgg   4320
ggcggggcga ggcggagagg tgcggcggca gccaatcaga gcggcgcgct ccgaaagttt   4380
ccttttatgg cgaggcggcg gcggcggcgg ccctataaaa agcgaagcgc gcggcgggcg   4440
ggagtcgctg cgttgccttc gccccgtgcc ccgctccgcg ccgcctcgcg ccgcccgccc   4500
cggctctgac tgaccgcgtt actcccacag gtgagcgggc gggacggccc ttctcctccg   4560
ggctgtaatt agcgcttggt ttaatgacgg cttgtttctt ttctgtggct gcgtgaaagc   4620
cttgaggggc tccgggaggg ccctttgtgc ggggggagcg gctcggggggg tgcgtgcgtg   4680 tgtgtgtgcg tggggagcgc cgcgtgcggc tccgcgctgc ccggcggctg tgagcgctgc   4740
gggcgcggcg cggggctttg tgcgctccgc agtgtgcgcg aggggagcgc ggccggggggc   4800 ggtgccccgc ggtgcggggg gctgcgaggg gaacaaaggc tgcgtgcggg gtgtgtgcgt   4860 ggggggggtga gcaggggggtg tgggcgcgtc ggtcgggctg caaccccccc tgcacccccc   4920
tccccgagtt gctgagcacg gcccggcttc gggtgcgggg ctccgtacgg ggcgtggcgc   4980
ggggctcgcc gtgccgggcg gggggtggcg gcaggtgggg gtgccgggcg gggcgggggcc   5040 gcctcgggcc gggggagggct cggggagggg gcgcggcggc ccccgagcg ccggcggctg   5100 tcgaggcgcg gcgagccgca gccattgcct tttatggtaa tcgtgcgaga gggcgcaggg   5160
acttcctttg tcccaaatct gtgcggagcc gaaatctggg aggcgccgcc gcaccccctc   5220
tagcgggcgc ggggcgaagc ggtgcggcgc cggcaggaag gaaatgggcg gggagggcct   5280
```

-continued

```
tcgtgcgtcg ccgcgccgcc gtccccttct ccctctccag cctcggggct gtccgcgggg      5340
ggacggctgc cttcgggggg gacggggcag ggcggggttc ggcttctggc gtgtgaccgg      5400
cggctctaga gcctctgcta accatgttca tgccttcttc ttttttcctac agctcctggg     5460 caacgtgctg gttattgtgc tgtctcatca ttttggcaaa gaattgatta attcgagcga      5520
acgcgtcgag tcgctcggta cgatttaaat tgaattggcc tcgagcgcaa gcttgagcta      5580
gcgccaccat ggaatggatg agaagcagag tgggcaccct gggcctgtgg gtgcgactgc      5640
tgctggctgt gtttctgctg ggcgtgtacc aggcctaccc catccctgac tctagccccc      5700
tgctgcagtt tggcggacaa gtgcggcaga gatacctgta caccgacgac gaccaggaca      5760
ccgaggccca cctggaaatc cgcgaggatg gcacagtcgt gggcgctgct cacagaagcc      5820
ctgagagcct gctggaactg aaggccctga agcccggcgt gatccagatc ctgggcgtga      5880
aggccagcag attcctgtgc cagcagcctg acggcgccct gtacggctct cctcacttcg      5940
atcctgaggc ctgcagcttc agagagctgc tgctggagga cggctacaac gtgtaccagt      6000
ctgaggccca cggcctgccc ctgagactgc ctcagaagga cagccctaac caggacgcca      6060
caagctgggg acctgtgcgg ttcctgccta tgcctggact gctgcacgag ccccaggatc      6120
aggctggctt tctgcctcct gagcctccag acgtgggcag cagcgaccct ctgagcatgg      6180
tggaacctct gcagggcaga agccccagct acgcctcttg agaatgcggg cccggtaccc      6240
ccgacgcggc cgctaattct agatcgcgaa caaacaccat tgtcacactc cagtatacac      6300
aaacaccatt gtcacactcc agatatcaca aacaccattg tcacactcca aggcgaacaa      6360
acaccattgt cacactccaa ggctattcta gatcgcgaat tacatacttc tttacattcc      6420
agtatacatt acatacttct ttacattcca gatatcatta catacttctt tacattccaa      6480
ggcgaattac atacttcttt acattccaag gctacctgag gcccgggggt acctcttaat      6540
taactggcct catgggcctt ccgctcactg cccgctttcc agtcgggaaa cctgtcgtgc      6600
cagtcaggtg caggctgcct atcagaaggt ggtggctggt gtggccaatg ccctggctca      6660
caaataccac tgagatcttt ttccctctgc caaaaattat ggggacatca tgaagcccct      6720
tgagcatctg acttctggct aataaaggaa atttattttc attgcaatag tgtgttggaa      6780
ttttttgtgt ctctcactcg gaaggacata tgggagggca aatcatttaa aacatcagaa      6840
tgagtatttg gtttagagtt tggcaacata tgcccatatg ctggctgcca tgaacaaagg      6900
ttggctataa agaggtcatc agtatatgaa acagcccccct gctgtccatt ccttattcca      6960
tagaaaagcc ttgacttgag gttagatttt ttttatattt tgttttgtgt tattttttc       7020 tttaacatcc ctaaaatttt ccttacatgt tttactagcc agattttttcc tcctctcctg      7080 actactccca gtcatagctg tccctcttct cttatggaga tccctcgacc tgcagcccaa      7140
gctgtagata agtagcatgg cgggttaatc attaactaca aggaacccct agtgatggag      7200
ttggccactc cctctctgcg cgctcgctcg ctcactgagg ccgggcgacc aaaggtcgcc      7260
cgacgcccgg gctttgcccg ggcggcctca gtgagcgagc gagcgcgcag ctggcgtaa       7319
```

```
<210> SEQ ID NO 36
<211> LENGTH: 411
<212> TYPE: DNA
<213> ORGANISM: Artificial sequence
<220> FEATURE:
<223> OTHER INFORMATION: mini-CMV promoter

<400> SEQUENCE: 36
tatgccaagt acgccccta ttgacgtcaa tgacggtaaa tggcccgcct ggcattatgc       60
```

```
ccagtacatg accttatggg actttcctac ttggcagtac atctacgtat tagtcatcgc      120
tattaccatg gtgatgcggt tttggcagta catcaatggg cgtggatagc ggtttgactc      180
acggggattt ccaagtctcc accccattga cgtcaatggg agtttgtttt ggcaccaaaa      240
tcaacgggac tttccaaaat gtcgtaacaa ctccgcccca ttgacgcaaa tgggcggtag      300
gcgtgtacgg tgggaggtct atataagcag agctctctgg ctaactagag aacccactgc      360
ttaactggct tatcgaaatt aatacgactc actataggga gacccaagct t              411
```

```
<210> SEQ ID NO 37
<211> LENGTH: 1178
<212> TYPE: DNA
<213> ORGANISM: Artificial sequence
<220> FEATURE:
<223> OTHER INFORMATION: EF1alpha promoter

<400> SEQUENCE: 37
ggctccggtg cccgtcagtg ggcagagcgc acatcgccca cagtccccga gaagttgggg       60
ggaggggtcg gcaattgaac cggtgcctag agaaggtggc gcggggtaaa ctgggaaagt      120
gatgtcgtgt actggctccg cctttttccc gagggtgggg gagaaccgta tataagtgca      180
gtagtcgccg tgaacgttct ttttcgcaac gggtttgccg ccagaacaca ggtaagtgcc      240
gtgtgtggtt cccgcgggcc tggcctcttt acgggttatg gcccttgcgt gccttgaatt      300
acttccactg gctgcagtac gtgattcttg atcccgagct tcgggttgga agtgggtggg      360
agagttcgag gccttgcgct taaggagccc cttcgcctcg tgcttgagtt gaggcctggc      420
ctgggcgctg gggccgccgc gtgcgaatct ggtggcacct tcgcgcctgt ctcgctgctt      480
tcgataagtc tctagccatt taaaattttt gatgacctgc tgcgacgctt tttttctggc      540
aagatagtct tgtaaatgcg ggccaagatc tgcacactgg tatttcggtt tttggggccg      600
cgggcggcga cggggcccgt gcgtcccagc gcacatgttc ggcgaggcgg ggcctgcgag      660
cgcggccacc gagaatcgga cgggggtagt ctcaagctgg ccggcctgct ctggtgcctg      720
gcctcgcgcc gccgtgtatc gccccgccct gggcggcaag gctggcccgg tcggcaccag      780
ttgcgtgagc ggaaagatgg ccgcttcccg gccctgctgc agggagctca aaatggagga      840
cgcggcgctc gggagagcgg gcgggtgagt cacccacaca aaggaaaagg cctttccgt      900 cctcagccgt cgcttcatgt gactccacgg agtaccgggc gccgtccagg cacctcgatt      960
agttctcgag ctttttggagt acgtcgtctt taggttgggg ggaggggttt tatgcgatgg     1020
agtttcccca cactgagtgg gtggagactg aagttaggcc agcttggcac ttgatgtaat     1080
tctccttgga atttgccctt tttgagtttg gatcttggtt cattctcaag cctcagacag     1140
tggttcaaag ttttttttctt ccatttcagg tgtcgtga                            1178
```

```
<210> SEQ ID NO 38
<211> LENGTH: 623
<212> TYPE: DNA
<213> ORGANISM: Artificial sequence
<220> FEATURE:
<223> OTHER INFORMATION: RSV promoter

<400> SEQUENCE: 38
catgtttgac agcttatcat cgcagatccg tatggtgcac tctcagtaca atctgctctg       60
atgccgcata gttaagccag tatctgctcc ctgcttgtgt gttggaggtc gctgagtagt      120
gcgcgagcaa aatttaagct acaacaaggc aaggcttgac cgacaattgc atgaagaatc      180
```

-continued

```
tgcttagggt taggcgtttt gcgctgcttc gcgatgtacg ggccagatat tcgcgtatct        240
gaggggacta gggtgtgttt aggcgaaaag cggggcttcg gttgtacgcg gttaggagtc        300
ccctcaggat atagtagttt cgcttttgca tagggagggg gaaatgtagt cttatgcaat        360
actcttgtag tcttgcaaca tggtaacgat gagttagcaa catgccttac aaggagagaa        420
aaagcaccgt gcatgccgat tggtggaagt aaggtggtac gatcgtgcct tattaggaag        480
gcaacagacg ggtctgacat ggattggacg aaccactaaa ttccgcattg cagagatatt        540
gtatttaagt gcctagctcg atacaataaa cgccatttga ccattcacca cattggtgtg        600
cacctccaag ctgggtacca gct                                                623

<210> SEQ ID NO 39
<211> LENGTH: 448
<212> TYPE: DNA
<213> ORGANISM: Artificial sequence
<220> FEATURE:
<223> OTHER INFORMATION: Synapsin 1 promoter

<400> SEQUENCE: 39
ctgcgctctc aggcacgaca cgactcctcc gctgcccacc gcagactgag gcagcgctga         60
gtcgccggcg ccgcagcgca gatggtcgcg cccgtgcccc cctatctcgc gcctcgcgtg        120
gtgcggtccg gctgggccgg cggcggcgcg gacgcgacca aggtggccgg gaaggggagt        180
ttgcggggga ccggcgagtg acgtcagcgc gccttcagtg ctgaggcggc ggtggcgcgc        240
gccgccaggc gggggcgaag gcactgtccg cggtgctgaa gctggcagtg cgcacgcgcc        300
tcgccgcatc ctgtttcccc tccccctctc tgatagggga tgcgcaattt ggggaatggg        360
ggttgggtgc ttgtccagtg ggtcggggtc ggtcgtcagg taggcacccc caccccgcct        420
catcctggtc ctaaaaccca cttgcact                                          448

<210> SEQ ID NO 40
<211> LENGTH: 1296
<212> TYPE: DNA
<213> ORGANISM: Artificial sequence
<220> FEATURE:
<223> OTHER INFORMATION: Calcium/calmodulin-dependent protein kinase II
      (CaMKII) promoter

<400> SEQUENCE: 40
taacattatg gccttaggtc acttcatctc catggggttc ttcttctgat tttctagaaa         60
atgagatggg ggtgcagaga gcttcctcag tgacctgccc agggtcacat cagaaatgtc        120
agagctagaa cttgaactca gattactaat cttaaattcc atgccttggg ggcatgcaag        180
tacgatatac agaaggagtg aactcattag ggcagatgac caatgagttt aggaaagaag        240
agtccagggc agggtacatc tacaccaccc gcccagccct gggtgagtcc agccacgttc        300
acctcattat agttgcctct ctccagtcct accttgacgg gaagcacaag cagaaactgg        360
gacaggagcc ccaggagacc aaatcttcat ggtccctctg ggaggatggg tggggagagc        420
tgtggcagag gcctcaggag gggccctgct gctcagtggt gacagatagg ggtgagaaag        480
cagacagagt cattccgtca gcattctggg tctgtttggt acttcttctc acgctaaggt        540
ggcggtgtga tatgcacaat ggctaaaaag cagggagagc tggaaagaaa caaggacaga        600
gacagaggcc aagtcaacca gaccaattcc cagaggaagc aaagaaacca ttacagagac        660 tacaagggggg aagggaagga gagatgaatt agcttcccct gtaaaccttta gaacccagct       720 gttgccaggg caacggggca atacctgtct cttcagagga gatgaagttg ccagggtaac       780
```

-continued

```
tacatcctgt ctttctcaag gaccatccca gaatgtggca cccactagcc gttaccatag      840
caactgcctc tttgccccac ttaatcccat cccgtctgtt aaaagggccc tatagttgga      900
ggtgggggag gtaggaagag cgatgatcac ttgtggacta agtttgttcg catccccttc      960 tccaacccc  tcagtacatc accctggggg aacagggtcc acttgctcct gggcccacac     1020
agtcctgcag tattgtgtat ataaggccag ggcaaagagg agcaggtttt aaagtgaaag     1080
gcaggcaggt gttggggagg cagttaccgg ggcaacggga acaggcgtt  tcggaggtgg     1140 ttgccatggg gacctggatg ctgacgaagg ctcgcgaggc tgtgagcagc cacagtgccc     1200
tgctcagaag ccccaagctc gtcagtcaag ccggttctcc gtttgcactc aggagcacgg     1260
gcaggcgagt ggcccctagt tctgggggca gcgggg                              1296
```

<210> SEQ ID NO 41
<211> LENGTH: 706
<212> TYPE: DNA
<213> ORGANISM: Artificial sequence
<220> FEATURE:
<223> OTHER INFORMATION: Glial fibrillary acidic protein (GFAP) promoter

<400> SEQUENCE: 41

```
cgcgtgatct aacatatcct ggtgtggagt aggggacgct gctctgacag aggctcgggg       60
gcctgagctg gctctgtgag ctggggagga ggcagacagc caggccttgt ctgcaagcag      120
acctggcagc attgggctgg ccgccccca gggcctcctc ttcatgccca gtgaatgact      180
caccttggca cagacacaat gttcggggtg ggcacagtgc ctgcttccg  ccgcacccca      240 gcccccctca aatgccttcc gagaagccca ttgagcaggg ggcttgcatt gcaccccagc      300
ctgacagcct ggcatcttgg gataaaagca gcacagcccc ctaggggctg cccttgctgt      360
gtggcgccac cggcggtgga gaacaaggct ctattcagcc tgtgcccagg aaaggggatc      420
aggggatgcc caggcatgga cagtgggtgg caggggggga gaggagggct gtctgcttcc      480
cagaagtcca aggacacaaa tgggtgaggg gagagctctc cccatagctg ggctgcggcc      540
caaccccacc ccctcaggct atgccagggg gtgttgccag gggcacccgg gcatcgccag      600
tctagcccac tccttcataa agccctcgca tcccaggagc gagcagagcc agagcaggtt      660
ggagaggaga cgcatcacct ccgctgctcg cggggtctag agtcga                     706
```

<210> SEQ ID NO 42
<211> LENGTH: 1153
<212> TYPE: DNA
<213> ORGANISM: Artificial sequence
<220> FEATURE:
<223> OTHER INFORMATION: Nestin promoter

<400> SEQUENCE: 42

```
gaaggcagcc cccggaggtc aaaggctggg cacgcgggag gagaggccag agtcagaggc       60
tgcgggtatc tcagatatga aggaaagatg agagaggctc aggaagaggt aagaaaagac      120
acaagagacc agagaaggga gaagaattag agagggaggc agaggaccgc tgtctctaca      180
gacatagctg gtagagactg ggaggaaggg atgaaccctg agcgcatgaa gggaaggagg      240
tggctggtgg tatatggagg atgtagctgg gccagggaaa agatcctgca ctaaaaatct      300
gaagctaaaa ataacaggac acggggtgga gaggcgaaag gagggcagat tgaggcagag      360
agactgagag gcctggggat gtgggcattc cggtagggca cacagttcac ttgtcttctc      420
tttttccagg aggccaaaga tgctgacctc aagaactcat aataccccag tggggaccac      480
cgcattcata gccctgttac aagaagtggg agatgttcct ttttgtccca gactggaaat      540
```

-continued

```
ccattacatc ccgaggctca ggttctgtgg tggtcatctc tgtgtggctt gttctgtggg      600
cctacctaaa gtcctaagca cagctctcaa gcagatccga ggcgactaag atgctagtag      660
gggttgtctg gagagaagag ccgaggaggt gggctgtgat ggatcagttc agctttcaaa      720
taaaaaggcg tttttatatt ctgtgtcgag ttcgtgaacc cctgtggtgg gcttctccat      780
ctgtctgggt tagtacctgc cactatactg gaataaggag acgcctgctt ccctcgagtt      840
ggctggacaa ggttatgagc atccgtgtac ttatgggggtt gccagcttgg tcctggatcg      900
cccgggccct tcccccaccc gttcggttcc ccaccaccac ccgcgctcgt acgtgcgtct      960
ccgcctgcag ctcttgactc atcggggccc ccgggtcaca tgcgctcgct cggctctata     1020
ggcgccgccc cctgcccacc ccccgcccgc gctgggagcc gcagccgccg ccactcctgc     1080
tctctctgcg ccgccgccgt caccaccgcc accgccaccg gctgagtctg cagtcctccg     1140
aaacgggccc tct                                                        1153
```

```
<210> SEQ ID NO 43
<211> LENGTH: 438
<212> TYPE: DNA
<213> ORGANISM: Artificial sequence
<220> FEATURE:
<223> OTHER INFORMATION: Homeobox Protein 9 promoter (HB9) promoter

<400> SEQUENCE: 43
tgaataaatt taagcaggct aattaatata taaactagct caatttgtca agttgatttg       60
tattttagtt aattgtgaaa gtaattacca catggtcaaa ttaacagctt tctggaaatg      120
accaagcctg aggtttttatt tccttcctgg gtgaagaaaa ttcatttttc caagctcttg     180
atgtgatgaa taaaagtcat aaatctgggt gattggtgca ggcagagtct aaatggcttc     240
atatttcatt ttaggtttaa tagaaatatt catgctctgt tttaatgaaa ttaaattgaa     300
gggggatggg gctagagtgg ttagctgatg aattgacaaa aactaatcag ctttattggg     360
aaacaggttt aagggcacgg acgtgtcaat aacgctcagc ctgacccccct cttccattag    420 ctaggcaggc tgattaga                                                    438
```

```
<210> SEQ ID NO 44
<211> LENGTH: 3015
<212> TYPE: DNA
<213> ORGANISM: Artificial sequence
<220> FEATURE:
<223> OTHER INFORMATION: Tyrosine hydroxylase (TH) promoter

<400> SEQUENCE: 44
ctgctagggg ctgcttccca gctactcctc ttggctccgt ggcttgcctt ccagcctgtg       60
tgctgtctgg agagccttta aagcctcact tccaccaact agaagtctct ccccaaccct      120
gccctgacct caagtgcacc tcttcaaagt caggtttagc agctgcagct gggggccctg      180
aatcccaccc ctgctgtctt ccttgaagac agaagtgttg ggagctgagg atctgggcta      240
gagactggct gtatgatcca gagaagtagt gtgcttctgg gcctcagatt tcccttctgt      300
agaacaggtt tgtctgaaat ggagaggttg gtgctcctct gcagggccta gtgggagtca      360
ccatgagtgg ttaaaagatc cagcttgtct tttggtgagc tttgagagga ggtaacaggg      420
ctgagttctg gaagcctgac caagggcaga cttaaggggc ctcttggagt tgttctcatc      480
aaatggggat gggacacagc taaagtgccc agggcttctc tgtgcccaca gatgctttag      540
atcttggcac agtgtggtct accagctgtc tctctctgtg tatatatatg tatttcatag      600
```

-continued

```
acagtgtaca gtggcctggt ttgtgctatc aggctggata tggacagagg caagagtttg    660
tggcagcagt tatctcccaa gagagtccaa agacatcatg ttttcaagtt taggccaggt    720
gctacttgag agagctcaga cacagacaaa ggtctggaga gcacatgtcc tccacccccca    780 cctagcttct gttgcaagca cctccagccg agacaagaga acgaattaaa aagcaatatt    840
tgtgtcagtg taagacattt gccgaaaggt taaatccaca ttcgtgttgc tgcagagcag    900 cccctatgc  aggatttgtt agatacagct ccgtcctacc ctgtgccagc tgagcaaacg    960
ccaggctggg tggggtggaa cccagcctgg gtttgcctca ccctgcaatc cccccagcac   1020
cctctaaagg aggaccctgt ggtgggcatg cagacctagg gactgggcat agataaacctt  1080 tgggtttggg caacagcccc cactcctcag gattgaaggc taaggtgcag ccagctctgc   1140
cttcatggtg ggaatgtctc cacgtgaccc ctttctgggc tgtggagaac actcagagaa   1200
gagtcctggg atgccaggca ggccagggat gtgctgggca tgttgagaca ggagtgggct   1260
aagccagcag agttgctgac ccaggaagag ttcagaaagg ggcatggaac atggggaggg   1320
gtccatagtg agagagagca ggcagtgcag agtaaatagt ccctgagctg ggggttatgg   1380
gatttgcagg agcttgctca gagaaggcag aggagagatg ctgcgccaag ctgggtatca   1440
cagagcctca gactcctgga acaggaactg tgggggtcag gtcagcaggg gaggttaggg   1500
agtgttccct ttgtactgac ttagcattta tcctgcttct aggggggaag gggggccagt   1560
gggggatgca cagcaaggca gtgatgtggc aggcagcctg cgggagctcc tggttcctgg   1620
tgtgaaaaag ctgggaagga agagggctgg gtctggtaag tacagcaggc agttggctcc   1680
tgagagtcca agccctgtct agagggtgga gtgagatttc agaggagag ctaaacgggg    1740 tgggggctgg ggagtccagg cttctggctc ctgctaatac tcagtgtgct gggtcctcag   1800
aacctcaggg tggccatttt cagggtgaga gctctgtcct ttggcacttc tgcagactcc   1860
agtatccaga ggaataaaga tggtactctt cctcagttcc cttagtgaga ggacaccttt   1920
ctctgaaggg cttgggcagt tgtcctgaac cattgcctga aggaaggact tgactccagg   1980
gacatagaat gggctcagca taagtcccct gtagtagaga aaggtccct ctctggtctc    2040 cttagagatc ctgtttcctt ggctgaggaa gctaggtgg atctttgtgt aagtgggtgt    2100
ggatgctcac tggaaatcaa aaggcccctt ggtgttagac cttggggtgc catgggagag   2160
ttgatcactg agtgcgccct tacatggggg ccagctgaga atggggctgc ctctagctcg   2220
agaccatgat gcagggagtg agtggggag ttcaggatac tcttaactaa agcagaggtc     2280
tgtcccccca gggagggga gtcagaagac cctaggagga tgccaaaggc tagggttggc     2340
accatgttgc aggctgtgtc ttcaaggaga tgataatcag aggaatcgaa cctgcaaaag   2400
tgggccagtc ttagatacac tatagaggaa taatcttctg aaacattctg tgtctcatag   2460
gacctgcctg aggacccagc cccagtgcca gcacatacac tggggcagtg agtagatagt   2520
atactttgtt acatgggctg gggggacatg gcctgtgccc tggagggggac ttgaagacat   2580 ccaaaaagct agtgagaggg ctcctagatt tatttgtctc caagggctat atatagcctt   2640
cctaacatga acccttgggt aatccagcat gggcgctccc atatgccctg gtttgattag   2700
agagctctag atgtctcctg tcccagaaca ccagccagcc cctgtcttca tgtcgtgtct   2760
agggcggagg gtgattcaga ggcaggtgcc tgcgacagtg gatgcaatta gatctaatgg   2820
gacggaggcc tctctcgtcc gtcgccctcg ctctgtgccc accccgcct cccctcaggca    2880 cagcaggcgt ggagaggatg cgcaggaggt aggaggtggg ggacccagag gggctttgac   2940
gtcagcctgg cctttaagag gccgcctgcc tggcaagggc cgtggagaca gaactcggga   3000
```

-continued

```
ccaccagctt gcact                                                                     3015

<210> SEQ ID NO 45
<211> LENGTH: 1353
<212> TYPE: DNA
<213> ORGANISM: Artificial sequence
<220> FEATURE:
<223> OTHER INFORMATION: Myelin basic protein (MBP) promoter

<400> SEQUENCE: 45
caccgtggct ttaacactta gagaaaatgc atcccctcta atcaataagt catcgacagt      60
gggtagatgg aggaacggca gtgcgtagta ggatgcgtgc aagcatagtc tcgtgcatgg     120
gtgcatagat cgctgggcag gtggacaagg tgggggtgga taaagaagtg ggtagatgat     180
tgatgttagg taaatatcac tgggtggaca gatgggtggt aggtgatggg atggttagaa     240
tagtcagaag agggatggat tgataaggtg aacagatgat aaatgggtga tagactggaa     300
gggttgtcaa aagaggataa gggaagtgtg agctagccgt atttctaagg tcagtaatag     360
agttgggaga agaggttaag ttacatccat ttaaacctca cacgaagctg agagggaatg     420
gacttgctgc cgttggtgag gaaagcgttg catttcccgt gtgcttggtt gtgaagtgct     480
caggtcccac atgaagcagt caggttactg cggcttacag aggagccaga tccaaatgcc     540
ccgagtaagc acgtccccga gccagaggcc tccagcggaa tccgggagag ggattgctca     600
gtgccctgct tccctggact gtaagctgca gaaagatgtg ggaagtcctg ttctccactg     660
agaacactaa aagcaccttt tgtcaaacga ccgcttcaca tctggggctt gtgcactggt     720
ggccttttaa accagagaca acccacaaga tacctaacct gcggggctct ctggtacagt     780
gagcaactca ggaaatgctt tggcttgatt gctgtgggct ctcaggccat cgccctctgg     840
agtggttctt ttaatgagaa cctgaagatt ggcccctgag ccatgtatac caagcaagct     900
caatccaggt tagctccctc tggttggggc aagctaacgt gctccttggg ccccgcgcgt     960
aactgtgcgt tttataggag acagctagtt caagacccca ggaagaaagc ggctttgtcc    1020
ccctctaggc ctcgtacagg cccacattca tatctcattg ttgttgcagg ggaggcagat    1080
gcgatccaga acaatgggac ctcggctgag gacacggcgg tgacagactc caagcacaca    1140
gcagacccaa agaataactg gcaaggcgcc cacccagctg acccagggaa ccgcccccac    1200
ttgatccgcc tctttttcccg agatgccccg ggaagggagg acaacacctt caaagacagg    1260
ccctcagagt ccgacgagct tcagaccatc caagaagatc ccacagcagc ttccgaagaa    1320
ttctgcagtc gacggtaccg cgggcccggg atc                                 1353

<210> SEQ ID NO 46
<211> LENGTH: 7030
<212> TYPE: DNA
<213> ORGANISM: Artificial sequence
<220> FEATURE:
<223> OTHER INFORMATION: pAAV-CAG-moFGF21

<400> SEQUENCE: 46
agtgagcgag cgagcgcgca gctgcattaa tgaatcggcc aacgcgcggg gagaggcggt      60
ttgcgtattg ggcgctcttc cgcttcctcg ctcactgact cgctgcgctc ggtcgttcgg     120
ctgcggcgag cggtatcagc tcactcaaag gcggtaatac ggttatccac agaatcaggg     180
gataacgcag gaaagaacat gtgagcaaaa ggccagcaaa aggccaggaa ccgtaaaaag     240
gccgcgttgc tggcgttttt ccataggctc cgcccccctg acgagcatca caaaaatcga     300
```

-continued

```
cgctcaagtc agaggtggcg aaacccgaca ggactataaa gataccaggc gtttcccct     360 ggaagctccc tcgtgcgctc tcctgttccg accctgccgc ttaccggata cctgtccgcc     420
tttctccctt cgggaagcgt ggcgctttct catagctcac gctgtaggta tctcagttcg     480
gtgtaggtcg ttcgctccaa gctgggctgt gtgcacgaac cccccgttca gcccgaccgc     540
tgcgccttat ccggtaacta tcgtcttgag tccaacccgg taagacacga cttatcgcca     600
ctggcagcag ccactggtaa caggattagc agagcgaggt atgtaggcgg tgctacagag     660
ttcttgaagt ggtggcctaa ctacggctac actagaagaa cagtatttgg tatctgcgct     720
ctgctgaagc cagttacctt cggaaaaaga gttggtagct cttgatccgg caaacaaacc     780
accgctggta gcggtggttt ttttgtttgc aagcagcaga ttacgcgcag aaaaaaagga     840
tctcaagaag atcctttgat cttttctacg gggtctgacg ctcagtggaa cgaaaactca     900
cgttaaggga ttttggtcat gagattatca aaaaggatct tcacctagat cctttttaaat    960 taaaaatgaa gttttaaatc aatctaaagt atatatgagt aaacttggtc tgacagttac    1020
caatgcttaa tcagtgaggc acctatctca gcgatctgtc tatttcgttc atccatagtt    1080
gcctgactcc ccgtcgtgta gataactacg atacgggagg gcttaccatc tggccccagt    1140
gctgcaatga taccgcgaga cccacgctca ccggctccag atttatcagc aataaaccag    1200
ccagccggaa gggccgagcg cagaagtggt cctgcaactt tatccgcctc catccagtct    1260
attaattgtt gccgggaagc tagagtaagt agttcgccag ttaatagttt gcgcaacgtt    1320
gttgccattg ctacaggcat cgtggtgtca cgctcgtcgt ttggtatggc ttcattcagc    1380
tccggttccc aacgatcaag gcgagttaca tgatccccca tgttgtgcaa aaaagcggtt    1440
agctccttcg gtcctccgat cgttgtcaga gtaagttgg ccgcagtgtt atcactcatg    1500
gttatggcag cactgcataa ttctcttact gtcatgccat ccgtaagatg cttttctgtg    1560
actggtgagt actcaaccaa gtcattctga aatagtgta tgcggcgacc gagttgctct    1620
tgcccggcgt caatacggga taataccgcg ccacatagca gaactttaaa agtgctcatc    1680
attggaaaac gttcttcggg gcgaaaactc tcaaggatct taccgctgtt gagatccagt    1740
tcgatgtaac ccactcgtgc acccaactga tcttcagcat cttttacttt caccagcgtt    1800
tctgggtgag caaaaacagg aaggcaaaat gccgcaaaaa agggaataag ggcgacacgg    1860
aaatgttgaa tactcatact cttccttttt caatattatt gaagcattta tcagggttat    1920
tgtctcatga gcggatacat atttgaatgt atttagaaaa ataaacaaat aggggttccg    1980
cgcacatttc cccgaaaagt gccacctgac gtctaagaaa ccattattat catgacatta    2040
acctataaaa ataggcgtat cacgaggccc tttcgtctcg cgcgtttcgg tgatgacggt    2100
gaaaacctct gacacatgca gctcccggag acggtcacag cttgtctgta agcggatgcc    2160
gggagcagac aagcccgtca gggcgcgtca gcgggtgttg gcgggtgtcg gggctggctt    2220
aactatgcgg catcagagca gattgtactg agagtgcacc atatgcggtg tgaaataccg    2280
cacagatgcg taaggagaaa ataccgcatc aggcgattcc aacatccaat aaatcataca    2340
ggcaaggcaa agaattagca aaattaagca ataaagcctc agagcataaa gctaaatcgg    2400
ttgtaccaaa aacattatga ccctgtaata cttttgcggg agaagccttt atttcaacgc    2460
aaggataaaa attttttagaa ccctcatata ttttaaatgc aatgcctgag taatgtgtag    2520
gtaaagattc aaacgggtga aaaggccgg agacagtcaa atcaccatca atatgatatt    2580
caaccgttct agctgataaa ttcatgccgg agagggtagc tatttttgag aggtctctac    2640
aaaggctatc aggtcattgc ctgagagtct ggagcaaaca agagaatcga tgaacggtaa    2700
```

-continued

```
tcgtaaaact agcatgtcaa tcatatgtac cccggttgat aatcagaaaa gccccaaaaa      2760
caggaagatt gtataagcaa atatttaaat tgtaagcgtt aatattttgt taaaattcgc      2820
gttaaatttt tgttaaatca gctcattttt taaccaatag gccgaaatcg gcaaaatccc      2880
ttataaatca aaagaataga ccgagatagg gttgagtgtt gttccagttt ggaacaagag      2940
tccactatta aagaacgtgg actccaacgt caaagggcga aaaccgtct atcagggcga       3000 tggcccacta cgtgaaccat caccctaatc aagttttttg gggtcgaggt gccgtaaagc      3060
actaaatcgg aaccctaaag ggagcccccg atttagagct tgacggggaa agccggcgaa      3120
cgtggcgaga aaggaaggga agaaagcgaa aggagcgggc gctagggcgc tggcaagtgt      3180
agcggtcacg ctgcgcgtaa ccaccacacc cgccgcgctt aatgcgccgc tacagggcgc      3240
gtactatggt tgctttgacg agcacgtata acgtgctttc ctcgttagaa tcagagcggg      3300
agctaaacag gaggccgatt aaagggattt tagacaggaa cggtacgcca gaatcctgag      3360
aagtgttttt ataatcagtg aggccaccga gtaaaagagt ctgtccatca cgcaaattaa      3420
ccgttgtcgc aatacttctt tgattagtaa taacatcact tgcctgagta gaagaactca      3480
aactatcggc cttgctggta atatccagaa caatattacc gccagccatt gcaacggaat      3540
cgccattcgc cattcaggct gcgcaactgt tgggaagggc gatcggtgcg ggcctcttcc      3600
actgaggccc agctgcgcgc tcgctcgctc actgaggccg cccgggcaaa gcccgggcgt      3660
cgggcgacct ttggtcgccc ggcctcagtg agcgagcgag cgcgcagaga gggagtggcc      3720
aactccatca ctaggggttc cttgtagtta atgattaacc cgccatgcta cttatctact      3780
cgacattgat tattgactag ttattaatag taatcaatta cggggtcatt agttcatagc      3840
ccatatatgg agttccgcgt tacataactt acggtaaatg gcccgcctgg ctgaccgccc      3900 aacgacccc gcccattgac gtcaataatg acgtatgttc ccatagtaac gccaataggg       3960
actttccatt gacgtcaatg ggtggagtat ttacggtaaa ctgcccactt ggcagtacat      4020
caagtgtatc atatgccaag tacgcccct attgacgtca atgacggtaa atggcccgcc       4080
tggcattatg cccagtacat gaccttatgg gactttccta cttggcagta catctacgta      4140
ttagtcatcg ctattaccat ggtcgaggtg agccccacgt tctgcttcac tctccccatc      4200 tccccccct ccccacccc aattttgtat ttatttattt tttaattatt ttgtgcagcg       4260 atggggcgg gggggggggg gggcgcgcgc ccaggcgggg cggggcgggg cgagggggcgg      4320 ggcggggcga ggcggagagg tgcggcggca gccaatcaga gcggcgcgct ccgaaagttt      4380 cctttttatgg cgaggcggcg gcggcggcgg ccctataaaa agcgaagcgc gcggcgggcg      4440
ggagtcgctg cgttgccttc gccccgtgcc ccgctccgcg ccgcctcgcg ccgcccgccc      4500
cggctctgac tgaccgcgtt actcccacag gtgagcgggc gggacggccc ttctcctccg      4560
ggctgtaatt agcgcttggt ttaatgacgg cttgtttctt ttctgtggct gcgtgaaagc      4620
cttgaggggc tccggagggg ccctttgtgc gggggagcg gctcggggggg tgcgtgcgtg      4680 tgtgtgtgcg tggggagcgc cgcgtgcggc tccgcgctgc ccggcggctg tgagcgctgc      4740
gggcgcggcg cggggctttg tgcgctccgc agtgtgcgcg aggggagcgc ggccgggggc      4800
ggtgccccgc ggtgcggggg gctgcgaggg gaacaaaggc tgcgtgcggg gtgtgtgcgt      4860 ggggggtga gcagggggtg tgggcgcgtc ggtcgggctg caacccccc tgcacccccc       4920 tccccgagtt gctgagcacg gcccggcttc gggtgcgggg ctccgtacgg ggcgtggcgc      4980
ggggctcgcc gtgccgggcg ggggtggcg gcaggtgggg gtgccgggcg gggcggggcc      5040
```

```
gcctcgggcc ggggagggct cggggaggg gcgcggcggc ccccggagcg ccggcggctg      5100
tcgaggcgcg gcgagccgca gccattgcct tttatggtaa tcgtgcgaga gggcgcaggg      5160
acttcctttg tcccaaatct gtgcggagcc gaaatctggg aggcgccgcc gcacccctc       5220 tagcgggcgc ggggcgaagc ggtgcggcgc cggcaggaag gaaatgggcg gggagggcct      5280
tcgtgcgtcg ccgcgccgcc gtccccttct ccctctccag cctcggggct gtccgcgggg      5340
ggacggctgc cttcgggggg gacggggcag ggcgggggttc ggcttctggc gtgtgaccgg      5400
cggctctaga gcctctgcta accatgttca tgccttcttc tttttcctac agctcctggg      5460
caacgtgctg gttattgtgc tgtctcatca ttttggcaaa gaattgatta attcgagcga      5520
acgcgtcgag tcgctcggta cgatttaaat tgaattggcc tcgagcgcaa gcttgagcta      5580
gcgccaccat ggaatggatg agaagcagag tgggcaccct gggcctgtgg gtgcgactgc      5640
tgctggctgt gtttctgctg ggcgtgtacc aggcctaccc catccctgac tctagccccc      5700
tgctgcagtt tggcggacaa gtgcggcaga gatacctgta caccgacgac gaccaggaca      5760
ccgaggccca cctggaaatc cgcgaggatg gcacagtcgt gggcgctgct cacagaagcc      5820
ctgagagcct gctggaactg aaggccctga gcccggcgt gatccagatc ctgggcgtga      5880
aggccagcag attcctgtgc cagcagcctg acggcgccct gtacggctct cctcacttcg      5940
atcctgaggc ctgcagcttc agagagctgc tgctggagga cggctacaac gtgtaccagt      6000
ctgaggccca cggcctgccc ctgagactgc ctcagaagga cagccctaac caggacgcca      6060
caagctgggg acctgtgcgg ttcctgccta tgcctggact gctgcacgag ccccaggatc      6120
aggctggctt tctgcctcct gagcctccag acgtgggcag cagcgaccct ctgagcatgg      6180
tggaacctct gcagggcaga agccccagct acgcctcttg agaatgcggg cccggtaccc      6240
ccgacgcggc ctaactggcc tcatgggcct tccgctcact gcccgctttc cagtcgggaa      6300
acctgtcgtg ccagtcaggt gcaggctgcc tatcagaagg tggtggctgg tgtggccaat      6360
gccctggctc acaaatacca ctgagatctt tttccctctg ccaaaaatta tggggacatc      6420
atgaagcccc ttgagcatct gacttctggc taataaagga aatttatttt cattgcaata      6480
gtgtgttgga attttttgtg tctctcactc ggaaggacat atgggagggc aaatcattta      6540
aaacatcaga atgagtattt ggtttagagt ttggcaacat atgcccatat gctggctgcc      6600
atgaacaaag gttggctata aagaggtcat cagtatatga aacagccccc tgctgtccat      6660
tccttattcc atagaaaagc cttgacttga ggttagattt tttttatatt ttgttttgtg      6720
ttattttttt cttaacatc cctaaaattt tccttacatg ttttactagc cagatttttc       6780
ctcctctcct gactactccc agtcatagct gtccctcttc tcttatggag atccctcgac      6840
ctgcagccca agctgtagat aagtagcatg gcgggttaat cattaactac aaggaaccccc     6900 tagtgatgga gttggccact ccctctctgc gcgctcgctc gctcactgag gccgggcgac      6960
caaaggtcgc ccgacgcccg ggctttgccc gggcggcctc agtgagcgag cgagcgcgca      7020
gctggcgtaa                                                            7030
```

<210> SEQ ID NO 47
<211> LENGTH: 20
<212> TYPE: DNA
<213> ORGANISM: Artificial sequence
<220> FEATURE:
<223> OTHER INFORMATION: moFgf21-Fw

<400> SEQUENCE: 47

```
cctaaccagg acgccacaag                                                    20
```

<210> SEQ ID NO 48
<211> LENGTH: 20
<212> TYPE: DNA
<213> ORGANISM: Artificial sequence
<220> FEATURE:
<223> OTHER INFORMATION: moFgf21-Rv

<400> SEQUENCE: 48
gttccaccat gctcagaggg                                                          20

<210> SEQ ID NO 49
<211> LENGTH: 22
<212> TYPE: DNA
<213> ORGANISM: Artificial sequence
<220> FEATURE:
<223> OTHER INFORMATION: Gfap-Fw

<400> SEQUENCE: 49
acagactttc tccaacctcc ag                                                       22

<210> SEQ ID NO 50
<211> LENGTH: 20
<212> TYPE: DNA
<213> ORGANISM: Artificial sequence
<220> FEATURE:
<223> OTHER INFORMATION: Gfap-Rv

<400> SEQUENCE: 50
ccttctgaca cggatttggt                                                          20

<210> SEQ ID NO 51
<211> LENGTH: 22
<212> TYPE: DNA
<213> ORGANISM: Artificial sequence
<220> FEATURE:
<223> OTHER INFORMATION: S100b-Fw

<400> SEQUENCE: 51
aacaacgagc tctctcactt cc                                                       22

<210> SEQ ID NO 52
<211> LENGTH: 20
<212> TYPE: DNA
<213> ORGANISM: Artificial sequence
<220> FEATURE:
<223> OTHER INFORMATION: S100b-Rv

<400> SEQUENCE: 52
cgtctccatc actttgtcca                                                          20

<210> SEQ ID NO 53
<211> LENGTH: 20
<212> TYPE: DNA
<213> ORGANISM: Artificial sequence
<220> FEATURE:
<223> OTHER INFORMATION: Aif1-Fw

<400> SEQUENCE: 53
tgagccaaag cagggatttg                                                          20

<210> SEQ ID NO 54
<211> LENGTH: 20
<212> TYPE: DNA
<213> ORGANISM: Artificial sequence
<220> FEATURE:

-continued

<223> OTHER INFORMATION: Aif1-Rv

<400> SEQUENCE: 54
tcaagtttgg acggcagatc                                              20

<210> SEQ ID NO 55
<211> LENGTH: 20
<212> TYPE: DNA
<213> ORGANISM: Artificial sequence
<220> FEATURE:
<223> OTHER INFORMATION: Nfkb-Fw

<400> SEQUENCE: 55
gaccactgct caggtccact                                              20

<210> SEQ ID NO 56
<211> LENGTH: 20
<212> TYPE: DNA
<213> ORGANISM: Artificial sequence
<220> FEATURE:
<223> OTHER INFORMATION: Nfkb-Rv

<400> SEQUENCE: 56
tgtcactatc ccggagttca                                              20

<210> SEQ ID NO 57
<211> LENGTH: 20
<212> TYPE: DNA
<213> ORGANISM: Artificial sequence
<220> FEATURE:
<223> OTHER INFORMATION: Il1b-Fw

<400> SEQUENCE: 57
atgaagggct gcttccaaac                                              20

<210> SEQ ID NO 58
<211> LENGTH: 20
<212> TYPE: DNA
<213> ORGANISM: Artificial sequence
<220> FEATURE:
<223> OTHER INFORMATION: Il1b-Rv

<400> SEQUENCE: 58
atgtgctgct gcgagatttg                                              20

<210> SEQ ID NO 59
<211> LENGTH: 20
<212> TYPE: DNA
<213> ORGANISM: Artificial sequence
<220> FEATURE:
<223> OTHER INFORMATION: Il6-Fw

<400> SEQUENCE: 59
tcgctcaggg tcacaagaaa                                              20

<210> SEQ ID NO 60
<211> LENGTH: 22
<212> TYPE: DNA
<213> ORGANISM: Artificial sequence
<220> FEATURE:
<223> OTHER INFORMATION: Il6-Rv

<400> SEQUENCE: 60
catcagaggc aaggaggaaa ac                                           22

-continued

```
<210> SEQ ID NO 61
<211> LENGTH: 20
<212> TYPE: DNA
<213> ORGANISM: Artificial sequence
<220> FEATURE:
<223> OTHER INFORMATION: Ucp1-Fw

<400> SEQUENCE: 61
ggcctctacg actcagtcca                                          20

<210> SEQ ID NO 62
<211> LENGTH: 20
<212> TYPE: DNA
<213> ORGANISM: Artificial sequence
<220> FEATURE:
<223> OTHER INFORMATION: Ucp1-Rv

<400> SEQUENCE: 62
taagccggct gagatcttgt                                          20

<210> SEQ ID NO 63
<211> LENGTH: 20
<212> TYPE: DNA
<213> ORGANISM: Artificial sequence
<220> FEATURE:
<223> OTHER INFORMATION: Cidea-Fw

<400> SEQUENCE: 63
aaaccatgac cgaagtagcc                                          20

<210> SEQ ID NO 64
<211> LENGTH: 23
<212> TYPE: DNA
<213> ORGANISM: Artificial sequence
<220> FEATURE:
<223> OTHER INFORMATION: Cidea-Rv

<400> SEQUENCE: 64
aggccagttg tgatgactaa gac                                      23

<210> SEQ ID NO 65
<211> LENGTH: 22
<212> TYPE: DNA
<213> ORGANISM: Artificial sequence
<220> FEATURE:
<223> OTHER INFORMATION: Tnfa-Fw

<400> SEQUENCE: 65
cggcatggat ctcaaagaca ac                                       22

<210> SEQ ID NO 66
<211> LENGTH: 20
<212> TYPE: DNA
<213> ORGANISM: Artificial sequence
<220> FEATURE:
<223> OTHER INFORMATION: Tnfa-Rv

<400> SEQUENCE: 66
agatagcaaa tcggctgacg                                          20

<210> SEQ ID NO 67
<211> LENGTH: 22
<212> TYPE: DNA
<213> ORGANISM: Artificial sequence
<220> FEATURE:
<223> OTHER INFORMATION: F4/80-Fw
```

-continued

```
<400> SEQUENCE: 67
ctttggctat gggcttccag tc                                              22

<210> SEQ ID NO 68
<211> LENGTH: 21
<212> TYPE: DNA
<213> ORGANISM: Artificial sequence
<220> FEATURE:
<223> OTHER INFORMATION: F4/80-Rv

<400> SEQUENCE: 68
gcaaggagga cagagtttat c                                               21

<210> SEQ ID NO 69
<211> LENGTH: 20
<212> TYPE: DNA
<213> ORGANISM: Artificial sequence
<220> FEATURE:
<223> OTHER INFORMATION: Rplp0-Fw

<400> SEQUENCE: 69
actggtctag gacccgagaa                                                 20

<210> SEQ ID NO 70
<211> LENGTH: 20
<212> TYPE: DNA
<213> ORGANISM: Artificial sequence
<220> FEATURE:
<223> OTHER INFORMATION: Rplp0-Fw

<400> SEQUENCE: 70
tcccaccttg tctccagtct                                                 20
```